United States Patent [19]
Anthony et al.

[11] Patent Number: 5,859,035
[45] Date of Patent: Jan. 12, 1999

[54] ARYLHETEROARYL INHIBITORS OF FARNESYL-PROTEIN TRANSFERASE

[75] Inventors: Neville J. Anthony, Hatfield; Robert P. Gomez, Perkasie; Steven D. Young, Lansdale, all of Pa.

[73] Assignee: Merck & Co., Inc., Rahway, N.J.

[21] Appl. No.: 827,486

[22] Filed: Mar. 27, 1997

Related U.S. Application Data

[60] Provisional application No. 60/014,592 Apr. 3, 1996 and provisional application No. 60/022,340 Jul. 24, 1996.

[51] Int. Cl.⁶ .................. A61K 31/415; A61K 31/41; A61K 31/42; C07D 275/06; C07D 277/20; C07D 261/06

[52] U.S. Cl. .................. 514/365; 514/374; 514/378; 514/397; 548/202; 548/208; 548/238; 548/247; 548/314.4

[58] Field of Search .................. 548/202, 238, 548/247, 208, 314.4; 514/374, 397, 365, 378

[56] References Cited

U.S. PATENT DOCUMENTS

| | | | |
|---|---|---|---|
| 4,207,324 | 6/1980 | Matsumura et al. | 424/273 R |
| 4,769,470 | 9/1988 | Georgiev et al. | 548/240 |
| 4,977,176 | 12/1990 | Amstutz et al. | 514/397 |
| 5,021,434 | 6/1991 | Strehlke et al. | 514/341 |
| 5,140,034 | 8/1992 | Baker et al. | 514/364 |

FOREIGN PATENT DOCUMENTS

| | | | |
|---|---|---|---|
| 0280017 | 8/1988 | European Pat. Off. | 548/238 |
| 322266 | 2/1984 | Germany | 548/315.1 |
| 58-150591 | 9/1983 | Japan | 548/315.1 |

*Primary Examiner*—Floyd D. Higel
*Attorney, Agent, or Firm*—David A. Muthard; Mark R. Daniel

[57] ABSTRACT

The present invention is directed to compounds which inhibit farnesyl-protein transferase (FTase) and the farnesylation of the oncogene protein Ras. The invention is further directed to chemotherapeutic compositions containing the compounds of this invention and methods for inhibiting farnesyl-protein transferase and the farnesyl of the oncogene protein Ras.

31 Claims, No Drawings

ARYLHETEROARYL INHIBITORS OF FARNESYL-PROTEIN TRANSFERASE

This application claims the benefit of U.S. Provisional Application Nos. 60/014,592 and 60/022,340 filed Apr. 3, 1996, and Jul. 24, 1996, respectively.

BACKGROUND OF THE INVENTION

The Ras proteins (Ha-Ras, Ki4a-Ras, Ki4b-Ras and N-Ras) are part of a signalling pathway that links cell surface growth factor receptors to nuclear signals initiating cellular proliferation. Biological and biochemical studies of Ras action indicate that Ras functions like a G-regulatory protein. In the inactive state, Ras is bound to GDP. Upon growth factor receptor activation Ras is induced to exchange GDP for GTP and undergoes a conformational change. The GTP-bound form of Ras propagates the growth stimulation signal until the signal is terminated by the intrinsic GTPase activity of Ras, which returns the protein to its inactive GDP bound form (D. R. Lowy and D. M. Willumsen, Ann. Rev. Biochem. 62:851–891 (1993)). Mutated ras genes (Ha-ras, Ki4a-ras, Ki4b-ras and N-ras) are found in many human cancers, including colorectal carcinoma, exocrine pancreatic carcinoma, and myeloid leukemias. The protein products of these genes are defective in their GTPase activity and constitutively transmit a growth stimulation signal.

Ras must be localized to the plasma membrane for both normal and oncogenic functions. At least 3 post-translational modifications are involved with Ras membrane localization, and all 3 modifications occur at the C-terminus of Ras. The Ras C-terminus contains a sequence motif termed a "CAAX" or "Cys-Aaa$^1$-Aaa$^2$-Xaa" box (Cys is cysteine, Aaa is an aliphatic amino acid, the Xaa is any amino acid) (Willumsen et al., Nature 310:583–586 (1984)). Depending on the specific sequence, this motif serves as a signal sequence for the enzymes farnesyl-protein transferase or geranylgeranyl-protein transferase, which catalyze the alkylation of the cysteine residue of the CAAX motif with a $C_{15}$ or $C_{20}$ isoprenoid, respectively. (S. Clarke., Ann. Rev. Biochem. 61:355–386 (1992); W. R. Schafer and J. Rine, Ann. Rev. Genetics 30:209–237 (1992)). The Ras protein is one of several proteins that are known to undergo post-translational farnesylation. Other farnesylated proteins include the Ras-related GTP-binding proteins such as Rho, fungal mating factors, the nuclear lamins, and the gamma subunit of transducin. James, et al., J. Biol. Chem. 269, 14182 (1994) have identified a peroxisome associated protein Pxf which is also farnesylated. James, et al., have also suggested that there are farnesylated proteins of unknown structure and function in addition to those listed above.

Inhibition of farnesyl-protein transferase has been shown to block the growth of Ras-transformed cells in soft agar and to modify other aspects of their transformed phenotype. It has also been demonstrated that certain inhibitors of farnesyl-protein transferase selectively block the processing of the Ras oncoprotein intracellularly (N. E. Kohl et al., Science, 260:1934–1937 (1993) and G. L. James et al., Science, 260:1937–1942 (1993). Recently, it has been shown that an inhibitor of farnesyl-protein transferase blocks the growth of ras-dependent tumors in nude mice (N. E. Kohl et al., Proc. Natl. Acad. Sci U.S.A., 91:9141–9145 (1994) and induces regression of mammary and salivary carcinomas in ras transgenic mice (N. E. Kohl et al., Nature Medicine, 1:792–797 (1995).

Indirect inhibition of farnesyl-protein transferase in vivo has been demonstrated with lovastatin (Merck & Co., Rahway, N.J.) and compactin (Hancock et al., ibid; Casey et al., ibid; Schafer et al., Science 245:379 (1989)). These drugs inhibit HMG-CoA reductase, the rate limiting enzyme for the production of polyisoprenoids including farnesyl pyrophosphate. Farnesyl-protein transferase utilizes farnesyl pyrophosphate to covalently modify the Cys thiol group of the Ras CAAX box with a farnesyl group (Reiss et al., Cell, 62:81–88 (1990); Schaber et al., J. Biol. Chem., 265:14701–14704 (1990); Schafer et al., Science, 249:1133–1139 (1990); Manne et al., Proc. Natl. Acad. Sci USA, 87:7541–7545 (1990)). Inhibition of farnesyl pyrophosphate biosynthesis by inhibiting HMG-CoA reductase blocks Ras membrane localization in cultured cells. However, direct inhibition of farnesyl-protein transferase would be more specific and attended by fewer side effects than would occur with the required dose of a general inhibitor of isoprene biosynthesis.

Inhibitors of farnesyl-protein transferase (FPTase) have been described in four general classes (S. Graham, Expert Opinion Ther. Patents, (1995) 5:1269–1285). The first are analogs of farnesyl diphosphate (FPP), while a second class of inhibitors is related to the protein substrates (e.g., Ras) for the enzyme. Bisubstrate inhibitors and inhibitors of farnesyl-protein transferase that are non-competitive with the substrates have also been described. The peptide derived inhibitors that have been described are generally cysteine containing molecules that are related to the CAAX motif that is the signal for protein prenylation. (Schaber et al., ibid; Reiss et. al., ibid; Reiss et al., PNAS, 88:732–736 (1991)). Such inhibitors may inhibit protein prenylation while serving as alternate substrates for the farnesyl-protein transferase enzyme, or may be purely competitive inhibitors (U.S. Pat. No. 5,141,851, University of Texas; N. E. Kohl et al., Science, 260:1934–1937 (1993); Graham, et al., J. Med. Chem., 37, 725 (1994)). In general, deletion of the thiol from a CAAX derivative has been shown to dramatically reduce the inhibitory potency of the compound. However, the thiol group potentially places limitations on the therapeutic application of FPTase inhibitors with respect to pharmacokinetics, pharmacodynamics and toxicity. Therefore, a functional replacement for the thiol is desirable.

It has recently been disclosed that certain tricyclic compounds which optionally incorporate a piperidine moiety are inhibitors of FPTase (WO 95/10514, WO 95/10515 and WO 95/10516). Imidazole-containing inhibitors of farnesyl protein transferase have also been disclosed (WO 95/09001 and EP 0 675 112 A1).

It has recently been reported that farnesyl-protein transferase inhibitors are inhibitors of proliferation of vascular smooth muscle cells and are therefore useful in the prevention and therapy of arteriosclerosis and diabetic disturbance of blood vessels (JP H7-112930).

It is, therefore, an object of this invention to develop low molecular weight compounds that will inhibit farnesyl-protein transferase and thus, the post-translational farnesylation of proteins. It is a further object of this invention to develop chemotherapeutic compositions containing the compounds of this invention and methods for producing the compounds of this invention.

SUMMARY OF THE INVENTION

The present invention comprises arylheteroaryl-containing compounds which inhibit the farnesyl-protein transferase. Further contained in this invention are chemotherapeutic compositions containing these farnesyl transferase inhibitors and methods for their production.

The compounds of this invention are illustrated by the formula A:

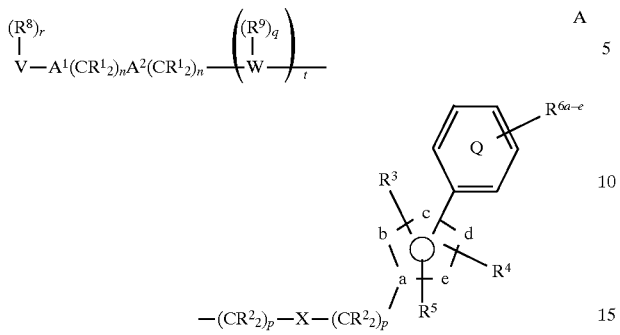

DETAILED DESCRIPTION OF THE INVENTION

The compounds of this invention are useful in the inhibition of farnesyl-protein transferase and the farnesylation of the oncogene protein Ras. In a first embodiment of this invention, the inhibitors of farnesyl-protein transferase are illustrated by the formula A:

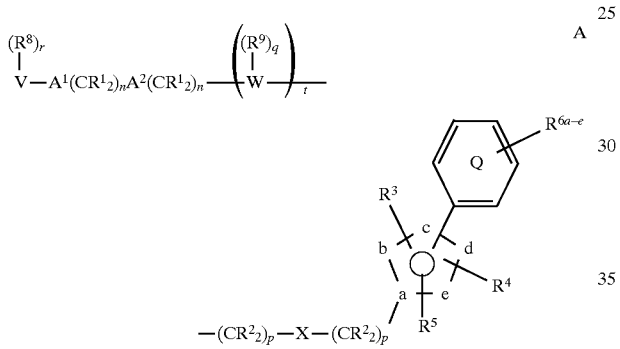

wherein:

a is N or C;

from 0–4 of b, c, d and e are independently N, NH, O and S, and the remaining b, c, d and e atoms are independently CH, provided that if a is C, then at least one of b, c, d or e is independently N, NH, O or S;

$R^1$ and $R^2$ are independently selected from:
a) hydrogen,
b) aryl, heterocycle, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $R^{11}C(O)O$—, $(R^{10})_2NC(O)$—, $R^{10}_2N$—$C(NR^{10})$—, CN, $NO_2$, $R^{10}C(O)$—, $N_3$, —$N(R^{10})_2$, or $R^{11}OC(O)NR^{10}$—,
c) unsubstituted or substituted $C_1$–$C_6$ alkyl wherein the substituent on the substituted $C_1$–$C_6$ alkyl is selected from unsubstituted or substituted aryl, heterocyclic, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2NC(O)$—, $R^{10}_2N$—$C(NR^{10})$—, CN, $R^{10}C(O)$—, $N_3$, —$N(R^{10})_2$, and $R^{11}OC(O)$—$NR^{10}$—;

$R^3$, $R^4$ and $R^5$ are independently selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}C(O)O$—, $R^{11}S(O)_m$—, $R^{10}C(O)NR^{10}$—, $(R^{10})_2NC(O)$—, $R^{10}_2N$—$C(NR^{10})$—, CN, $NO_2$, $R^{10}C(O)$—, $N_3$, —$N(R^{10})_2$, or $R^{11}OC(O)NR^{10}$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{10}_2N$—$C(NR^{10})$—, CN, $R^{10}C(O)$—, $N_3$, —$N(R^{10})_2$, and $R^{11}OC(O)$—$NR^{10}$—;

$R^{6a}$, $R^{6b}$, $R^{6c}$, $R^{6d}$ and $R^{6e}$ are independently selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $R^{11}C(O)O$—, $R^{10}_2N$—$C(NR^{10})$—, CN, $NO_2$, $R^{10}C(O)$—, $N_3$, —$N(R^{10})_2$, or $R^{11}OC(O)NR^{10}$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{10}_2N$—$C(NR^{10})$—, CN, $R^{10}C(O)$—, $N_3$, —$N(R^{10})_2$, and $R^{11}OC(O)$—$NR^{10}$—; or any two of $R^{6a}$, $R^{6b}$, $R^{6c}$, $R^{6d}$ and $R^{6e}$ on adjacent carbon atoms are combined to form a diradical selected from —CH=CH—CH=CH—, —CH=CH—$CH_2$—, —$(CH_2)_4$— and —$(CH_2)_3$—;

provided that when $R^{6a}$, $R^{6b}$, $R^{6c}$, $R^{6d}$ or $R^{6e}$ is unsubstituted or substituted heterocycle, attachment of $R^{6a}$, $R^{6b}$, $R^{6c}$, $R^{6d}$ or $R^{6e}$ to Q is through a substitutable ring carbon;

$R^7$ is selected from: H; $C_{1-4}$ alkyl, $C_{3-6}$ cycloalkyl, heterocycle, aryl, aroyl, heteroaroyl, arylsulfonyl, heteroarylsulfonyl, unsubstituted or substituted with:
a) $C_{1-4}$ alkoxy,
b) aryl or heterocycle,
c) halogen,
d) HO,
e) 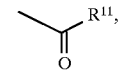
f) —$SO_2R^{11}$
g) $N(R^{10})_2$ or
h) $C_{1-4}$ perfluoroalkyl;

$R^8$ is independently selected from:
a) hydrogen,
b) aryl, substituted aryl, heterocycle, $C_3$–$C_{10}$ cycloalkyl, $C_2$–$C_6$ alkenyl, $C_2$–$C_6$ alkynyl, perfluoroalkyl, F, Cl, Br, $R^{10}O$—, $R^{11}S(O)_m$—, $R^{10}C(O)NR^{10}$—, $(R^{10})_2NC(O)$—, $R^{10}_2N$—$C(NR^{10})$—, CN, $NO_2$, $R^{10}C(O)$—, $N_3$, —$N(R^{10})_2$, or $R^{11}OC(O)NR^{10}$—, and
c) $C_1$–$C_6$ alkyl unsubstituted or substituted by aryl, cyanophenyl, heterocycle, $C_3$–$C_{10}$ cycloalkyl, $C_2$–$C_6$ alkenyl, $C_2$–$C_6$ alkynyl, perfluoroalkyl, F, Cl, Br, $R^{10}O$—, $R^{11}S(O)_m$—, $R^{10}C(O)NH$—, $(R^{10})_2NC(O)$—, $R^{10}_2N$—$C(NR^{10})$—, CN, $R^{10}C(O)$—, $N_3$, —$N(R^{10})_2$, or $R^{10}OC(O)NH$—;

provided that when $R^8$ is heterocycle, attachment of $R^8$ to V is through a substitutable ring carbon;

$R^9$ is independently selected from:
a) hydrogen,
b) $C_2$-$C_6$ alkenyl, $C_2$-$C_6$ alkynyl, $C_1$-$C_6$ perfluoroalkyl, F, Cl, Br, $R^{11}O$—, $R^{11}S(O)_m$—, $R^{10}C(O)NR^{10}$—, $(R^{10})_2NC(O)$—, $R^{10}{}_2N$—$C(NR^{10})$—, CN, $NO_2$, $R^{10}C(O)$—, $N_3$, —$N(R^{10})_2$, or $R^{11}OC(O)NR^{10}$—, and
c) $C_1$-$C_6$ alkyl unsubstituted or substituted by $C_1$-$C_6$ perfluoroalkyl, F, Cl, Br, $R^{10}O$—, $R^{11}S(O)_m$—, $R^{10}C(O)NR^{10}$—, $(R^{10})_2NC(O)$—, $R^{10}{}_2N$—$C(NR^{10})$—, CN, $R^{10}C(O)$—, $N_3$, —$N(R^{10})_2$, or $R^{11}OC(O)NR^{10}$—;

$R^{10}$ is independently selected from hydrogen, $C_1$-$C_6$ alkyl, benzyl, 2,2,2-trifluoroethyl and aryl;

$R^{11}$ is independently selected from $C_1$-$C_6$ alkyl and aryl;

$R^{12}$ is independently selected from hydrogen, $C_1$-$C_6$ alkyl, $C_1$-$C_6$ aralkyl, $C_1$-$C_6$ substituted aralkyl, $C_1$-$C_6$ heteroaralkyl, $C_1$-$C_6$ substituted heteroaralkyl, aryl, substituted aryl, heteroaryl, substituted heteroaryl, $C_1$-$C_6$ perfluoroalkyl, 2-aminoethyl and 2,2,2-trifluoroethyl;

$A^1$ and $A^2$ are independently selected from: a bond, —CH=CH—, —C≡C—, —C(O)—, —C(O)NR$^{10}$—, —NR$^{10}$C(O)—, O, —N(R$^{10}$)—, —S(O)$_2$N(R$^{10}$)—, —N(R$^{10}$)S(O)$_2$—, or S(O)$_m$;

V is selected from:
a) hydrogen,
b) heterocycle,
c) aryl,
d) $C_1$-$C_{20}$ alkyl wherein from 0 to 4 carbon atoms are replaced with a heteroatom selected from O, S, and N, and
e) $C_2$-$C_{20}$ alkenyl, provided that V is not hydrogen if $A^1$ is $S(O)_m$ and V is not hydrogen if $A^1$ is a bond, n is 0 and $A^2$ is $S(O)_m$;

provided that when V is heterocycle, attachment of V to $R^8$ and to $A^1$ is through a substitutable ring carbon;

W is a heterocycle;

X is a bond, —CH=CH—, O, —C(=O)—, —C(O)NR$^7$—, —NR$^7$C(O)—, —C(O)O—, —OC(O)—, —C(O)NR$^7$C(O)—, —NR$^7$—, —S(O)$_2$N(R$^{10}$)—, —N(R$^{10}$)S(O)$_2$— or —S(=O)$_m$—, provided that if a is N, then X is not O, —C(O)NR$^7$—, —C(O)O—, —C(O)NR$^7$C(O)—, —S(O)$_2$N(R$^{10}$)—or —NR$^7$—;

m is 0, 1 or 2;

n is independently 0, 1, 2, 3 or 4;

p is independently 0, 1, 2, 3 or 4;

q is 0, 1, 2 or 3;

r is 0 to 5, provided that r is 0 when V is hydrogen; and t is 0 or 1;

or the pharmaceutically acceptable salts thereof.

A preferred embodiment of the compounds of this invention is illustrated by the following formula A:

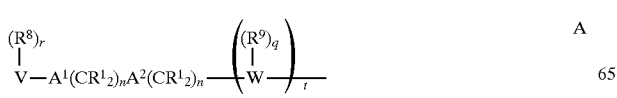

-continued

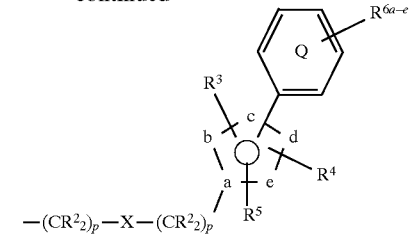

wherein:

a is N or C;

from 0–4 of b, c, d and e are independently N, NH, O and S, and the remaining b, c, d and e atoms are independently CH, provided that if a is C, then at least one of b, c, d or e is independently N, NH, O or S;

$R^1$ is independently selected from: hydrogen, $C_3$-$C_{10}$ cycloalkyl, $R^{10}O$—, —$N(R^{10})_2$, F or $C_1$-$C_6$ alkyl;

$R^2$ is independently selected from:
a) hydrogen,
b) aryl, heterocycle, $C_3$-$C_{10}$ cycloalkyl, $R^{10}O$—, —$N(R^{10})_2$, F or $C_2$-$C_6$ alkenyl,
c) unsubstituted or substituted $C_1$-$C_6$ alkyl wherein the substituent on the substituted $C_1$-$C_6$ alkyl is selected from unsubstituted or substituted aryl, heterocycle, $C_3$-$C_{10}$ cycloalkyl, $C_2$-$C_6$ alkenyl, $R^{10}O$— and —$N(R^{10})_2$;

$R^3$, $R^4$ and $R^5$ are independently selected from:
a) hydrogen,
b) unsubstituted or substituted aryl, unsubstituted or substituted heterocycle, $C_3$-$C_{10}$ cycloalkyl, $C_2$-$C_6$ alkenyl, $C_2$-$C_6$ alkynyl, halogen, $C_1$-$C_6$ perfluoroalkyl, $R^{12}O$—, $R^{11}S(O)_m$—, $R^{10}C(O)NR^{10}$—, $(R^{10})_2NC(O)$—, $R^{10}{}_2N$—$C(NR^{10})$—,CN, $NO_2$, $R^{10}C(O)$—, $N_3$, —$N(R^{10})_2$, or $R^{11}OC(O)NR^{10}$—,
c) unsubstituted $C_1$-$C_6$ alkyl;
d) substituted $C_1$-$C_6$ alkyl wherein the substituent on the substituted $C_1$-$C_6$ alkyl is selected from unsubstituted or substituted aryl, unsubstituted or substituted heterocyclic, $C_3$-$C_{10}$ cycloalkyl, $C_2$-$C_6$ alkenyl, $C_2$-$C_6$ alkynyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $R^{10}C(O)$—, $N_3$, —$N(R^{10})_2$, and $R^{11}OC(O)NR^{10}$—;

$R^{6a}$, $R^{6b}$, $R^{6c}$, $R^{6d}$ and $R^{6e}$ are independently selected from:
a) hydrogen,
b) unsubstituted or substituted aryl, unsubstituted or substituted heterocycle, $C_3$-$C_{10}$ cycloalkyl, $C_2$-$C_6$ alkenyl, $C_2$-$C_6$ alkynyl, halogen, $C_1$-$C_6$ perfluoroalkyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $NO_2$, $R^{10}C(O)$—, $N_3$, —$N(R^{10})_2$, or $R^{11}OC(O)NR^{10}$—,
c) unsubstituted $C_1$-$C_6$ alkyl;
d) substituted $C_1$-$C_6$ alkyl wherein the substituent on the substituted $C_1$-$C_6$ alkyl is selected from unsubstituted or substituted aryl, unsubstituted or substituted heterocyclic, $C_3$-$C_{10}$ cycloalkyl, $C_2$-$C_6$ alkenyl, $C_2$-$C_6$ alkynyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $R^{10}C(O)$—, $N_3$, —$N(R^{10})_2$, and $R^{11}OC(O)NR^{10}$—; or any two of $R^{6a}$, $R^{6b}$, $R^{6c}$, $R^{6d}$ and $R^{6e}$ on adjacent carbon atoms are combined to form a diradical selected from —CH═CH—CH═CH—, —CH═CH—CH$_2$—, —(CH$_2$)$_4$— and —(CH$_2$)$_3$—;

provided that when $R^{6a}$, $R^{6b}$, $R^{6c}$, $R^{6d}$ or $R^{6e}$ is unsubstituted or substituted heterocycle, attachment of $R^{6a}$, $R^{6b}$, $R^{6c}$, $R^{6d}$ or $R^{6e}$ to Q is through a substitutable ring carbon;

$R^7$ is selected from: H; $C_{1-4}$ alkyl, $C_{3-6}$ cycloalkyl, heterocycle, aryl, aroyl, heteroaroyl, arylsulfonyl, heteroarylsulfonyl, unsubstituted or substituted with:
a) $C_{1-4}$ alkoxy,
b) aryl or heterocycle,
c) halogen,
d) HO,
e)

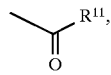

f) —SO$_2$R$^{11}$
g) N(R$^{10}$)$_2$ or
h) $C_{1-4}$ perfluoroalkyl;

$R^8$ is independently selected from:
a) hydrogen,
b) aryl, substituted aryl, heterocycle, $C_1$–$C_6$ alkyl, $C_2$–$C_6$ alkenyl, $C_2$–$C_6$ alkynyl, $C_1$–$C_6$ perfluoroalkyl, F, Cl, R$^{10}$O—, R$^{10}$C(O)NR$^{10}$—, CN, NO$_2$, (R$^{10}$)$_2$N—C(NR$^{10}$)—, R$^{10}$C(O)—, —N(R$^{10}$)$_2$, or R$^{11}$OC(O)NR$^{10}$—, and
c) $C_1$–$C_6$ alkyl substituted by $C_1$–$C_6$ perfluoroalkyl, R$^{10}$O—, R$^{10}$C(O)NR$^{10}$—, (R$^{10}$)$_2$N—C(NR$^{10}$)—, R$^{10}$C(O)—, —N(R$^{10}$)$_2$, or R$^{11}$OC(O)NR$^{10}$—;

provided that when $R^8$ is heterocycle, attachment of $R^8$ to V is through a substitutable ring carbon;

$R^9$ is selected from:
a) hydrogen,
b) $C_2$–$C_6$ alkenyl, $C_2$–$C_6$ alkynyl, $C_1$–$C_6$ perfluoroalkyl, F, Cl, R$^{11}$O—, R$^{11}$S(O)$_m$—, R$^{10}$C(O)NR$^{10}$—, (R$^{10}$)$_2$NC(O)—, CN, NO$_2$, (R$^{10}$)$_2$N—C(NR$^{10}$)—, R$^{10}$C(O)—, —N(R$^{10}$)$_2$, or R$^{11}$OC(O)NR$^{10}$—, and
c) $C_1$–$C_6$ alkyl unsubstituted or substituted by $C_1$–$C_6$ perfluoroalkyl, F, Cl, R$^{10}$O—, R$^{11}$S(O)$_m$—, R$^{10}$C(O)NR$^{10}$—, (R$^{10}$)$_2$NC(O)—, CN, (R$^{10}$)$_2$N—C(NR$^{10}$)—, R$^{10}$C(O)—, —N(R$^{10}$)$_2$, or R$^{11}$OC(O)NR$^{10}$—;

$R^{10}$ is independently selected from hydrogen, $C_1$–$C_6$ alkyl, benzyl, 2,2,2-trifluoroethyl and aryl;

$R^{11}$ is independently selected from $C_1$–$C_6$ alkyl and aryl;

$R^{12}$ is independently selected from hydrogen, $C_1$–$C_6$ alkyl, $C_1$–$C_6$ aralkyl, $C_1$–$C_6$ substituted aralkyl, $C_1$–$C_6$ heteroaralkyl, $C_1$–$C_6$ substituted heteroaralkyl, aryl, substituted aryl, heteroaryl, substituted heteroaryl, $C_1$–$C_6$ perfluoroalkyl, 2-aminoethyl and 2,2,2-trifluoroethyl;

$A^1$ and $A^2$ are independently selected from: a bond, —CH═CH—, —C≡C—, —C(O)—, —C(O)NR$^{10}$—, O, —N(R$^{10}$)—, or S(O)$_m$;

V is selected from:
a) hydrogen,
b) heterocycle selected from pyrrolidinyl, imidazolyl, imidazolinyl, pyridinyl, thiazolyl, oxazolyl, indolyl, quinolinyl, isoquinolinyl, triazolyl and thienyl,
c) aryl,
d) $C_1$–$C_{20}$ alkyl wherein from 0 to 4 carbon atoms are replaced with a heteroatom selected from O, S, and N, and
e) $C_2$–$C_{20}$ alkenyl, and provided that V is not hydrogen if $A^1$ is S(O)$_m$ and V is not hydrogen if $A^1$ is a bond, n is 0 and $A^2$ is S(O)$_m$;

provided that when V is heterocycle, attachment of V to $R^8$ and to $A^1$ is through a substitutable ring carbon;

W is a heterocycle selected from pyrrolidinyl, imidazolyl, imidazolinyl, pyridinyl, thiazolyl, oxazolyl, indolyl, quinolinyl, triazolyl or isoquinolinyl;

X is a bond, O, —C(═O)—, —CH═CH—, —C(O)NR$^7$—, —NR$^7$C(O)—, —NR$^7$—, —S(O)$_2$N(R$^{10}$)—, —N(R$^{10}$)S(O)$_2$— or —S(═O)$_m$—, provided that if a is N, then X is not O, —C(O)NR$^7$—, —S(O)$_2$N(R$^{10}$)— or —NR$^7$—;

m is 0, 1 or 2;

n is independently 0, 1, 2, 3 or 4;

p is independently 0, 1, 2, 3 or 4;

q is 0, 1, 2 or 3;

r is 0 to 5, provided that r is 0 when V is hydrogen; and t is 0 or 1;

or the pharmaceutically acceptable salts thereof.

A preferred embodiment of the compounds of this invention are illustrated by the formula B:

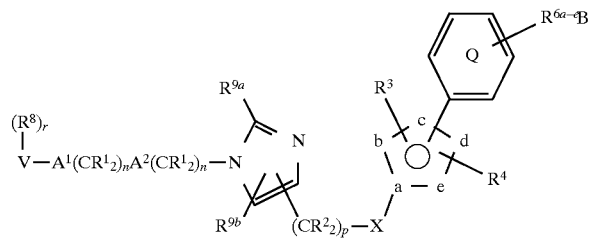

wherein:
a is N or C;

from 0–4 of b, c, d and e are independently N, NH, O and S, and the remaining b, c, d and e atoms are independently CH, provided that if a is C, then at least one of b, c, d or e is independently N, NH, O or S;

$R^1$ is independently selected from: hydrogen, $C_3$–$C_{10}$ cycloalkyl, R$^{10}$O—, —N(R$^{10}$)$_2$, F or $C_1$–$C_6$ alkyl;

$R^2$ is independently selected from:
a) hydrogen,
b) aryl, heterocycle, $C_3$–$C_{10}$ cycloalkyl, R$^{10}$O—, —N(R$^{10}$)$_2$, F or $C_2$–$C_6$ alkenyl,
c) unsubstituted or substituted $C_1$–$C_6$ alkyl wherein the substituent on the substituted $C_1$–$C_6$ alkyl is selected from unsubstituted or substituted aryl, heterocycle, $C_3$–$C_{10}$ cycloalkyl, $C_2$–$C_6$ alkenyl, R$^{10}$O— and —N(R$^{10}$)$_2$;

$R^3$ and $R^4$ are independently selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, R$^{12}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, NO$_2$, R$^{10}$C(O)—, N$_3$, —N(R$^{10}$)$_2$, or R$^{11}$OC(O)NR$^{10}$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, R$^{12}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, R$^{10}$C(O)—, N$_3$, —N(R$^{10}$)$_2$, and R$^{11}$OC(O)NR$^{10}$—;

$R^{6a}$, $R^{6b}$, $R^{6c}$, $R^{6d}$ and $R^{6e}$ are independently selected from:
  a) hydrogen,
  b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $NO_2$, $R^{10}C(O)$—, $N_3$, —$N(R^{10})_2$, or $R^{11}OC(O)NR^{10}$—,
  c) unsubstituted $C_1$–$C_6$ alkyl,
  d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $R^{10}C(O)$—, $N_3$, —$N(R^{10})_2$, and $R^{11}OC(O)NR^{10}$—; or any two of $R^{6a}$, $R^{6b}$, $R^{6c}$, $R^{6d}$ and $R^{6e}$ on adjacent carbon atoms are combined to form a diradical selected from —CH=CH—CH=CH—, —CH=CH—CH$_2$—, —(CH$_2$)$_4$— and —(CH$_2$)$_3$—;

provided that when $R^{6a}$, $R^{6b}$, $R^{6c}$, $R^{6d}$ or $R^{6e}$ is unsubstituted or substituted heterocycle, attachment of $R^{6a}$, $R^{6b}$, $R^{6c}$, $R^{6d}$ or $R^{6e}$ to Q is through a substitutable ring carbon;

c) aryl,
  d) $C_1$–$C_{20}$ alkyl wherein from 0 to 4 carbon atoms are replaced with a heteroatom selected from O, S, and N, and
  e) $C_2$–$C_{20}$ alkenyl, and provided that V is not hydrogen if $A^1$ is $S(O)_m$ and V is not hydrogen if $A^1$ is a bond, n is 0 and $A^2$ is $S(O)_m$;

provided that when V is heterocycle, attachment of V to $R^8$ and to $A^1$ is through a substitutable ring carbon;

X is a bond, —CH=CH—, —C(O)NR$^{10}$—, —NR$^{10}$C(O)—, —NR$^{10}$—, O or —C(=O)—;

provided that if a is N, then X is not —C(O)NR$^{10}$—, —NR$^{10}$— or O;

m is 0, 1 or 2;

n is independently 0, 1, 2, 3 or 4;

p is 0, 1, 2, 3 or 4; and r is 0 to 5, provided that r is 0 when V is hydrogen;

or the pharmaceutically acceptable salts thereof.

Another preferred embodiment of the compounds of this invention are illustrated by the formula C:

wherein:
  a is N or C;
  from 0–4 of b, c, d and e are independently N, NH, O and S, and the remaining b, c, d and e atoms are independently CH, provided that if a is C, then at least one of b, c, d or e is independently N, NH, O or S;
  $R^1$ is independently selected from: hydrogen, $C_3$–$C_{10}$ cycloalkyl, $R^{10}O$—, —$N(R^{10})_2$, F or $C_1$–$C_6$ alkyl;
  $R^2$ is independently selected from:
    a) hydrogen,
    b) aryl, heterocycle, $C_3$–$C_{10}$ cycloalkyl, $R^{10}O$—, —$N(R^{10})_2$, F or $C_2$–$C_6$ alkenyl,
    c) unsubstituted or substituted $C_1$–$C_6$ alkyl wherein the substituent on the substituted $C_1$–$C_6$ alkyl is selected from unsubstituted or substituted aryl, heterocycle, $C_3$–$C_{10}$ cycloalkyl, $C_2$–$C_6$ alkenyl, $R^{10}O$— and —$N(R^{10})_2$;
  $R^3$ and $R^4$ are independently selected from:
    a) hydrogen,
    b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $CN(R^{10})_2NC(O)$—, $R^{10}{}_2N$—$C(NR^{10})$—, CN, $NO_2$, $R^{10}C(O)$—, $N_3$, —$N(R^{10})_2$, or $R^{11}OC(O)NR^{10}$—,
    c) unsubstituted $C_1$–$C_6$ alkyl,
    d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ $R^8$ is independently selected from:
  a) hydrogen,
  b) aryl, substituted aryl, heterocycle, $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, —$N(R^{10})_2$, or $R^{11}OC(O)NR^{10}$—, and
  c) $C_1$–$C_6$ alkyl substituted by $C_1$–$C_6$ perfluoroalkyl, $R^{10}O$—, $R^{10}C(O)NR^{10}$—, $(R^{10})_2N$—$C(NR^{10})$—, $R^{10}C(O)$—, —$N(R^{10})_2$, or $R^{11}OC(O)NR^{10}$—;

provided that when $R^8$ is heterocycle, attachment of $R^8$ to V is through a substitutable ring carbon;

$R^{9a}$ and $R^{9b}$ are independently hydrogen, $C_1$–$C_6$ alkyl, trifluoromethyl and halogen;

$R^{10}$ is independently selected from hydrogen, $C_1$–$C_6$ alkyl, benzyl, 2,2,2-trifluoroethyl and aryl;

$R^{11}$ is independently selected from $C_1$–$C_6$ alkyl and aryl;

$R^{12}$ is independently selected from hydrogen, $C_1$–$C_6$ alkyl, $C_1$–$C_6$ aralkyl, $C_1$–$C_6$ substituted aralkyl, $C_1$–$C_6$ heteroaralkyl, $C_1$–$C_6$ substituted heteroaralkyl, aryl, substituted aryl, heteroaryl, substituted heteroaryl, $C_1$–$C_6$ perfluoroalkyl, 2-aminoethyl and 2,2,2-trifluoroethyl;

$A^1$ and $A^2$ are independently selected from: a bond, —CH=CH—, —C≡C—, —C(O)—, —C(O)NR$^{10}$—, O, —N(R$^{10}$)—, or $S(O)_m$;

V is selected from:
  a) hydrogen,
  b) heterocycle selected from pyrrolidinyl, imidazolyl, imidazolinyl, pyridinyl, thiazolyl, oxazolyl, indolyl, quinolinyl, isoquinolinyl, triazolyl and thienyl, alkenyl, $C_2$–$C_6$ alkynyl, $R^{12}O$—, $R^{11}S(O)_m$—, $R^{10}C(O)NR^{10}$—, $(R^{10})_2NC(O)$—, $R^{10}_2N$—$C(NR^{10})$—, CN, $R^{10}C(O)$—, $N_3$, —$N(R^{10})_2$, and $R^{11}OC(O)NR^{10}$—;

$R^{6a}$, $R^{6b}$, $R^{6c}$, $R^{6d}$ and $R^{6e}$ are independently selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)R^{10}$—, $CN(R^{10})_2NC(O)$—, $R^{10}_2N$—$C(NR^{10})$—, CN, $NO_2$, $R^{10}C(O)$—, $N_3$, —$N(R^{10})_2$, or $R^{11}OC(O)NR^{10}$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{10}_2N$—$C(NR^{10})$—, CN, $R^{10}C(O)$—, $N_3$, —$N(R^{10})_2$, and $R^{11}OC(O)NR^{10}$—;

provided that when $R^{6a}$, $R^{6b}$, $R^{6c}$, $R^{6d}$ or $R^{6e}$ is unsubstituted or substituted heterocycle, attachment of $R^{6a}$, $R^{6b}$, $R^6c$, $R^{6d}$ or $R^{6e}$ to Q is through a substitutable ring carbon;

$R^8$ is independently selected from:
a) hydrogen,
b) aryl, substituted aryl, heterocycle, $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}OC(O)NR^{10}$—, CN, $NO_2$, $(R^{10})_2N$—$C(NR^{10})$—, $R^{10}C(O)$—, —$N(R^{10})_2$, or $R^{11}OC(O)NR^{10}$—, and
c) $C_1$–$C_6$ alkyl substituted by $C_1$–$C_6$ perfluoroalkyl, $R^{10}O$—, $R^{10}OC(O)NR^{10}$—, $(R^{10})_2N$—$C(NR^{10})$, $R^{10}C(O)$—, —$N(R^{10})_2$, or $R^{11}OC(O)NR^{10}$—;

provided that when $R^8$ is heterocycle, attachment of $R^8$ to V is through a substitutable ring carbon;

$R^{9a}$ and $R^{9b}$ are independently hydrogen, $C_1$–$C_6$ alkyl, trifluoromethyl and halogen;

$R^{10}$ is independently selected from hydrogen, $C_1$–$C_6$ alkyl, benzyl, 2,2,2-trifluoroethyl and aryl;

$R^{11}$ is independently selected from $C_1$–$C_6$ alkyl and aryl;

$R^{12}$ is independently selected from hydrogen, $C_1$–$C_6$ alkyl, $C_1$–$C_6$ aralkyl, $C_1$–$C_6$ substituted aralkyl, $C_1$–$C_6$ heteroaralkyl, $C_1$–$C_6$ substituted heteroaralkyl, aryl, substituted aryl, heteroaryl, substituted heteroaryl, $C_1$–$C_6$ perfluoroalkyl, 2-aminoethyl and 2,2,2-trifluoroethyl;

$A^1$ and $A^2$ are independently selected from: a bond, —CH=CH—, —C≡C—, —C(O)—, —C(O)NR$^{10}$—, O, —N(R$^{10}$)—, or $S(O)_m$;

V is selected from:
a) hydrogen,
b) heterocycle selected from pyrrolidinyl, imidazolyl, imidazolinyl, pyridinyl, thiazolyl, oxazolyl, indolyl, quinolinyl, isoquinolinyl, triazolyl and thienyl,
c) aryl,
d) $C_1$–$C_{20}$ alkyl wherein from 0 to 4 carbon atoms are replaced with a heteroatom selected from O, S, and N, and
e) $C_2$–$C_{20}$ alkenyl, and provided that V is not hydrogen if $A^1$ is $S(O)_m$ and V is not hydrogen if $A^1$ is a bond, n is 0 and $A^2$ is $S(O)_m$;

provided that when V is heterocycle, attachment of V to $R^8$ and to $A^1$ is through a substitutable ring carbon;

X is a bond, —CH=CH—, —C(O)NR$^{10}$—, —NR$^{10}$C(O)—, —NR$^{10}$—, O or —C(=O)—;

provided that if a is N, then X is not —C(O)NR$^{10}$—, —NR$^{10}$— or O;

m is 0, 1 or 2;

n is independently 0, 1, 2, 3 or 4;

p is 0, 1, 2, 3 or 4, provided that p is not 0 if X is a bond, —NR$^{10}$— or O; and r is 0 to 5, provided that r is 0 when V is hydrogen;

or the pharmaceutically acceptable salts thereof.

In a more preferred embodiment of this invention, the inhibitors of farnesyl-protein transferase are illustrated by the formula D:

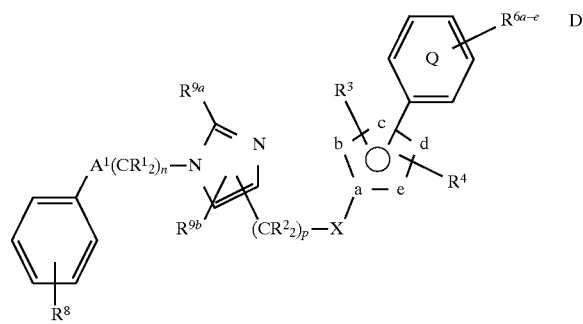

wherein:
a is N or C;
from 0–4 of b, c, d and e are independently N, NH, O and S, and the remaining b, c, d and e atoms are independently CH, provided that if a is C, then at least one of b, c, d or e is independently N, NH, O or S;

$R^1$ is independently selected from: hydrogen, $C_3$–$C_{10}$ cycloalkyl or $C_1$–$C_6$ alkyl;

$R^2$ is independently selected from:
a) hydrogen,
b) aryl, heterocycle, $C_3$–$C_{10}$ cycloalkyl, $R^{10}O$—, —$N(R^{10})_2$, F or $C_2$–$C_6$ alkenyl,
c) $C_1$–$C_6$ alkyl unsubstituted or substituted by aryl, heterocycle, $C_3$–$C_{10}$ cycloalkyl, $C_2$–$C_6$ alkenyl, $R^{10}O$—, or —$N(R^{10})_2$;

$R^3$ is selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $R^{10}_2N$—$C(NR^{10})$—, CN, $NO_2$, $R^{10}C(O)$—, $N_3$, —$N(R^{10})_2$, or $R^{11}OC(O)NR^{10}$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{10}_2N$—$C(NR^{10})$—, CN, $R^{10}C(O)$—, $N_3$, —$N(R^{10})_2$, and $R^{11}OC(O)NR^{10}$—;

$R^4$ is selected from H, halogen, $C_1$–$C_6$ alkyl and $CF_3$;

$R^{6a}$, $R^{6b}$, $R^{6c}$, $R^{6d}$ and $R^{6e}$ are independently selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $NO_2$, $R^{10}C(O)$—, $N_3$, —$N(R^{10})_2$, or $R^{11}OC(O)NR^{10}$—, c) unsubstituted $C_1$–$C_6$ alkyl, d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $R^{10}C(O)$—, $N_3$, —$N(R^{10})_2$, and $R^{11}OC(O)NR^{10}$—, or any two of $R^{6a}$, $R^{6b}$, $R^{6c}$, $R^{6d}$ and $R^{6e}$ on adjacent carbon atoms are combined to form a diradical selected from —CH=CH—CH=CH—, —CH=CH—CH$_2$—, —(CH$_2$)$_4$— and —(CH$_2$)$_3$—;

provided that when $R^{6a}$, $R^{6b}$, $R^{6c}$, $R^{6d}$ or $R^{6e}$ is unsubstituted or substituted heterocycle, attachment of $R^{6a}$, $R^{6b}$, $R^{6c}$, $R^{6d}$ or $R^{6e}$ to Q is through a substitutable ring carbon;

$R^8$ is independently selected from:
a) hydrogen,
b) aryl, substituted aryl, heterocycle, $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, —$N(R^{10})_2$, or $R^{11}OC(O)NR^{10}$—, and
c) $C_1$–$C_6$ alkyl substituted by $C_1$–$C_6$ perfluoroalkyl, $R^{10}O$—, $R^{10}C(O)NR^{10}$—, $(R^{10})_2N$—$C(NR^{10})$—, $R^{10}C(O)$—, —$N(R^{10})_2$, or $R^{11}OC(O)NR^{10}$—;

provided that when $R^8$ is heterocycle, attachment of $R^8$ to V is through a substitutable ring carbon;

$R^{9a}$ and $R^{9b}$ are independently hydrogen, halogen, $CF_3$ or methyl;

$R^{10}$ is independently selected from hydrogen, $C_1$–$C_6$ alkyl, benzyl, 2,2,2-trifluoroethyl and aryl;

$R^{11}$ is independently selected from $C_1$–$C_6$ alkyl and aryl;

$R^{12}$ is independently selected from hydrogen, $C_1$–$C_6$ alkyl, $C_1$–$C_6$ aralkyl, $C_1$–$C_6$ substituted aralkyl, $C_1$–$C_6$ heteroaralkyl, $C_1$–$C_6$ substituted heteroaralkyl, aryl, substituted aryl, heteroaryl, substituted heteroaryl, $C_1$–$C_6$ perfluoroalkyl, 2-aminoethyl and 2,2,2-trifluoroethyl;

$A^1$ is selected from: a bond, —C(O)—, O, —N($R^{10}$)—, or $S(O)_m$;

X is a bond, —CH=CH—, —C(O)NR$^{10}$—, —NR$^{10}$C(O)—, —NR$^{10}$—, O or —C(=O)—, provided that if a is N, then X is not —C(O)NR$^{10}$—, —NR$^{10}$— or O;

n is 0 or 1; provided n is not 0 if $A^1$ is a bond, O, —N($R^{10}$)—, or $S(O)_m$;

m is 0, 1 or 2; and p is 0, 1, 2, 3 or 4;

or the pharmaceutically acceptable salts thereof.

In another more preferred embodiment of this invention, the inhibitors of farnesyl-protein transferase are illustrated by the formula E:

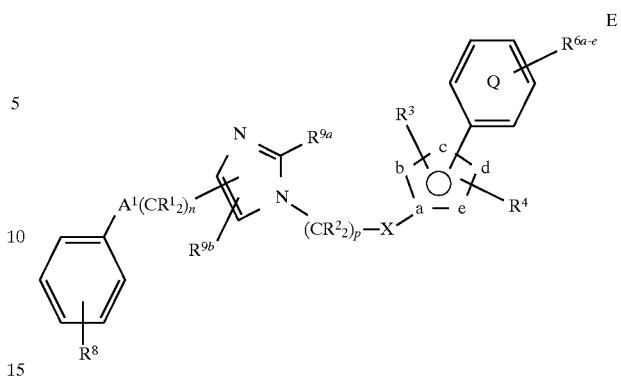

wherein:

a is N or C;

from 0–4 of b, c, d and e are independently N, NH, O and S, and the remaining b, c, d and e atoms are independently CH, provided that if a is C, then at least one of b, c, d or e is independently N, NH, O or S;

$R^1$ is independently selected from: hydrogen, $R^{10}O$—, —$N(R^{10})_2$, F, $C_3$–$C_{10}$ cycloalkyl or $C_1$–$C_6$ alkyl;

$R^2$ is independently selected from:
a) hydrogen,
b) aryl, heterocycle, $C_3$–$C_{10}$ cycloalkyl, $R^{10}O$—, —$N(R^{10})_2$, F or $C_2$–$C_6$ alkenyl,
c) $C_1$–$C_6$ alkyl unsubstituted or substituted by aryl, heterocycle, $C_3$–$C_{10}$ cycloalkyl, $C_2$–$C_6$ alkenyl, $R^{10}O$—, or —$N(R^{10})_2$;

$R^3$ is selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $NO_2$, $R^{10}C(O)$—, $N_3$, —$N(R^{10})_2$, or $R^{11}OC(O)NR^{10}$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $R^{10}C(O)$—, $N_3$, —$N(R^{10})_2$, and $R^{11}OC(O)NR^{10}$—;

$R^4$ is selected from H, halogen, $C_1$–$C_6$ alkyl and $CF_3$;

$R^{6a}$, $R^{6b}$, $R^{6c}$, $R^{6d}$ and $R^{6e}$ are independently selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $NO_2$, $R^{10}C(O)$—, $N_3$, —$N(R^{10})_2$, or $R^{11}OC(O)NR^{10}$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $R^{10}C(O)$—, $N_3$, —$N(R^{10})_2$, and $R^{11}OC(O)NR^{10}$—;

provided that when $R^{6a}$, $R^{6b}$, $R^{6c}$, $R^{6d}$ or $R^{6e}$ is unsubstituted or substituted heterocycle, attachment of $R^{6a}$, $R^{6b}$, $R^{6c}$, $R^{6d}$ or $R^{6e}$ to Q is through a substitutable ring carbon;

$R^8$ is independently selected from:
a) hydrogen,
b) aryl, substituted aryl, heterocycle, $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, —$N(R^{10})_2$, or $R^{11}OC(O)NR^{10}$—, and
c) $C_1$–$C_6$ alkyl substituted by $C_1$–$C_6$ perfluoroalkyl, $R^{10}O$—, $R^{10}C(O)NR^{10}$—, $(R^{10})_2N$—$C(NR^{10})$—, $R^{10}C(O)$—, —$N(R^{10})_2$, or $R^{11}OC(O)NR^{10}$—;

provided that when $R^8$ is heterocycle, attachment of $R^8$ to V is through a substitutable ring carbon;

$R^{9a}$ and $R^{9b}$ are independently hydrogen, halogen, $CF_3$ or methyl;

$R^{10}$ is independently selected from hydrogen, $C_1$–$C_6$ alkyl, benzyl, 2,2,2-trifluoroethyl and aryl;

$R^{11}$ is independently selected from $C_1$–$C_6$ alkyl and aryl;

$R^{12}$ is independently selected from hydrogen, $C_1$–$C_6$ alkyl, $C_1$–$C_6$ aralkyl, $C_1$–$C_6$ substituted aralkyl, $C_1$–$C_6$ heteroaralkyl, $C_1$–$C_6$ substituted heteroaralkyl, aryl, substituted aryl, heteroaryl, substituted heteroaryl, $C_1$–$C_6$ perfluoroalkyl, 2-aminoethyl and 2,2,2-trifluoroethyl;

X is a bond, —CH=CH—, —C(O)$NR^{10}$—, —$NR^{10}$C(O)—, —$NR^{10}$—, O or —C(=O)—;

provided that if a is N, then X is not —C(O)$NR^{10}$—, —$NR^{10}$— or O;

n is 0 or 1;

m is 0, 1 or 2; and p is 0, 1, 2, 3 or 4, provided that p is not 0 if X is a bond, —$NR^{10}$C(O)—, —$NR^{10}$— or O;

or the pharmaceutically acceptable salts thereof.

In a further embodiment of this invention, the inhibitors of farnesyl-protein transferase are illustrated by the formula F:

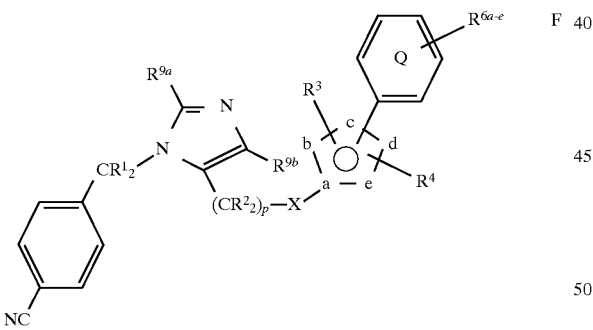

F wherein:
a is N or C;
from 0–4 of b, c, d and e are independently N, NH, O and S, and the remaining b, c, d and e atoms are independently CH, provided that if a is C, then at least one of b, c, d or e is independently N, NH, O or S;

$R^1$ is independently selected from: hydrogen, $C_3$–$C_{10}$ cycloalkyl or $C_1$–$C_6$ alkyl;

$R^2$ is independently selected from:
a) hydrogen,
b) aryl, heterocycle, $C_3$–$C_{10}$ cycloalkyl, $R^{10}O$—, —$N(R^{10})_2$ or F,
c) $C_1$–$C_6$ alkyl unsubstituted or substituted by aryl, heterocycle, $C_3$–$C_{10}$ cycloalkyl, $R^{10}O$—, or —$N(R^{10})_2$;

$R^3$ is selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $NO_2$, $R^{10}C(O)$—, $N_3$, —$N(R^{10})_2$, or $R^{11}OC(O)NR^{10}$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $R^{10}C(O)$—, $N_3$, —$N(R^{10})_2$, and $R^{11}OC(O)NR^{10}$—;

$R^4$ is selected from H, halogen, $CH_3$ and $CF_3$;

$R^{6a}$, $R^{6b}$, $R^{6c}$, $R^{6d}$ and $R^{6e}$ are independently selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $NO_2$, $R^{10}C(O)$—, $N_3$, —$N(R^{10})_2$, or $R^{11}OC(O)NR^{10}$—,
c) unsubstituted $C_1$–$C_6$ alkyl,
d) substituted C 1–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $R^{10}C(O)$—, $N_3$, —$N(R^{10})_2$, and $R^{11}OC(O)NR^{10}$—; or any two of $R^{6a}$, $R^{6b}$, $R^{6c}$, $R^{6d}$ and $R^{6e}$ on adjacent carbon atoms are combined to form a diradical selected from —CH=CH—CH=CH—, —CH=CH—$CH_2$—, —$(CH_2)_4$— and —$(CH_2)_3$—;

provided that when $R^{6a}$, $R^{6b}$, $R^{6c}$, $R^{6d}$ or $R^{6e}$ is unsubstituted or substituted heterocycle, attachment of $R^{6a}$, $R^{6b}$, $R^{6c}$, $R^{6d}$ or $R^{6e}$ to Q is through a substitutable ring carbon;

$R^{9a}$ and $R^{9b}$ are independently hydrogen, halogen, $CF_3$ or methyl;

$R^{10}$ is independently selected from hydrogen, $C_1$–$C_6$ alkyl, benzyl, 2,2,2-trifluoroethyl and aryl;

$R^{11}$ is independently selected from $C_1$–$C_6$ alkyl and aryl;

$R^{12}$ is independently selected from hydrogen, $C_1$–$C_6$ alkyl, $C_1$–$C_6$ aralkyl, $C_1$–$C_6$ substituted aralkyl, $C_1$–$C_6$ heteroaralkyl, $C_1$–$C_6$ substituted heteroaralkyl, aryl, substituted aryl, heteroaryl, substituted heteroaryl, $C_1$–$C_6$ perfluoroalkyl, 2-aminoethyl and 2,2,2-trifluoroethyl;

X is a bond, —CH=CH—, —C(O)$NR^{10}$—, —$NR^{10}$C(O)—, O or —C(=O)—; provided that if a is N, then X is not —C(O)$NR^{10}$— or O;

m is 0, 1 or 2; and p is 0, 1, 2, 3 or 4;

or the pharmaceutically acceptable salts thereof.

In a further embodiment of this invention, the inhibitors of farnesyl-protein transferase are illustrated by the formula G:

wherein:

a is C;

from 0–4 of b, c, d and e are independently N, NH, O and S, and the remaining b, c, d and e atoms are independently CH, provided that at least one of b, c, d or e is independently N, NH, O or S;

$R^1$ is independently selected from: hydrogen, $R^{10}O$—, —$N(R^{10})_2$, F, $C_3$–$C_{10}$ cycloalkyl or $C_1$–$C_6$ alkyl;

$R^2$ is independently selected from:
 a) hydrogen,
 b) aryl, heterocycle or $C_3$–$C_{10}$ cycloalkyl,
 c) $C_1$–$C_6$ alkyl unsubstituted or substituted by aryl, heterocycle, $C_3$–$C_{10}$ cycloalkyl, $C_2$–$C_6$ alkenyl, $R^{10}O$—, or —$N(R^{10})_2$;

$R^3$ is selected from:
 a) hydrogen,
 b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $NO_2$, $R^{10}C(O)$—, $N_3$, —$N(R^{10})_2$, or $R^{11}OC(O)NR^{10}$—,
 c) unsubstituted $C_1$–$C_6$ alkyl,
 d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $R^{10}C(O)$—, $N_3$, —$N(R^{10})_2$, and $R^{11}OC(O)NR^{10}$—;

$R^4$ is selected from H, halogen, $CH_3$ and $CF_3$;

$R^{6a}$, $R^{6b}$, $R^{6c}$, $R^{6d}$ and $R^{6e}$ are independently selected from:
 a) hydrogen,
 b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $NO_2$, $R^{10}C(O)$—, $N_3$, —$N(R^{10})_2$, or $R^{11}OC(O)NR^{10}$—,
 c) unsubstituted $C_1$–$C_6$ alkyl,
 d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{10}{}_2N$—$C(NR^{10})$—, CN, $R^{10}C(O)$—, $N_3$, —$N(R^{10})_2$, and $R^{11}OC(O)NR^{10}$—; or any two of $R^{6a}$, $R^{6b}$, $R^{6c}$, $R^{6d}$ and $R^{6e}$ on adjacent carbon atoms are combined to form a diradical selected from —CH=CH—CH=CH—, —CH=CH—CH$_2$—, —(CH$_2$)$_4$— and —(CH$_2$)$_3$—;

provided that when $R^{6a}$, $R^{6b}$, $R^{6c}$, $R^{6d}$ or $R^{6e}$ is unsubstituted or substituted heterocycle, attachment of $R^{6a}$, $R^{6b}$, $R^{6c}$, $R^{6d}$ or $R^{6e}$ to Q is through a substitutable ring carbon;

$R^{9a}$ and $R^{9b}$ are independently hydrogen, halogen, $CF_3$ or methyl;

$R^{10}$ is independently selected from hydrogen, $C_1$–$C_6$ alkyl, benzyl, 2,2,2-trifluoroethyl and aryl;

$R^{11}$ is independently selected from $C_1$–$C_6$ alkyl and aryl;

$R^{12}$ is independently selected from hydrogen, $C_1$–$C_6$ alkyl, $C_1$–$C_6$ aralkyl, $C_1$–$C_6$ substituted aralkyl, $C_1$–$C_6$ heteroaralkyl, $C_1$–$C_6$ substituted heteroaralkyl, aryl, substituted aryl, heteroaryl, substituted heteroaryl, $C_1$–$C_6$ perfluoroalkyl, 2-aminoethyl and 2,2,2-trifluoroethyl;

$A^1$ is selected from: a bond, —C(O)—, O, —$N(R^{10})$—, or $S(O)_m$;

m is 0, 1 or 2; and n is 0 or 1;

or the pharmaceutically acceptable salts thereof.

The preferred compounds of this invention are as follows:

1-{[1-(4-Cyanobenzyl)-1H-imidazol-5-yl]ethyl}-4-phenyl-imidazole

1-{1-(4-Cyanobenzyl)-1H-imidazol-5-yl)methyl}-4-phenylimidazole

1-{1-(4-Cyanobenzyl)-1H-imidazol-5-yl)methyl}-4-(2-methyl)phenyl imidazole 1-(3-Phenyl-5-isoxazolylmethyl)-5-(4-cyanobenzyl) imidazole 1-(3-Phenyl-isoxazol-5-ylacetyl)-5-(4-cyanobenzyl) imidazole 1-(4-Cyanobenzyl)-5-(4-Phenyl-thiazol-2-ylmethyl) imidazole 1-(4-Cyanobenzyl)-5-(4-(2-methylphenyl)-thiazol-2-ylmethyl)imidazole 1-(4-Cyanobenzyl)-5-(4-(3-chlorophenyl)-thiazol-2-ylmethyl)imidazole 1-(4-Cyanobenzyl)-5-(4-(naphth-2-yl)-thiazol-2-ylmethyl) imidazole 1-((4-(2-methylphenyl)-5-methylthiazole-2-ylmethyl)-5-(4-cyanobenzyl) imidazole 1-((4-(2-methylphenyl)thiazole-2-ylethyl)-5-(4-cyanobenzyl) imidazole or the pharmaceutically acceptable salts or optical isomers thereof.

Specific examples of the compounds of the invention are:

1-{1-(4-Cyanobenzyl)-1H-imidazol-5-yl)methyl}-4-phenylimidazole 1-(3-Phenyl-5-isoxazolylmethyl)-5-(4-cyanobenzyl) imidazole

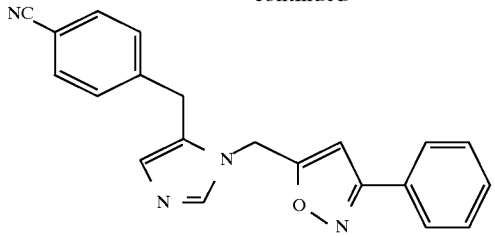

1-(4-Cyanobenzyl)-5-(4-(2-methylphenyl)-thiazol-2-ylmethyl)imidazole

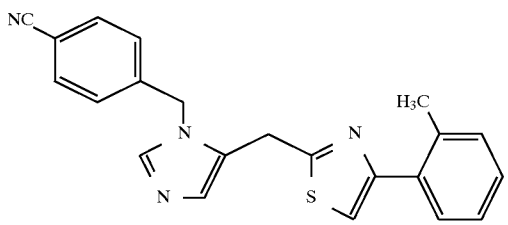

1-((4-(2-methylphenyl)thiazole-2-ylethyl)-5-(4-cyanobenzyl)imidazole

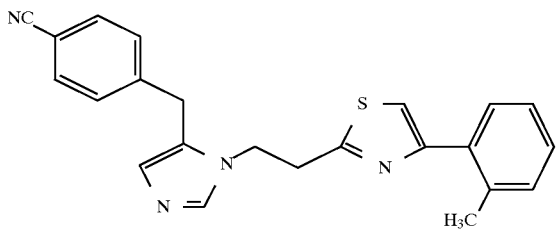

or the pharmaceutically acceptable salts thereof.

The compounds of the present invention may have asymmetric centers and occur as racemates, racemic mixtures, and as individual diastereomers, with all possible isomers, including optical isomers, being included in the present invention. Also, combinations of substituents/or variables are permissible only if such combinations result in stable compounds.

As used herein, "alkyl" and the alkyl portion of aralkyl and similar terms, is intended to include both branched and straight-chain saturated aliphatic hydrocarbon groups having the specified number of carbon atoms; "alkoxy" represents an alkyl group of indicated number of carbon atoms attached through an oxygen bridge.

As used herein, "cycloalkyl" is intended to include non-aromatic cyclic hydrocarbon groups having the specified number of carbon atoms. Examples of cycloalkyl groups include cyclopropyl, cyclobutyl, cyclopentyl, cyclohexyl and the like.

"Alkenyl" groups include those groups having the specified number of carbon atoms and having one or several double bonds. Examples of alkenyl groups include vinyl, allyl, isopropenyl, pentenyl, hexenyl, heptenyl, cyclopropenyl, cyclobutenyl, cyclopentenyl, cyclohexenyl, 1-propenyl, 2-butenyl, 2-methyl-2-butenyl, isoprenyl, farnesyl, geranyl, geranylgeranyl and the like.

"Alkynyl" groups include those groups having the specified number of carbon atoms and having one triple bonds. Examples of alkynyl groups include acetylene, 2-butynyl, 2-pentynyl, 3-pentynyl and the like.

"Halogen" or "halo" as used herein means fluoro, chloro, bromo and iodo.

As used herein, "aryl," and the aryl portion of aroyl and aralkyl, is intended to mean any stable monocyclic or bicyclic carbon ring of up to 7 members in each ring, wherein at least one ring is aromatic. Examples of such aryl elements include phenyl, naphthyl, tetrahydronaphthyl, indanyl, biphenyl, phenanthryl, anthryl or acenaphthyl.

The term heterocycle or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopyrrolidinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, and thienyl.

As used herein, "heteroaryl" is intended to mean any stable monocyclic or bicyclic carbon ring of up to 7 members in each ring, wherein at least one ring is aromatic and wherein from one to four carbon atoms are replaced by heteroatoms selected from the group consisting of N, O, and S. Examples of such heterocyclic elements include, but are not limited to, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolyl, indolinyl, indolyl, isochromanyl, isoindolinyl, isoquinolinyl, isothiazolyl, naphthyridinyl, oxadiazolyl, pyridyl, pyrazinyl, pyrazolyl, pyridazinyl, pyrimidinyl, pyrrolyl, quinazolinyl, quinolinyl, quinoxalinyl, tetrahydroisoquinolinyl, tetrahydroquinolinyl, thiazolyl, thienofuryl, thienothienyl, and thienyl.

As used herein in the definition of $R^3$, $R^4$, $R^5$ and $R^{6a-e}$, the term "the substituted group" intended to mean a substituted $C_{1-8}$ alkyl, substituted $C_{2-8}$ alkenyl, substituted $C_{2-8}$ alkynyl, substituted aryl or substituted heterocycle from which the substituent(s) $R^3$, $R^4$, $R^5$ and $R^{6a-e}$ are selected.

As used herein in the definition of $R^7$, the substituted $C_{1-8}$ alkyl, substituted $C_{3-6}$ cycloalkyl, substituted aroyl, substituted aryl, substituted heteroaroyl, substituted arylsulfonyl, substituted heteroaryl-sulfonyl and substituted heterocycle include moieties containing from 1 to 3 substituents in addition to the point of attachment to the rest of the compound.

As used herein, when no specific substituents are set forth, the terms "substituted aryl", "substituted heterocycle" and "substituted cycloalkyl" are intended to include the cyclic group which is substituted on a substitutable ring carbon atom with 1 or 2 substitutents selected from the group which includes but is not limited to F, Cl, Br, $CF_3$, $NH_2$, $N(C_1-C_6$ alkyl$)_2$, $NO_2$, CN, $(C_1-C_6$ alkyl$)$O—, —OH, $(C_1-C_6$ alkyl$)$ S(O)$_m$—, $(C_1-C_6$ alkyl$)$C(O)NH—, $H_2$N—C(NH)—, $(C_1-C_6$ alkyl$)$C(O)—, $(C_1-C_6$ alkyl$)$OC(O)—, $N_3$,$(C_1-C_6$ alkyl)OC(O)NH—, phenyl, pyridyl, imidazolyl, oxazolyl, isoxazolyl, thiazolyl, thienyl, furyl, isothiazolyl and $C_1$–$C_{20}$ alkyl.

The moiety designated by the following structure

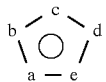

represents an aromatic 5-membered heterocyclic ring and includes the following ring systems:

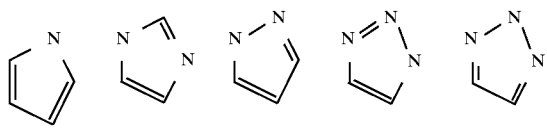

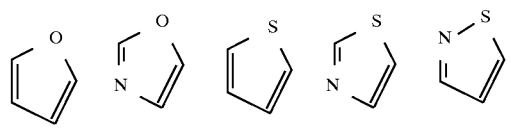

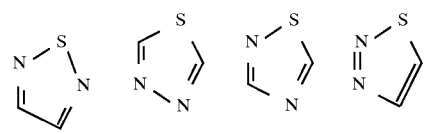

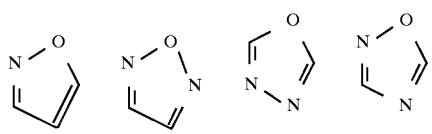

Preferably the aromatic 5-membered heterocyclic ring is selected from:

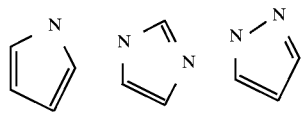

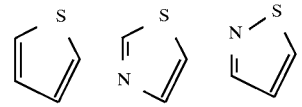

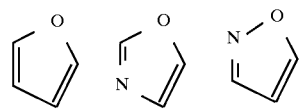

Lines drawn into the ring systems from substituents (such as from $R^3$, $R^4$, Q etc.) means that the indicated bond may be attached to any of the substitutable ring carbon or nitrogen atoms.

The substituent illustrated by the structure

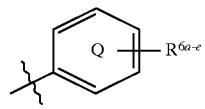

is a simplified representation of a phenyl ring having five (5) substituents (hydrogens and/or non-hydrogens) and may also be represented by the structure

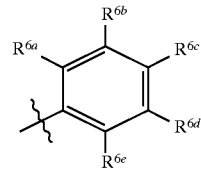

The moiety described as

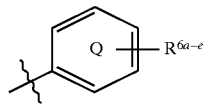

where any two of $R^{6a}$, $R^{6b}$, $R^{6c}$, $R^{6d}$ and $R^{6e}$ on adjacent carbon atoms are combined to form a diradical selected from —CH=CH—CH=CH, —CH=CH—CH—, —(CH$_2$)$_4$— and —(CH$_2$)$_4$— includes the following structures:

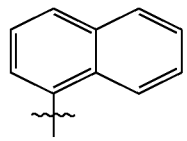

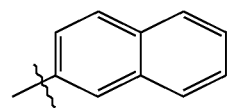

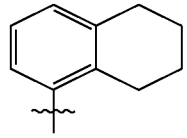

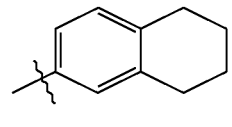

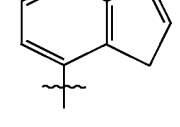

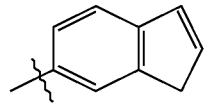

-continued

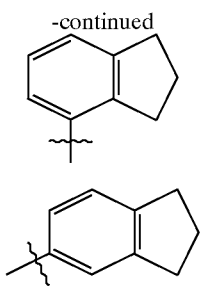

It is understood that such fused ring moieties may be further substituted by the remaining $R^{6a}$, $R^{6b}$, $R^{6c}$, $R^{6d}$ and/or $R^{6e}$ as defined hereinabove.

Preferably, $R^1$ and $R^2$ are independently selected from: hydrogen, $R^{11}C(O)O$—, —$N(R^{10})_2$, $R^{10}C(O)NR^{10}$—, $R^{10}$— or unsubstituted or substituted $C_1$–$C_6$ alkyl wherein the substituent on the substituted $C_1$–$C_6$ alkyl is selected from unsubstituted or substituted phenyl, —$N(R^{10})_2$, $R^{10}O$— and $R^{10}C(O)NR^{10}$—.

Preferably, $R^3$ is selected from:
a) hydrogen,
b) $C_3$–$C_{10}$ cycloalkyl, halogen, $C_1$–$C_6$ perfluoroalkyl, $R^{12}O$—, CN, NO$_2$, $R^{10}C(O)$—or —$N(R^{10})_2$,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{10}{}_2N$—C($NR^{10}$)—, CN, $R^{10}C(O)$—, $N_3$, —$N(R^{10})_2$, and $R^{11}OC(O)$—$NR^{10}$—.

Preferably, $R^4$ is selected from: hydrogen, halogen, trifluoromethyl, trifluoromethoxy and $C_1$–$C_6$ alkyl.

Preferably, $R^5$ is hydrogen.

Preferably, $R^{6a}$, $R^{6b}$, $R^{6c}$, $R^{6d}$ and $R^{6e}$ are independently selected from:
a) hydrogen,
b) $C_3$–$C_{10}$ cycloalkyl, halogen, $C_1$–$C_6$ perfluoroalkyl, $R^{12}O$—, $R^{11}S(O)_m$—, CN, NO$_2$, $R^{10}C(O)$— or —$N(R^{10})_2$,
c) unsubstituted $C_1$–$C_6$ alkyl;
d) substituted $C_1$–$C_6$ alkyl wherein the substituent on the substituted $C_1$–$C_6$ alkyl is selected from unsubstituted or substituted aryl, $C_3$–$C_{10}$ cycloalkyl, $R^{12}O$—, $R^{11}S(O)_m$—, $R^{10}C(O)$— or —$N(R^{10})_2$; or any two of $R^{6a}$, $R^{6b}$, $R^{6c}$, $R^{6d}$ and $R^{6e}$ on adjacent carbon atoms are combined to form a diradical selected from —CH=CH—CH=CH—, —CH=CH—CH$_2$—, —(CH$_2$)$_4$— and —(CH$_2$)$_3$—.

Preferably, $R^8$ is independently selected from:
a) hydrogen, and
b) aryl, substituted aryl, heterocycle, substituted heterocycle, $C_1$–$C_6$ perfluoroalkyl or CN. Preferably, $R^9$ is hydrogen, halogen, CF$_3$ or methyl. Preferably, $R^{10}$ is selected from H, $C_1$–$C_6$ alkyl and benzyl.

Preferably, $A^1$ and $A^2$ are independently selected from: a bond, —C(O)NR$^{10}$—, —NR$^{10}$C(O)—, O, —N(R$^{10}$)—, —S(O)$_2$N(R$^{10}$)— and —N(R$^{10}$)S(O)$_2$—.

Preferably, V is selected from hydrogen, heterocycle and aryl. More preferably, V is phenyl.

Preferably, W is selected from imidazolinyl, imidazolyl, oxazolyl, pyrazolyl, pyyrolidinyl, thiazolyl and pyridyl. More preferably, W is selected from imidazolyl and pyridyl.

Preferably, n and r are independently 0, 1, or 2.
Preferably s is 0.
Preferably t is 1.

It is intended that the definition of any substituent or variable (e.g., $R^{1a}$, $R^9$, n, etc.) at a particular location in a molecule be independent of its definitions elsewhere in that molecule. Thus, —N(R$^{10}$)$_2$ represents —NHH, —NHCH$_3$, —NHC$_2$H$_5$, etc. It is understood that substituents and substitution patterns on the compounds of the instant invention can be selected by one of ordinary skill in the art to provide compounds that are chemically stable and that can be synthesized by techniques known in the art, as well as those methods set forth below, from readily available starting materials.

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

The pharmaceutically acceptable salts of the compounds of this invention can be synthesized from the compounds of this invention which contain a basic moiety by conventional chemical methods. Generally, the salts are prepared either by ion exchange chromatography or by reacting the free base with stoichiometric amounts or with an excess of the desired salt-forming inorganic or organic acid in a suitable solvent or various combinations of solvents.

Reactions used to generate the compounds of this invention are prepared by employing reactions as shown in the Schemes 1–25, in addition to other standard manipulations such as ester hydrolysis, cleavage of protecting groups, etc., as may be known in the literature or exemplified in the experimental procedures. Substituents $R^3$, $R^6$ and $R^8$, as shown in the Schemes, represent the substituents $R^3$, $R^4$, $R^5$, $R^{6a}$, $R^{6b}$, $R^{6c}$, $R^{6d}$, $R^{6e}$ and $R^8$; although only one such $R^6$ or $R^8$ is present in the intermediates and products of the schemes, it is understood that the reactions shown are also applicable when such aryl or heteroaryl moieties contain multiple substituents.

These reactions may be employed in a linear sequence to provide the compounds of the invention or they may be used to synthesize fragments which are subsequently joined by the alkylation reactions described in the Schemes. Other reactions useful in the preparation of heteroaryl moieties are described in "Comprehensive Organic Chemistry, Volume 4: Heterocyclic Compounds" ed. P. G. Sammes, Oxford (1979) and references therein. Aryl-aryl coupling is generally described in "Comprehensive Organic Functional Group Transformations," Katritsky et al. eds., pp 472–473, Pergamon Press (1995).

Synopsis of Schemes 1–25

The requisite intermediates are in some cases commercially available, or can be prepared according to literature procedures, for the most part. Schemes 1–15 illustrate synthesis of the instant arylheteroaryl compound which incorporate a preferred benzylimidazolyl side-chain. Thus, in Scheme 1, for example, a arylheteroaryl intermediate that is not commercially available may be synthesized by methods known in the art. Thus, a phenyl boronic acid I may be reacted under Suzuki coupling conditions (*Pure Appl. Chem.*, 63:419 (1991)) with a suitably substituted halogenated heteroaryl moiety, such as 2-bromothienyl-4-carboxylic acid, to provide the arylheteroaryl carboxylic acid II. The acid may be reduced and the triflate of the intermediate alcohol III may be formed in situ and coupled to a suitably substituted benzylimidazolyl IV to provide, after deprotection, the instant compound V.

Schemes 2–5 illustrate other methods of synthesizing the key alcohol intermediates, which can then be processed as described in Scheme 1. Thus, Scheme 2 illustrates the analogous s series of arylheteroaryl alcohol forming reactions starting with the halogenated heteroarylaldehyde.

Scheme 3 illustrates the reaction wherein the "terminal" phenyl moiety is employed in the Suzuki coupling as the halogenated reactant. Such a coupling reaction is also compatible when one of the reactants incorporates a suitably protected hydroxyl functionality as illustrated in Scheme 4.

Negishi chemistry (*Org. Synth.*, 66:67 (1988)) may also be employed to form the arylheteroaryl component of the instant compounds, as shown in Scheme 5. Thus, a zinc bromide adduct, such as phenyl zinc bromide, may be coupled to a suitably substituted heteroaryl halide in the presence of nickel (II) to provide the arylheteroaryl VI. The heteroaryl halide, phenyl halide and the zinc bromide adduct may be selected based on the availability of the starting reagents.

As illustrated in Scheme 6, the sequence of coupling reactions may be modified such that the aryl-heteroaryl bond is formed last. Thus, a suitably substituted imidazole may first be alkylated with a heteroarylmethyl halide to provide intermediate VII. Intermediate VII can then undergo Suzuki type coupling to a suitably substituted heteroaryl boronic acid.

Scheme 7 illustrates the synthesis of a thiazole containing instant compound from the acyclic precursors. Further substitution on the thiazole ring may be accomplished as illustrated in Scheme 7a. Similar strategies may be utilized to prepare other bisheteroatom moieties.

Schemes 8 and 9 illustrate synthetic strategies that utilize the nucleophilicity of an imidazolyl moiety in the arylheteroaryl. Thus, as shown in Scheme 8, the commercially available 4-phenylimidazole may be reacted with a suitably substituted imidazolyl methyl halide to provide the instant compound VIII. If a particular substituted aryl imidazole is not commercially available, it may be synthesized as illustrated in Scheme 9.

Scheme 10 illustrates synthesis of an instant compound wherein a non-hydrogen $R^{9b}$ is incorporated in the instant compound. Thus, a readily available 4-substituted imidazole IX may be selectively iodinated to provide the 5-iodoimidazole X. That imidazole may then be protected and coupled to a suitably substituted benzyl moiety to provide intermediate XI. Intermediate XI can then undergo the alkylation reactions that were described hereinabove.

Scheme 11 illustrates synthesis of instant compounds that incorporate a preferred imidazolyl moiety connected to the arylheteroaryl via an alkyl amino, sulfonamide or amide linker. Thus, the 4-aminoalkylimidazole XII, wherein the primary amine is protected as the phthalimide, is selectively alkylated then deprotected to provide the amine XIII. The amine XIII may then react under conditions well known in the art with various activated arylheteroaryl moieties to provide the instant compounds shown.

Compounds of the instant invention wherein the $A^1$ $(CR^1_2)_nA^2(CR^1_2)_n$ linker is oxygen may be synthesized by methods known in the art, for example as shown in Scheme 12. The suitably substituted phenol XIV may be reacted with methyl N-(cyano)methanimidate to provide the 4-phenoxyimidazole XV. After selective protection of one of the imidazolyl nitrogens, the intermediate XVI can undergo alkylation reactions as described for the benzylimidazoles hereinabove.

Scheme 13 illustrates an analogous series of reactions wherein the $(CR^2_2)_pX(CR^2_2)_p$ linker of the instant compounds is oxygen. Thus, a suitably substituted haloheteroaryl alcohol, such as 4-bromo-2-thienol, is reacted with methyl N-(cyano)methanimidate to provide intermediate XVI. Intermediate XVI is then protected and, if desired to form a compound of a preferred embodiment, alkylated with a suitably protected benzyl. The intermediate XVII can then be coupled to a suitably substituted phenyl boronic acid by Suzuki chemistry to provide the instant compound.

Compounds of the instant invention wherein the $A^1$ $(CR^1_2)_nA^2(CR^1_2)_n$ linker is a substituted methylene may be synthesized by the methods shown in Scheme 14. Thus, the N-protected imidazolyl iodide XVIII is reacted, under Grignard conditions with a suitably protected benzaldehyde to provide the alcohol XIX. Acylation, followed by the alkylation procedure illustrated in the Schemes above (in particular, Scheme 1) provides the instant compound XX. If other $R^1$ substituents are desired, the acetyl moiety can be manipulated as illustrated in the Scheme.

Addition of various nucleophiles to an imidazolyl aldehyde may also be employed to form a substituted alkyl linker between the biheteroaryl and the preferred W (imidazolyl) as shown in Scheme 15. Thus a bishalogenated five membered heteroaryl, such as 2,4-dibromothiophene, may undergo metal halogen exchange followed by reaction with a suitably substituted imidazolyl aldehyde and acteylation to form a regioisomeric mixture of the acetyl intermediates. The halogenated regioisomeric mixture may be chromatographically separated at this stage, if convenient. Suzuki coupling with a suitably substituted 6-membered heteroaryl boronic acid affords the instant acetoxy compound, which can be treated with lithium hydroxide to remove the acetyl group. Then, similar substituent manipulation as shown in Scheme 14 may be performed on a fully functionalized compound which incorporates an $R^2$ hydroxyl moiety.

SCHEME 1

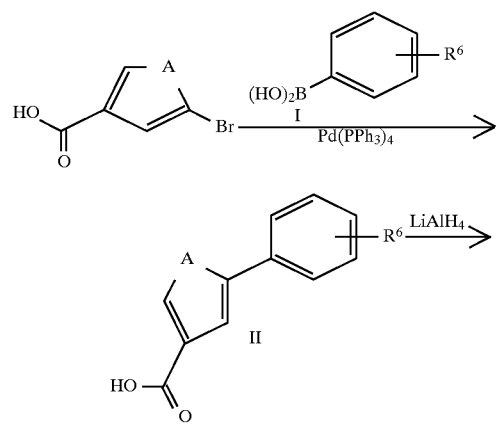

SCHEME 1 -continued
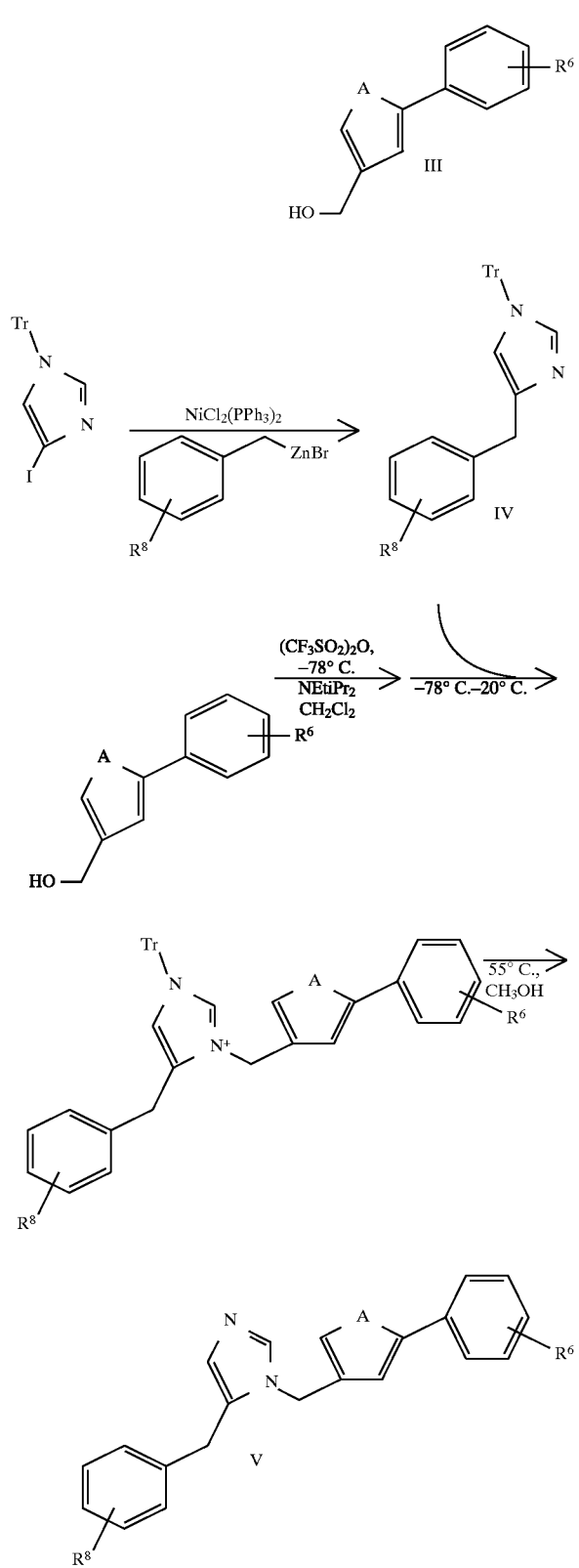
SCHEME 2
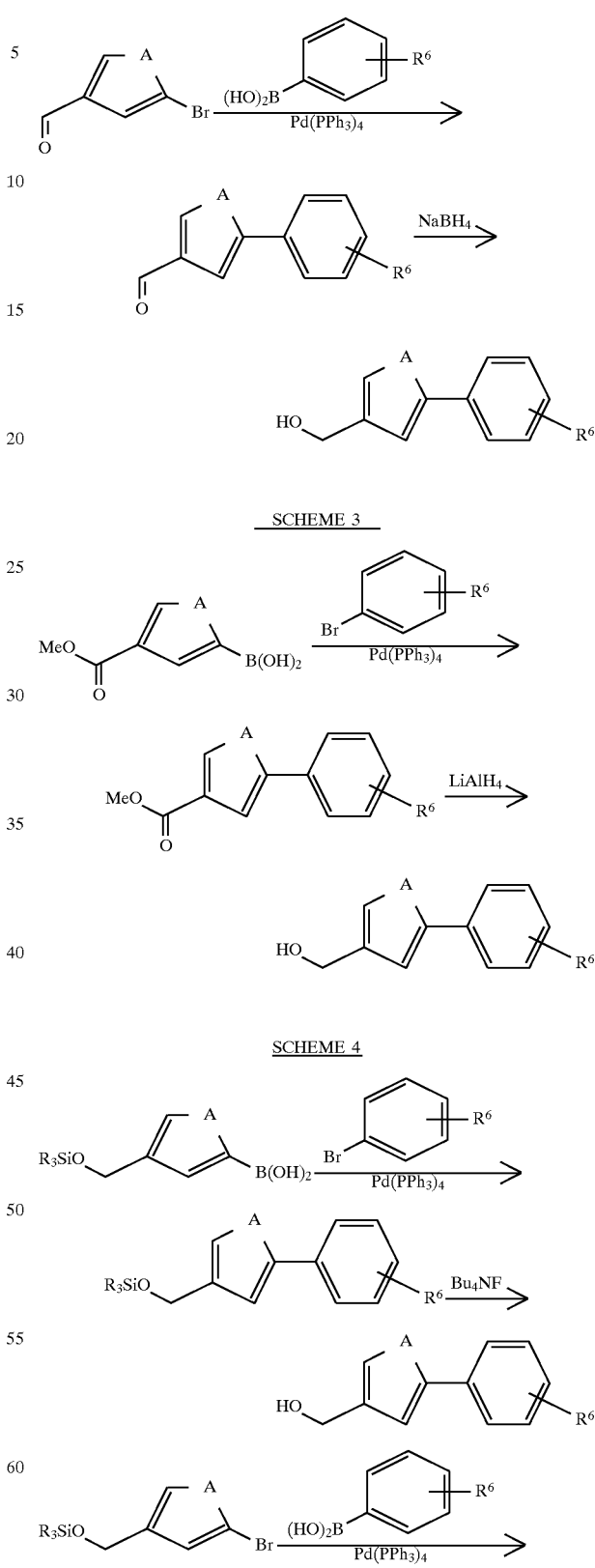

-continued
SCHEME 4
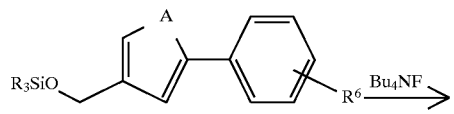
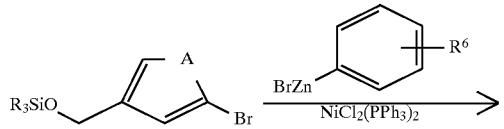
SCHEME 5
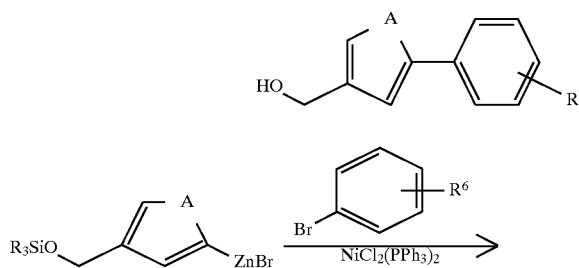
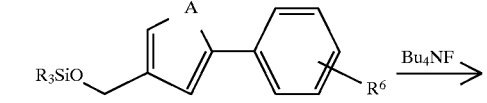
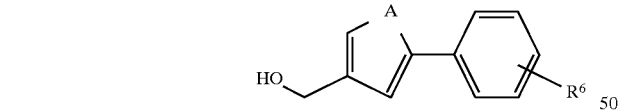
SCHEME 6
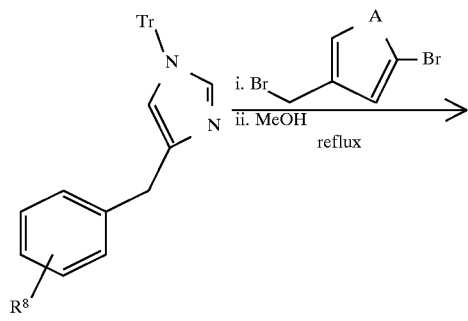
SCHEME 6
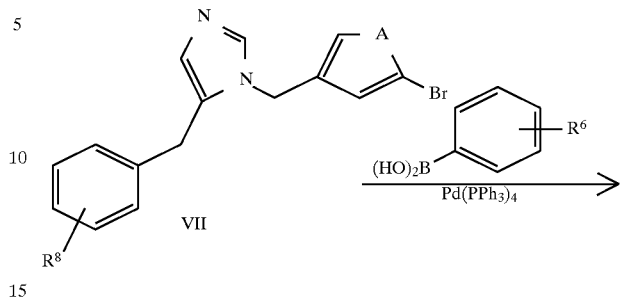
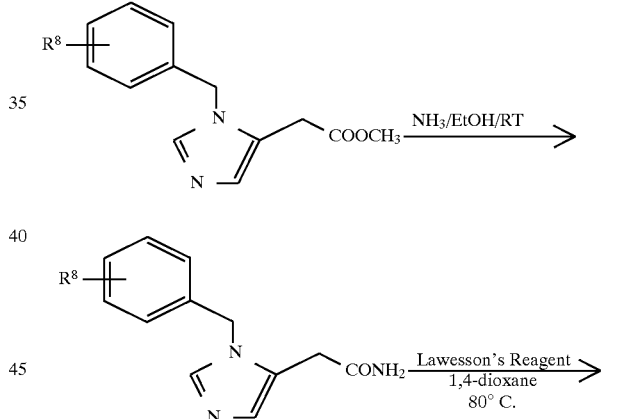
SCHEME 7
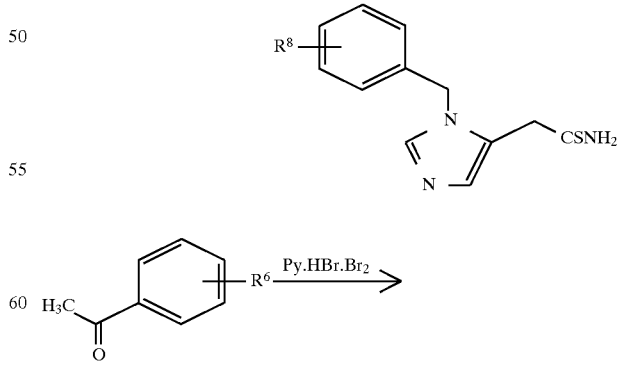

SCHEME 7
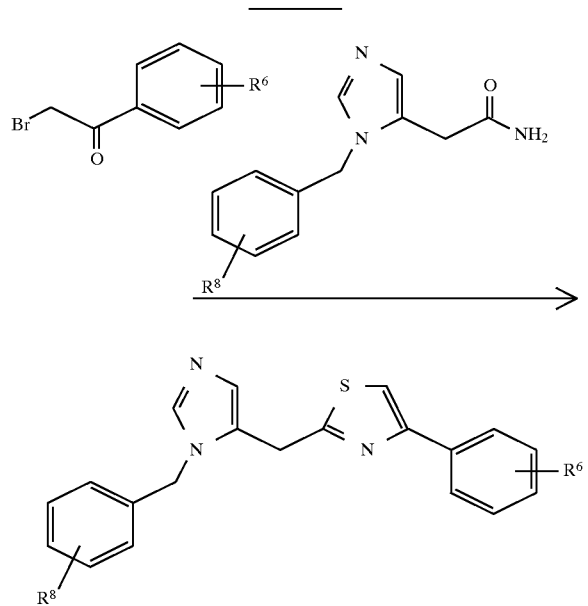
SCHEME 7a
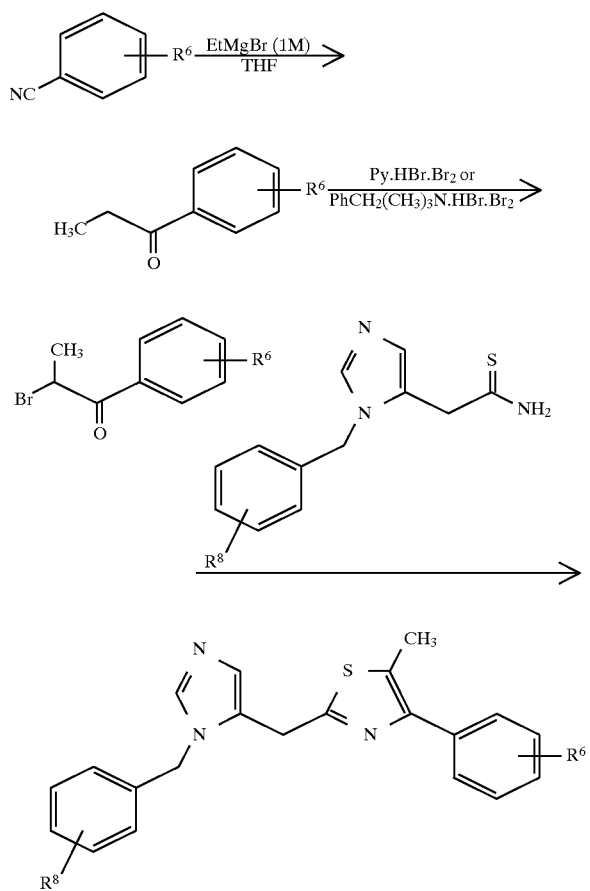
SCHEME 8
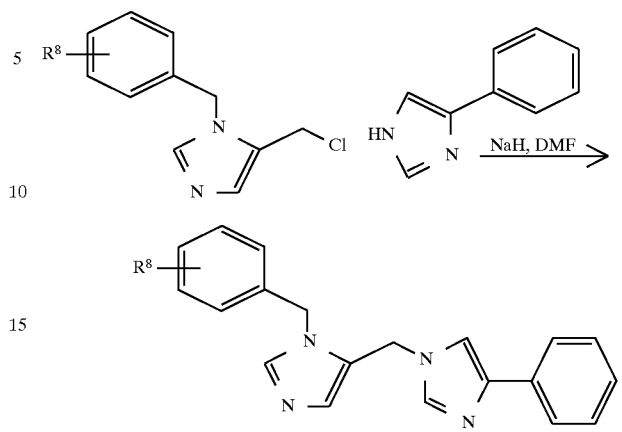
SCHEME 9
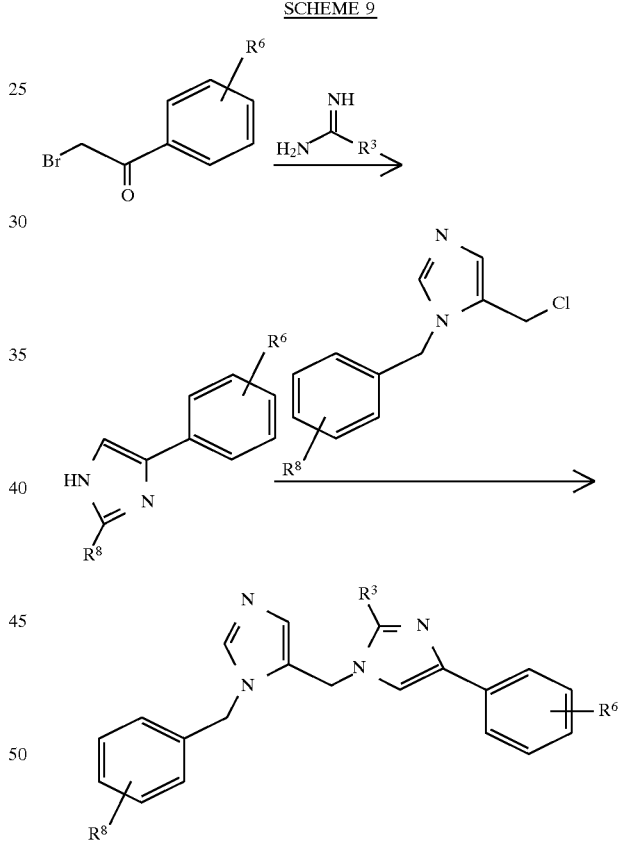
SCHEME 10
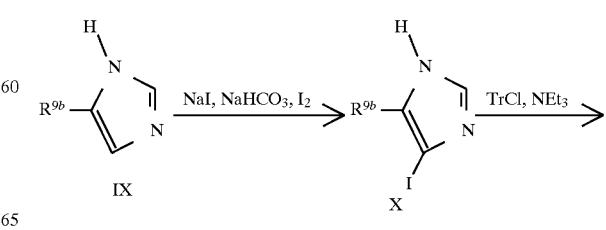

5,859,035
SCHEME 10
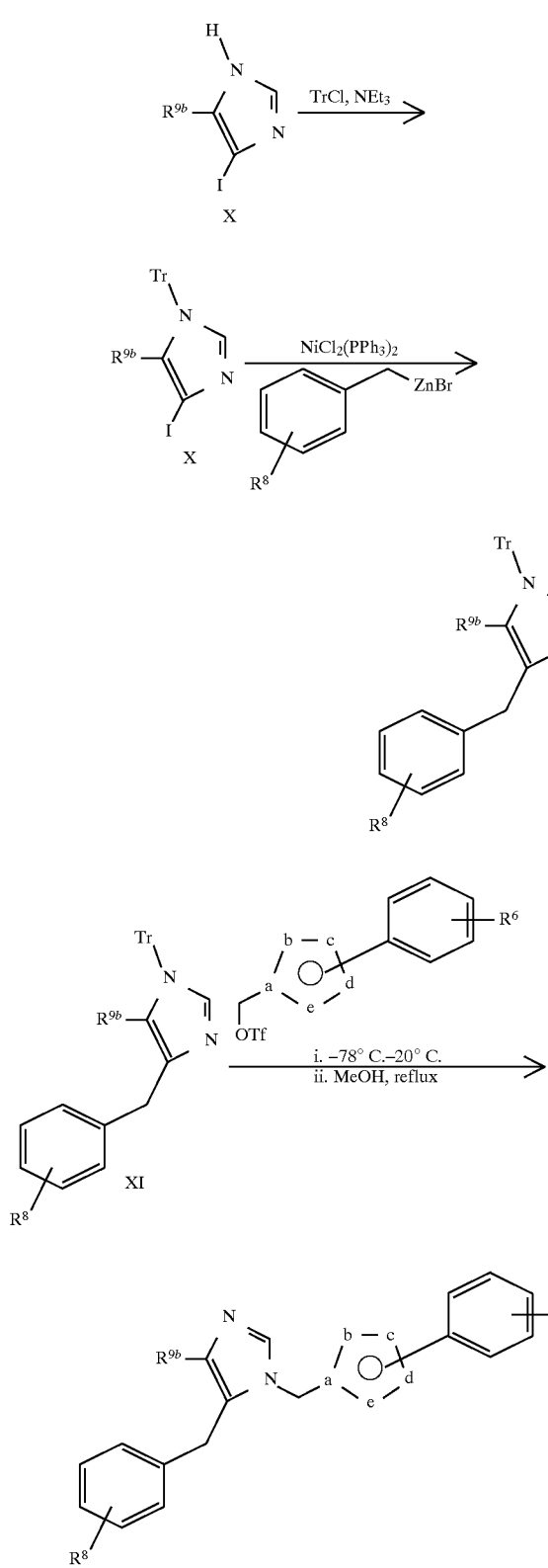
SCHEME 11
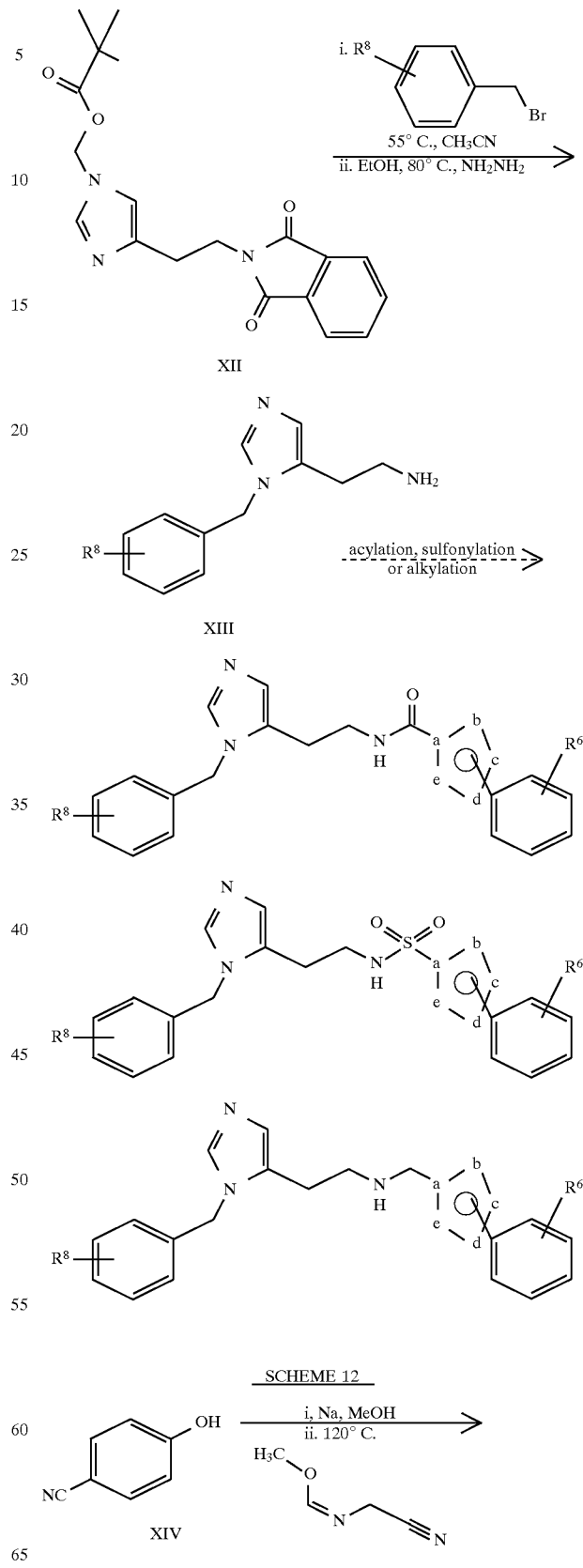

-continued
SCHEME 12
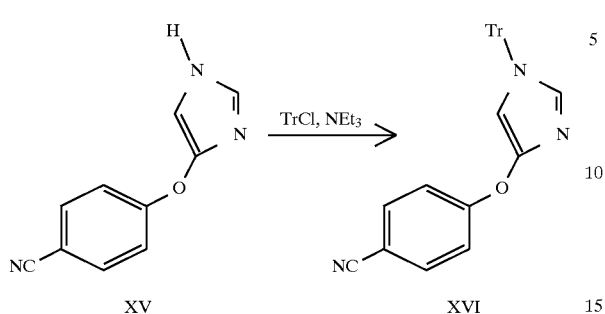
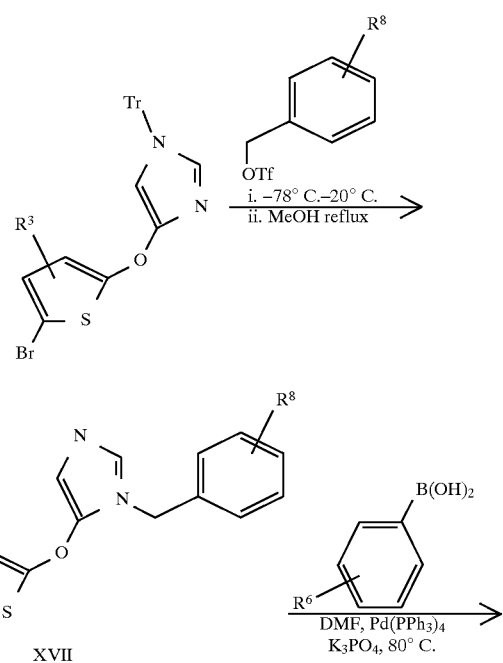
-continued
SCHEME 13
SCHEME 13
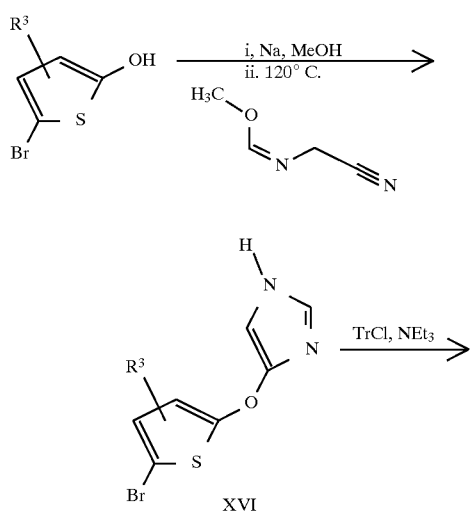
SCHEME 14
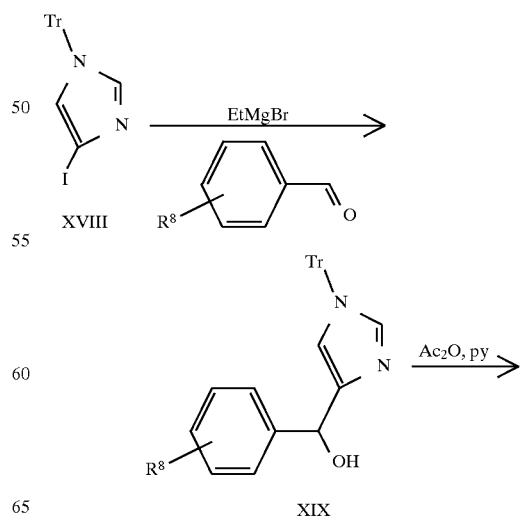

SCHEME 14 -continued

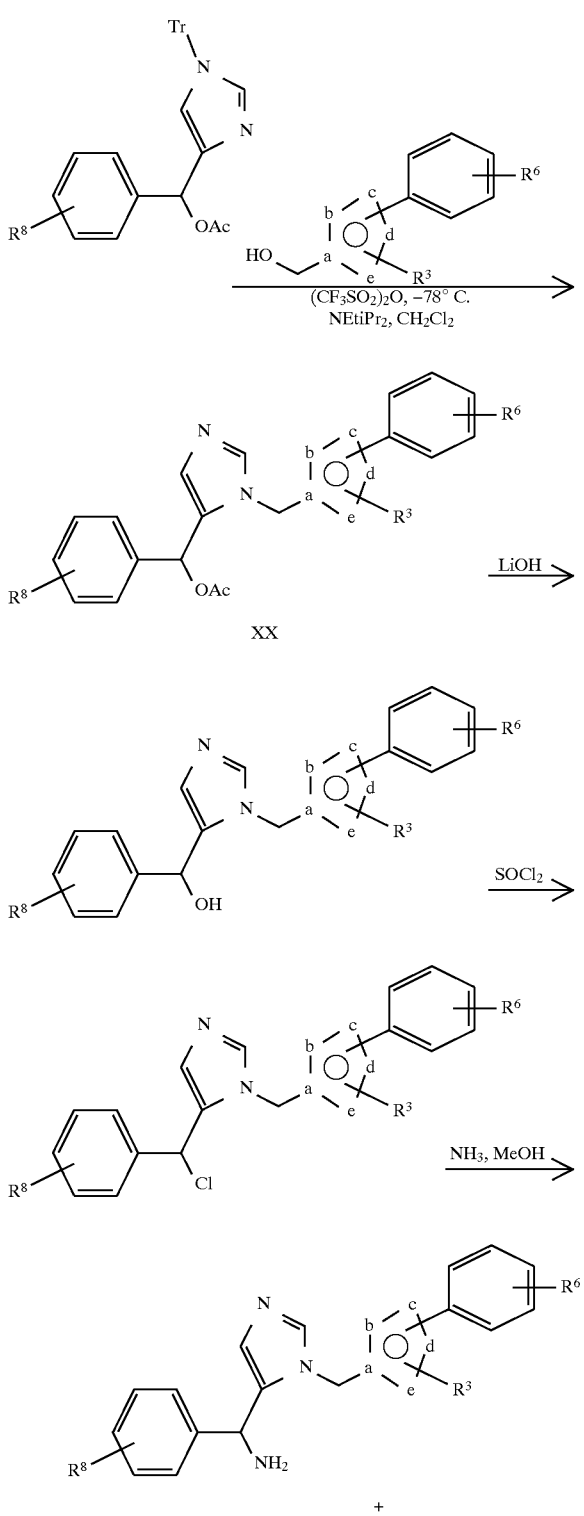

SCHEME 14 -continued

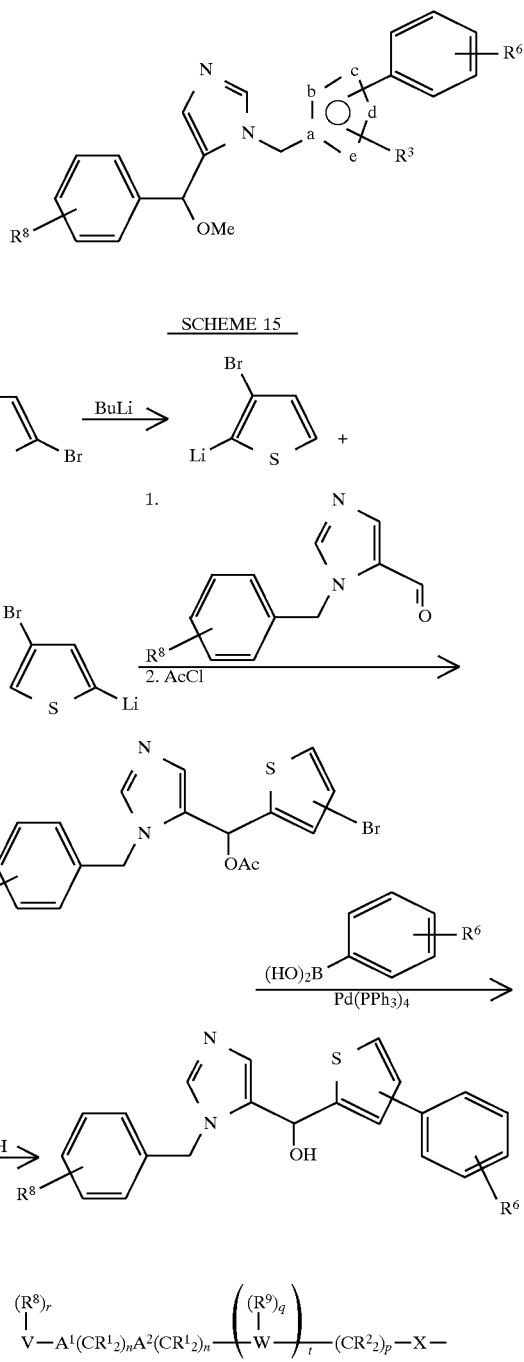

SCHEME 15 incorporated in the compounds of the instant invention is represented by other than a substituted imidazole-containing group.

Thus, the intermediates whose synthesis are illustrated in Schemes hereinabove and other arylheteroaryl intermediates obtained commercially or readily synthesized, can be coupled with a variety of aldehydes, as shown in Scheme 16. The aldehydes can be prepared by standard procedures, such as that described by O. P. Goel, U. Krolls, M. Stier and S. Kesten in *Organic Syntheses*, 1988, 67, 69–75, from the appropriate amino acid. Metal halogen exchange chemistry (Scheme 15) may be employed when manipulating the aldehydes. Alternatively, Grignard chemistry may be utilized, as shown in Scheme 16. Thus, Suzuki coupling provides, for example, the pyrrole containing biheteroaryl XXI. Reaction of the intermediate XXI with a Grignard reagent provides the N-pyrrylmagnesium derivative XXIa, which is then reacted with an aldehyde to provide the C-alkylated instant compound XXII. The product XXII can be deoxygenated by methods known in the art, such as a catalytic hydrogention, then deprotected with trifluoroacetic acid in methylene chloride to give the final compound XXIIa. The final product XXII may be isolated in the salt form, for example, as a trifluoroacetate, hydrochloride or acetate salt, among others. The product diamine XXII can further be selectively protected to obtain XXIII, which can subsequently be reductively alkylated with a second aldehyde to obtain XXIV. Removal of the protecting group, and conversion to cyclized products such as the dihydroimidazole XXV can be accomplished by literature procedures.

Scheme 17 illustrates the use of in situ formation of a lithium anion of a suitably substituted N-alkyl pyrrole to provide the C-alkylated compound of the instant invention.

If the arylheteroaryl subunit is reacted with an aldehyde which also has a protected hydroxyl group, such as XXVI in Scheme 18, the protecting groups can be subsequently removed to unmask the hydroxyl group (Schemes 18, 19). The alcohol can be oxidized under standard conditions to e.g. an aldehyde, which can then be reacted with a variety of organometallic reagents such as Grignard reagents, to obtain secondary alcohols such as XXX. In addition, the fully deprotected amino alcohol XXXI can be reductively alkylated (under conditions described previously) with a variety of aldehydes to obtain secondary amines, such as XXXII (Scheme 19), or tertiary amines.

The Boc protected amino alcohol XXVIII can also be utilized to synthesize 2-aziridinylmethylarylheteroaryl such as XXXIII (Scheme 20). Treating XXVIII with 1,1'-sulfonyldiimidazole and sodium hydride in a solvent such as dimethylformamide led to the formation of aziridine XXXIII. The aziridine is reacted with a nucleophile, such as a thiol, in the presence of base to yield the ring-opened product XXXIV.

In addition, the arylheteroaryl subunit can be reacted with aldehydes derived from amino acids such as O-alkylated tyrosines, according to standard procedures, to obtain compounds such as XL, as shown in Scheme 21. When R' is an aryl group, XL can first be hydrogenated to unmask the phenol, and the amine group deprotected with acid to produce XLI. Alternatively, the amine protecting group in XL can be removed, and O-alkylated phenolic amines such as XLII produced.

Schemes 22–25 illustrate syntheses of suitably substituted aldehydes useful in the syntheses of the instant compounds wherein the variable W is present as a pyridyl moiety. Similar synthetic strategies for preparing alkanols that incorporate other heterocyclic moieties for variable W are also well known in the art.

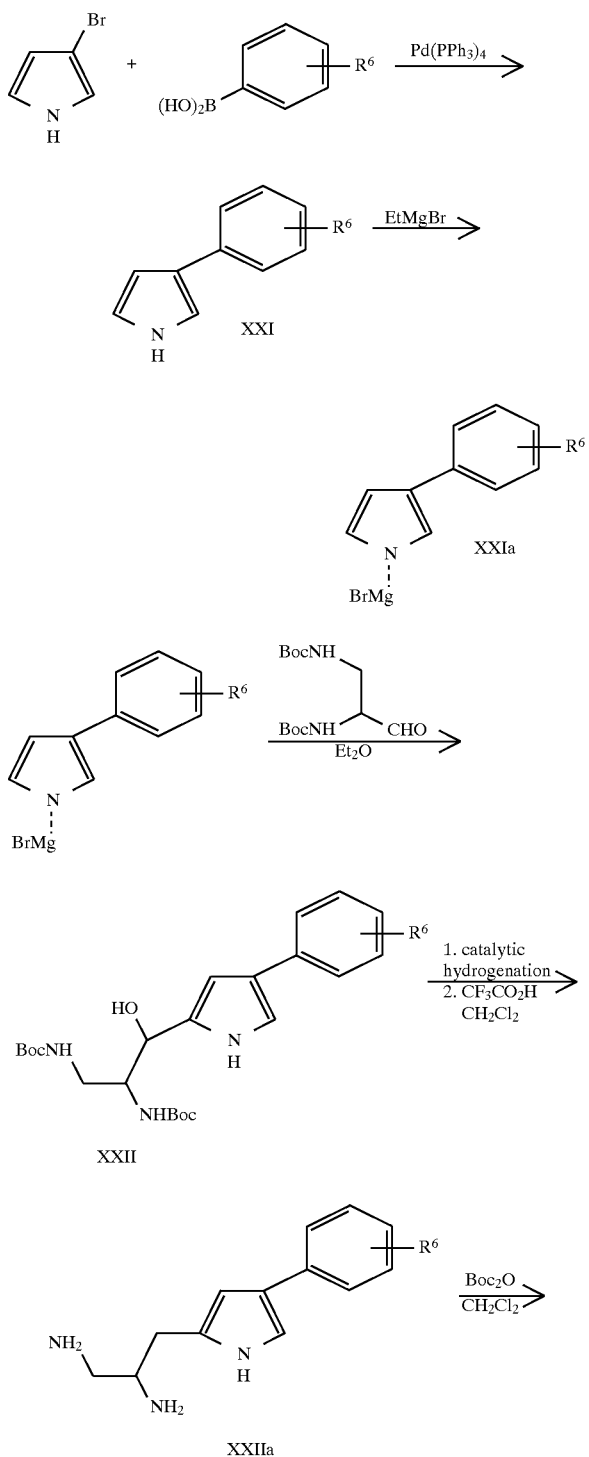

SCHEME 16
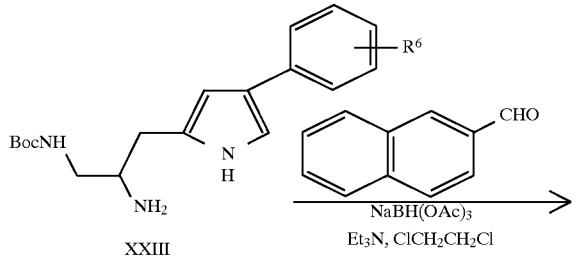
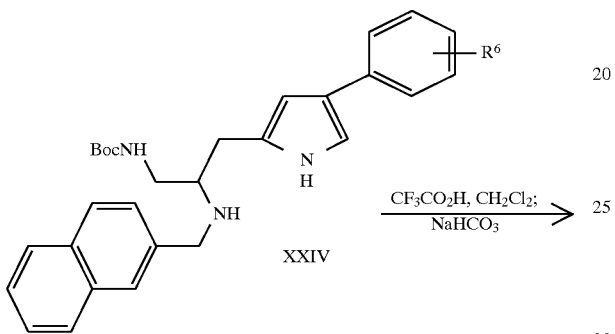
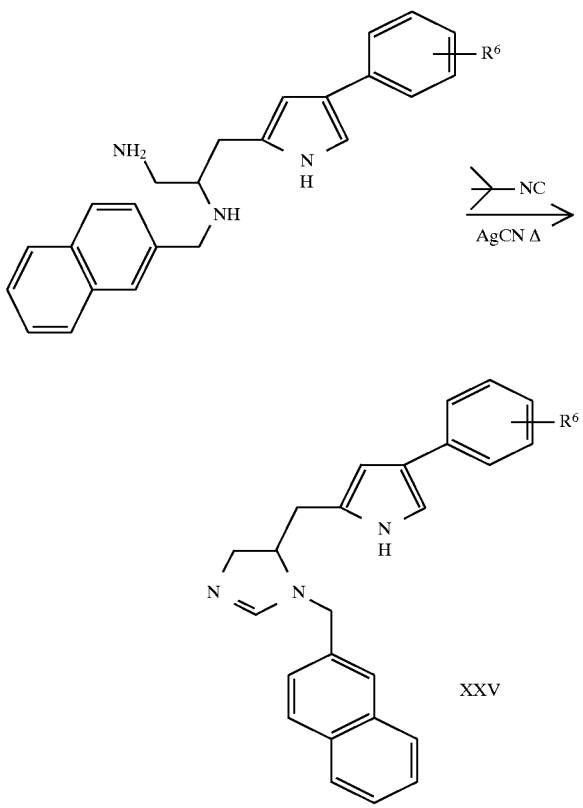
SCHEME 17
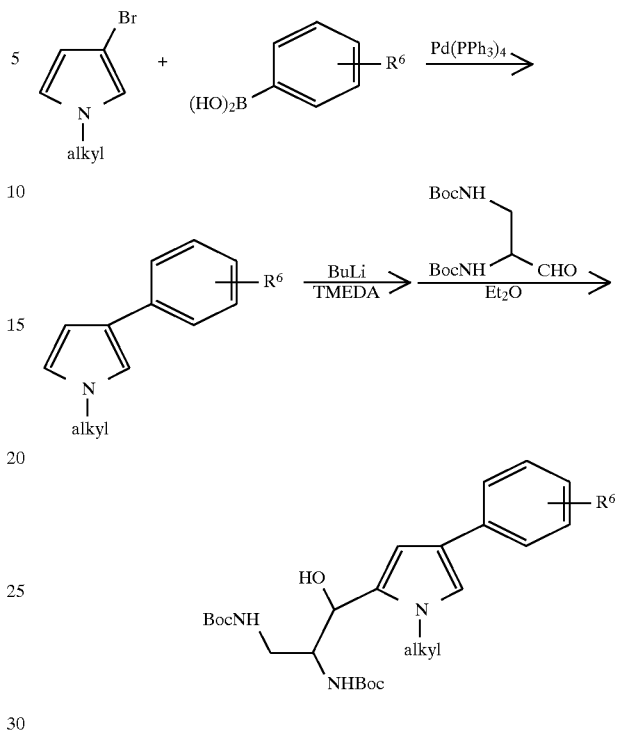
SCHEME 18
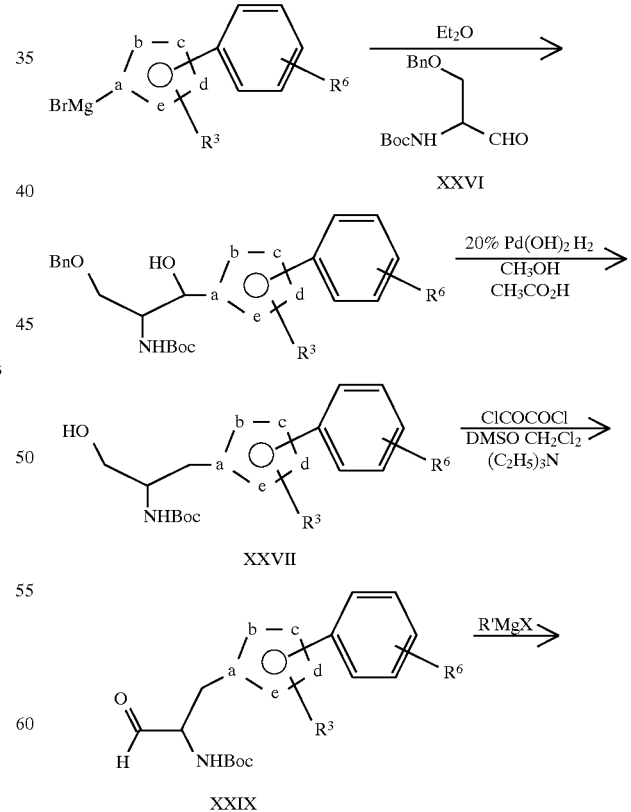

-continued
SCHEME 18
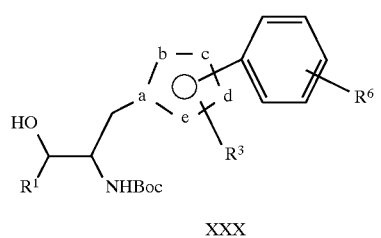
XXX
SCHEME 19
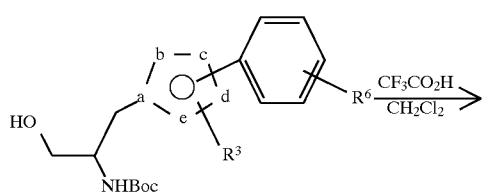
XXVIII
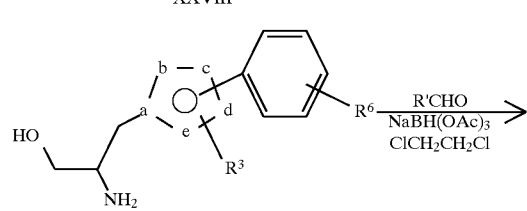
XXXI
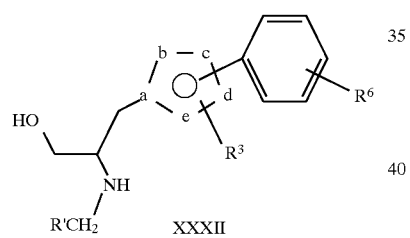
XXXII
SCHEME 20
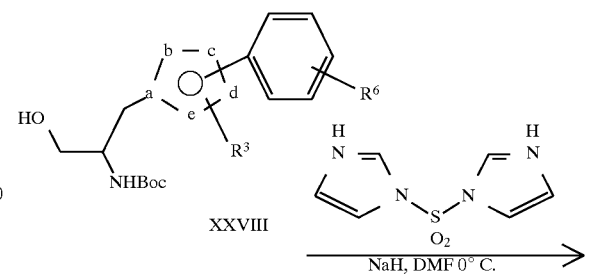
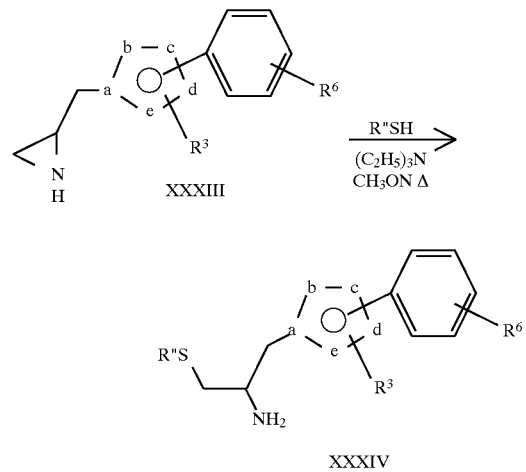
SCHEME 21
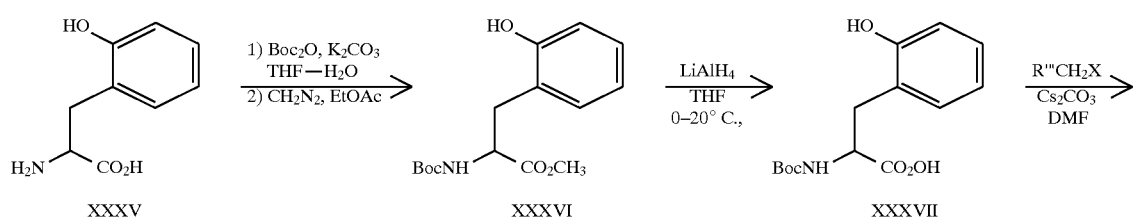

-continued
SCHEME 21
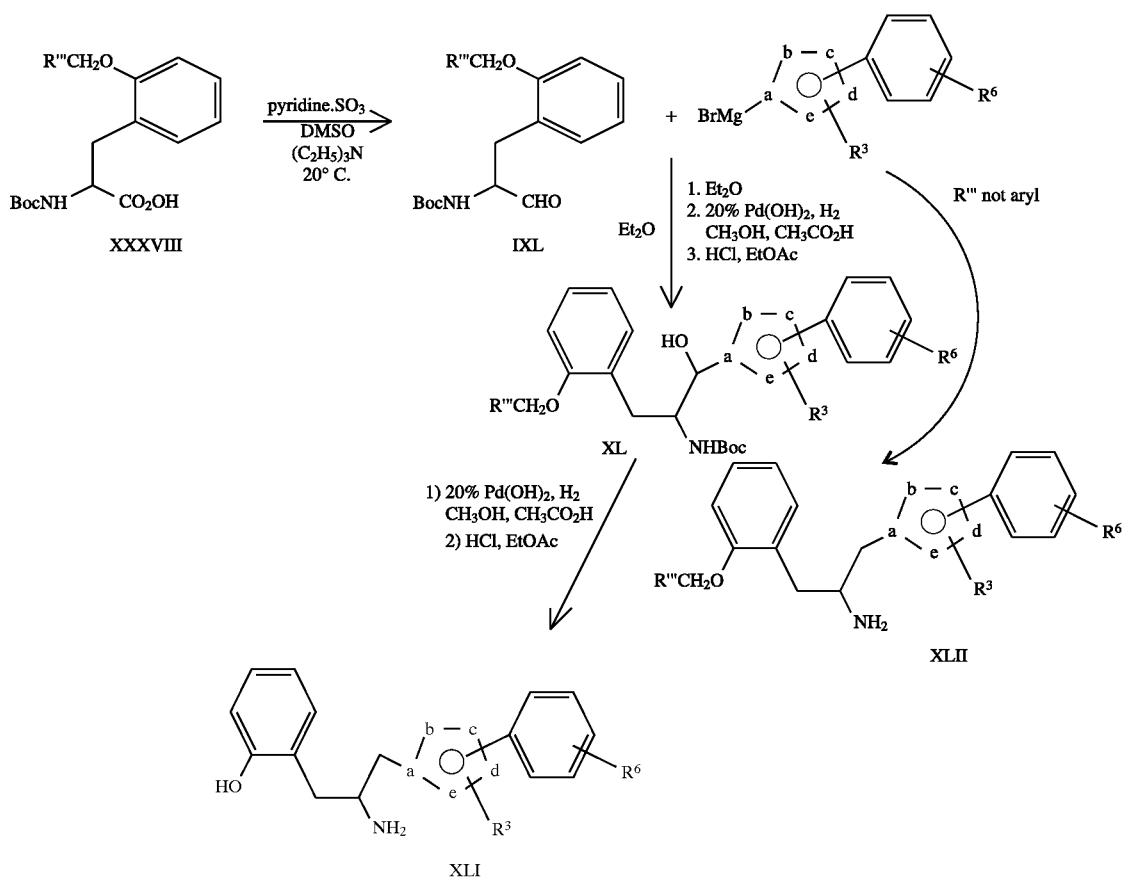
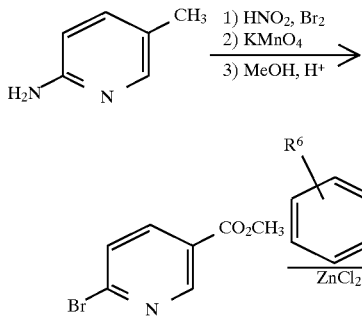
SCHEME 22
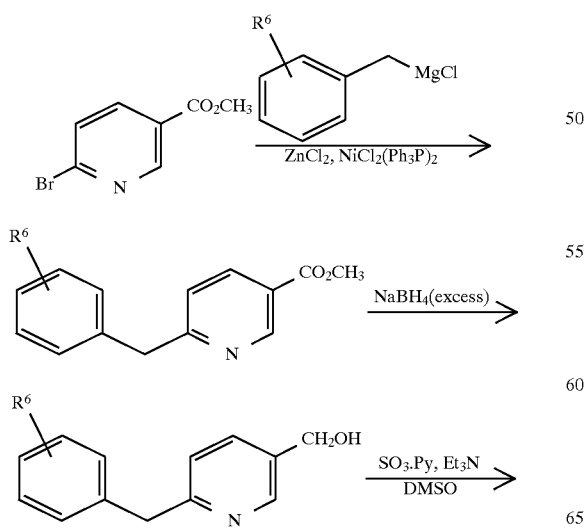
-continued
SCHEME 22
SCHEME 23
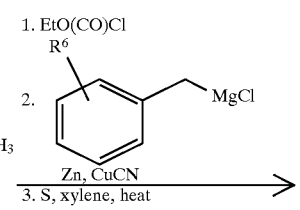

SCHEME 23 (continued)
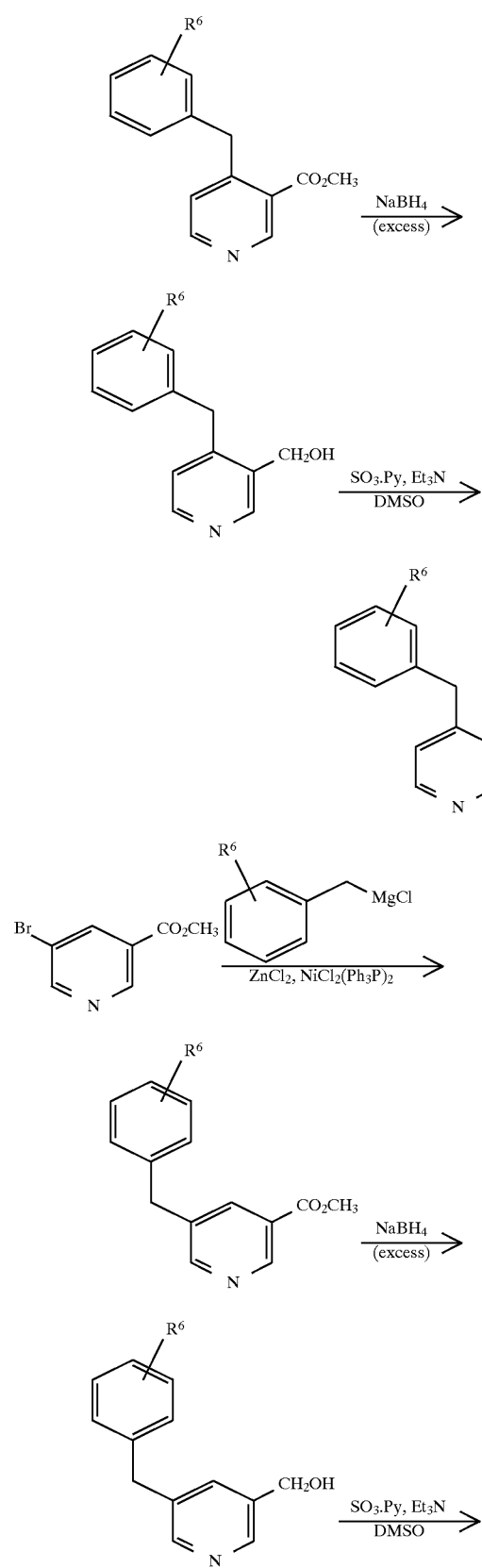
SCHEME 24
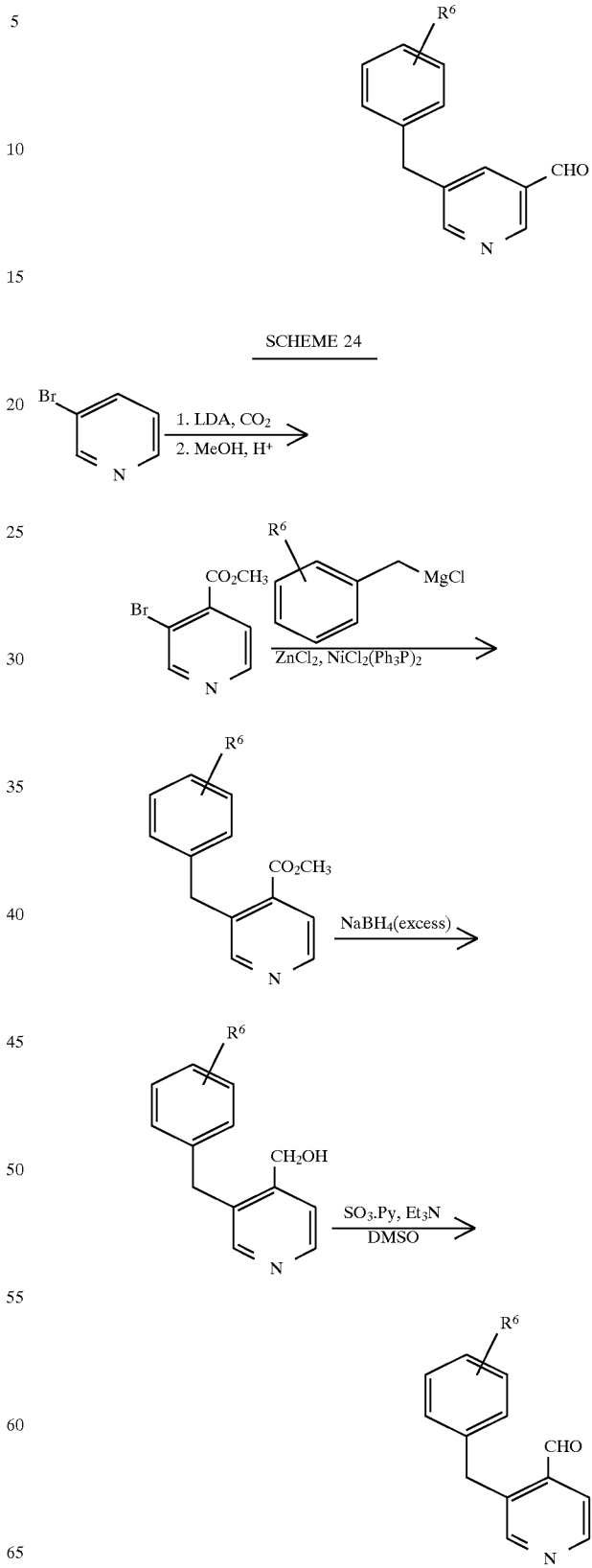

SCHEME 25

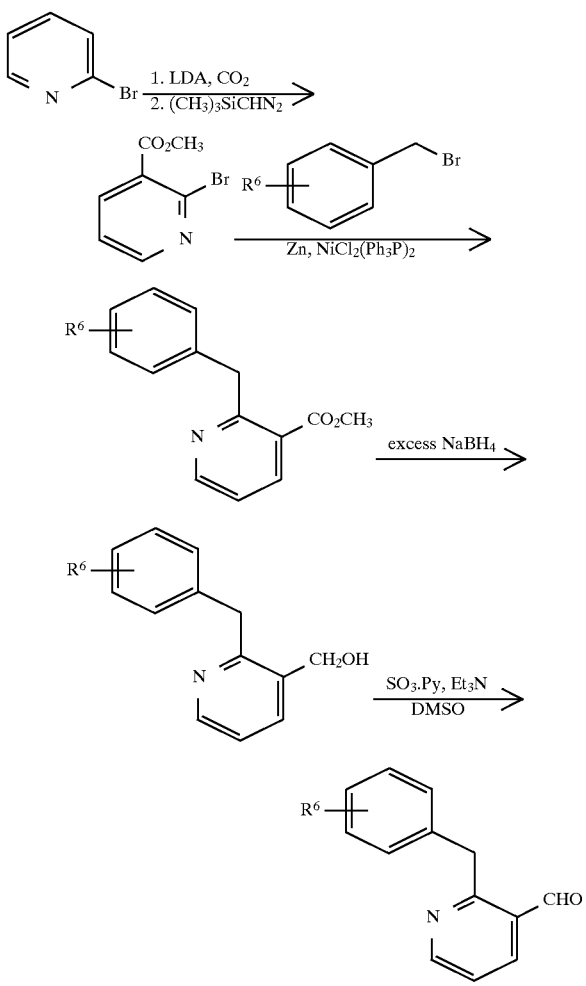

The instant compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, myeloid leukemias and neurological tumors. Such tumors may arise by mutations in the ras genes themselves, mutations in the proteins that can regulate Ras activity (i.e., neurofibromin (NF-1), neu, scr, abl, lck, fyn) or by other mechanisms.

The compounds of the instant invention inhibit farnesyl-protein transferase and the farnesylation of the oncogene protein Ras. The instant compounds may also inhibit tumor angiogenesis, thereby affecting the growth of tumors (J. Rak et al. *Cancer Research*, 55:4575–4580 (1995)). Such anti-angiogenesis properties of the instant compounds may also be useful in the treatment of certain forms of blindness related to retinal vascularization.

The compounds of this invention are also useful for inhibiting other proliferative diseases, both benign and malignant, wherein Ras proteins are aberrantly activated as a result of oncogenic mutation in other genes (i.e., the Ras gene itself is not activated by mutation to an oncogenic form) with said inhibition being accomplished by the administration of an effective amount of the compounds of the invention to a mammal in need of such treatment. For example, a component of NF-1 is a benign proliferative disorder.

The instant compounds may also be useful in the treatment of certain viral infections, in particular in the treatment of hepatitis delta and related viruses (J. S. Glenn et al. *Science*, 256:1331–1333 (1992)).

The compounds of the instant invention are also useful in the prevention of restenosis after percutaneous transluminal coronary angioplasty by inhibiting neointimal formation (C. Indolfi et al. *Nature medicine*, 1:541–545 (1995)).

The instant compounds may also be useful in the treatment and prevention of polycystic kidney disease (D. L. Schaffner et al. *American Journal of Pathology*, 142:1051–1060 (1993) and B. Cowley, Jr. et al. *FASEB Journal*, 2:A3160 (1988)).

The instant compounds may also be useful for the treatment of fungal infections.

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

For oral use of a chemotherapeutic compound according to this invention, the selected compound may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The compounds of the instant invention may also be co-administered with other well known therapeutic agents that are selected for their particular usefulness against the condition that is being treated. For example, the instant compounds may be useful in combination with known anti-cancer and cytotoxic agents. Similarly, the instant compounds may be useful in combination with agents that are effective in the treatment and prevention of NF-1, restinosis, polycystic kidney disease, infections of hepatitis delta and related viruses and fungal infections.

If formulated as a fixed dose, such combination products employ the compounds of this invention within the dosage range described below and the other pharmaceutically active agent(s) within its approved dosage range. Compounds of the instant invention may alternatively be used sequentially with known pharmaceutically acceptable agent(s) when a combination formulation is inappropriate.

The present invention also encompasses a pharmaceutical composition useful in the treatment of cancer, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's blood-stream by local bolus injection.

As used herein, the term "composition" is intended to encompass a product comprising the specified ingredients in the specific amounts, as well as any product which results, directly or indirectly, from combination of the specific ingredients in the specified amounts.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 60 mg/kg of body weight per day, preferably of between 0.5 mg/kg of body weight to about 40 mg/kg of body weight per day.

The compounds of the instant invention are also useful as a component in an assay to rapidly determine the presence and quantity of farnesyl-protein transferase (FPTase) in a composition. Thus the composition to be tested may be divided and the two portions contacted with mixtures which comprise a known substrate of FPTase (for example a tetrapeptide having a cysteine at the amine terminus) and farnesyl pyrophosphate and, in one of the mixtures, a compound of the instant invention. After the assay mixtures are incubated for an sufficient period of time, well known in the art, to allow the FPTase to farnesylate the substrate, the chemical content of the assay mixtures may be determined by well known immunological, radiochemical or chromatographic techniques. Because the compounds of the instant invention are selective inhibitors of FPTase, absence or quantitative reduction of the amount of substrate in the assay mixture without the compound of the instant invention relative to the presence of the unchanged substrate in the assay containing the instant compound is indicative of the presence of FPTase in the composition to be tested.

It would be readily apparent to one of ordinary skill in the art that such an assay as described above would be useful in identifying tissue samples which contain farnesyl-protein transferase and quantitating the enzyme. Thus, potent inhibitor compounds of the instant invention may be used in an active site titration assay to determine the quantity of enzyme in the sample. A series of samples composed of aliquots of a tissue extract containing an unknown amount of farnesyl-protein transferase, an excess amount of a known substrate of FPTase (for example a tetrapeptide having a cysteine at the amine terminus) and farnesyl pyrophosphate are incubated for an appropriate period of time in the presence of varying concentrations of a compound of the instant invention. The concentration of a sufficiently potent inhibitor (i.e., one that has a Ki substantially smaller than the concentration of enzyme in the assay vessel) required to inhibit the enzymatic activity of the sample by 50% is approximately equal to half of the concentration of the enzyme in that particular sample.

EXAMPLES

Examples provided are intended to assist in a further understanding of the invention. Particular materials employed, species and conditions are intended to be further illustrative of the invention and not limitative of the reasonable scope thereof.

Example 1

1-{[1-(4-Cyanobenzyl)-1H-imidazol-5-yl]ethyl}-4-phenyl-imidazole bishydrochloride salt Step A: 1H-Imidazole-4-acetic acid methyl ester hydrochloride A solution of 1H-imidazole-4-acetic acid hydrochloride (4.00 g, 24.6 mmol) in methanol (100 mL) was saturated with gaseous hydrogen chloride. The resulting solution was allowed to stand at room temperature for 18 hours. The solvent was evaporated in vacuo to afford the title compound as a white solid.

$^1$H NMR (CDCl$_3$, 400 MHz) δ 8.85(1H, s), 7.45(1H, s), 3.89(2H, s) and 3.75(3H, s) ppm.

Step B: 1-(Triphenylmethyl)-1H-imidazol-4-ylacetic acid methyl ester

To a solution of the product from Step A (24.85 g, 0.141 mol) in DMF (115 mL) was added triethylamine (57.2 mL, 0.412 mol) and triphenylmethyl bromide (55.3 g, 0.171 mol) and the suspension was stirred for 24 hours. After this time, the reaction mixture was diluted with EtOAc and water. The organic phase was washed with sat. aq. NaHCO$_3$, dried, (Na$_2$SO$_4$) and the solvent evaporated in vacuo. The residue was purified by chromatography (Silica gel, 0–100% EtOAc in hexanes) to provide the title compound as a white solid.

$^1$H NMR (CDCl$_3$, 400 MHz) δ 7.35(1H, s), 7.31(9H, m), 7.22(6H, m), 6.76(1H, s), 3.68(3H, s) and 3.60(2H, s) ppm.

Step C: [1-(4-Cyanobenzyl)-1H-imidazol-5-yl]acetic acid methyl ester

To a solution of the product from Step B (8.00 g, 20.9 mmol) in acetonitrile (70 mL) was added 4-cyanobenzyl bromide (4.10 g, 20.92 mmol) and heated at 55° C. for 3 hours. The reaction was cooled to room temperature and the resulting imidazolium salt was collected by filtration. The filtrate was heated at 55° C. for 18 hours. The reaction mixture was cooled to room temperature and evaporated in vacuo. To the residue was added EtOAc (70 mL) and the resulting precipitate collected by filtration. The precipitated imidazolium salts were combined, suspended in methanol (100 mL) and heated to reflux for 30 minutes. After this time, the solvent was removed in vacuo. The resulting residue was suspended in EtOAc (75 mL) and the solid isolated by filtration and washed with EtOAc. The solid was treated with sat. aq. NaHCO$_3$ solution (300 mL) and CH$_2$Cl$_2$ (300 mL) and stirred at room temperature for 2 hours. The organic layer was separated, dried, (MgSO$_4$) and evaporated in vacuo to afford the title compound as a white solid.

$^1$HNMR (CDCl$_3$, 400 MHz) δ 7.65(1H, d, J=8 Hz), 7.53(1H, s), 7.15(1H, d, J=8 Hz), 7.04(1 H, s), 5.24(2H, s), 3.62(3H, s) and 3.45(2H, s) ppm.

Step D: 5-[1-(4-Cyanobenzyl)-1H-imidazolyl]ethanol

To a stirred solution of the ester from example step C, (1.50 g, 5.88 mmol), in methanol (20 mL) at 0° C., was added sodium borohydride (1.00 g, 26.3 mmol) portionwise over 5 minutes. The reaction was stirred at 0° C. for 1 hour and then at room temperature for 1 hour. The reaction was quenched by the addition of sat. aq. NH$_4$Cl solution and the methanol evaporated in vacuo. The residue was partitioned between EtOAc and sat. aq. NaHCO$_3$ solution and the organic extracts dried, (MgSO$_4$) and evaporated in vacuo. The residue was purified by chromatography (Silica gel, 4–10% methanol in CH$_2$Cl$_2$) to afford the title compound as a white solid.

$^1$H NMR (CDCl$_3$ 400 MHz) δ 7.64(2H, d, J=8.2 Hz), 7.57(1H, s), 7.11(2H, d, J=8.2 Hz), 6.97(1H, s), 5.23(2H, s), 3.79(2H, t, J=6.2 Hz), 2.66(2H, t, J=6.2 Hz) ppm.

Step E: 5-(1-(4-Cyanobenzyl)-imidazolyl) ethylmethanesulfonate

A solution of 5-[1-(4-cyanobenzyl)-1H-imidazolyl] ethanol (0.500 g, 2.20 mmol) in CH$_2$Cl$_2$ (6 mL) at 0° C. was treated with Hunig's base (0.460 mL, 2.64 mmol) and methanesulfonyl chloride (0.204 mL, 2.64 mmol). After 2 hours, the reaction was quenched by addition of saturated NaHCO$_3$ solution (50 mL) and the mixture extracted with CH$_2$Cl$_2$ (50 mL), dried, (MgSO$_4$) and the solvent evaporated in vacuo. The title compound was used without further purification.

$^1$H NMR (CDCl$_3$ 400MHz) δ 7.69 (1H, s) 7.66(2H, d, J=8.2 Hz), 7.15 (2H, d, J=8.2 Hz), 7.04(1H, s), 5.24(2H, s), 4.31(2H, t, J=6.7 Hz), 2.96(3H, s), and 2.88(2H, t, J=6.6 Hz)ppm.

Step F: 1-{[1-(4-Cyanobenzyl)-1H-imidazol-5-yl]ethyl}-4-phenyl-imidazole bis hydrochloride salt To a suspension of sodium hydride (14.2 mg, 60% dispersion in mineral oil, 0.356 mmol) in DMF (0.30 mL) at 0° C. was added 4-phenylimidazole (48.8 mg, 0.339 mmol), and stirred for 20 minutes. A solution of the mesylate from step E (100 mg, 0.339 mmol) in DMF (0.50 mL) was added to the solution and stirring continued at 0° C. for 1 hour and then at room temperature for 16 hours. The reaction was quenched with sat. aq. ammonium chloride solution (0.10 mL), and the solvent evaporated in vacuo. The residue was purified by chromatography (Silica gel, 2–5% NH$_4$OH: acetonitrile). The resulting material was converted to the HCl salt by treating an EtOAc solution of the imidazole with gaseous HCl and evaporation of the solvent in vacuo.

Anal. Calcd for C$_{22}$H$_{19}$N$_5$.2.00HCl.1.50H$_2$O: C, 58.29; H, 5.34; N, 15.45. Found: C, 58.24; H, 5.47; N, 15.48. FAB HRMS exact mass calcd for C$_{22}$H$_{20}$N$_5$ 354.171871 (MH$^+$); found 354.171948. $^1$H NMR (CD$_3$OD 400 MHz) δ 8.93 (1H, s), 8.75(1H, s), 7.86(1H, s), 7.76(2H, d, J=7.9 Hz), 7.69(2H, d, 7.1 Hz), 7.65–7.35(6H, m), 5.61(2H, s) and 4.53(2H,m)ppm.

Example 2

1-{1-(4-Cyanobenzyl)-1H-imidazol-5-yl)methyl}-4-phenylimidazole bis hydrochloride salt Step A: 1-Triphenylmethyl-4-(hydroxymethyl)imidazole To a solution of 4-(hydroxymethyl)imidazole hydrochloride (35.0 g, 260 mmol) in dry DMF (250 mL) at room temperature was added triethylamine (90.6 mL, 650 mmol). A white solid precipitated from the solution. Chlorotriphenylmethane (76.1 g, 273 mmol) in DMF (500 mL) was added dropwise. The reaction mixture was stirred for 20 hours, poured over ice, filtered, and washed with ice water. The resulting product was slurried with cold dioxane, filtered, and dried in vacuo to provide the titled product as a white solid which was sufficiently pure for use in the next step.

Step B: 1-Triphenylmethyl-4-(acetoxymethyl)imidazole

The alcohol from Step A (260 mmol, prepared above) was suspended in pyridine (500 mL). Acetic anhydride (74 mL, 780 mmol) was added dropwise, and the reaction was stirred for 48 hours during which it became homogeneous. The solution was poured into EtOAc, washed sequentially with water, 5% aq. HCl solution, sat. aq. NaHCO$_3$, solution, and brine. The organic extracts were dried, (Na$_2$SO$_4$), and concentrated in vacuo to provide the product as a white powder, which was sufficiently pure for use in the next reaction.

Step C: 1-(4-Cyanobenzyl)-5-(acetoxymethyl)imidazole hydrobromide

A solution of the product from Step B (85.8 g, 225 mmol) and 4-cyanobenzyl bromide (50.1 g, 232 mmol) in EtOAc (500 mL) was stirred at 60° C. for 20 hours, during which a pale yellow precipitate formed. The reaction was cooled to room temperature and filtered to provide the solid imidazolium bromide salt. The filtrate was concentrated in vacuo to a volume (200 mL), heated at 60° C. for 2 hours, cooled to room temperature, and filtered. The filtrate was concentrated in vacuo to a volume (100 mL), heated at 60° C. for 2 hours, cooled to room temperature, and concentrated in vacuo to provide a pale yellow solid. All of the solid material was combined, dissolved in methanol (500 mL), and warmed to 60° C. After 2 hours, the solution was concentrated in vacuo to provide a white solid which was triturated with hexane to remove soluble by products. Removal of residual solvents in vacuo provided the titled product as a white solid which was used in the next step without further purification.

Step D: 1-(4-Cyanobenzyl)-5-(hydroxymethyl)imidazol

To a solution of the acetate from Step C (50.4 g, 150 mmol) in 3:1 THF/water (1.5 L) at 0° C. was added lithium hydroxide monohydrate (18.9 g, 450 mmol). After 1 hour, the reaction was concentrated in vacuo, diluted with EtOAc (3 L), and washed with water, sat. aq. NaHCO$_3$ and brine. The solution was then dried (Na$_2$SO$_4$), filtered, and concentrated in vacuo to provide the crude product as a pale yellow fluffy solid which was sufficiently pure for use in the next step without further purification.

Step E: 1-(4-Cyanobenzyl)-5-(chloromethyl)imidazole

A solution of 1-(4-cyanobenzyl)-5-(hydroxymethyl) imidazole (1.00 g, 4.70 mmol), in thionyl chloride (5 mL), was stirred at 70° C. for 16 hours. The solvent was evaporated in vacuo and the resulting solid suspended in CH$_2$Cl$_2$, collected by filtration and dried in vacuo. The material was sufficiently pure for use in the next step without further purification.

$^1$H NMR (CD$_3$OD 400 MHz) δ 9.06 (1H, s), 7.83(2H, d, J=8.0 Hz), 7.77(1H, s), 7.55(2H, d, J=8.0 Hz), 5.67(2H, s) and 4.78(2H, s) ppm.

Step F: 1-{[1-(4-Cyanobenzyl)-1H-imidazol-5-yl]ethyl}-4-phenyl imidazole bis hydrochloride salt To a solution of the chloride from step E (500 mg, 1.65 mmol) in DMF (10 mL) at 0° C. was added sequentially, 4-phenyl-imidazole (238 mg, 1.65 mmol) and sodium hydride (145 mg, 60% dispersion in mineral oil, 3.62 mmol). Stirring was continued at 0° C. for 1 hour and then at room temperature for 16 hours. The reaction was quenched with water (50 mL), and extracted with CH$_2$Cl$_2$. The organic extracts were dried, (MgSO$_4$), and the solvent evaporated in vacuo. The residue was purified by chromatography (Silica gel, 3–5% NH$_4$OH: acetonitrile). The imidazole was converted to the hydrochloride salt by treating an EtOAc solution of the resulting material with gasseous HCl and evaporation of the solvent in vacuo.

Anal. Calcd for C$_{21}$H$_{17}$N$_5$.2.00HCl.1.75H$_2$O.0.30EtOAc: C, 56.70; H, 5.34; N, 14.89. Found: C, 56.71; H, 5.22; N, 14.91. $^1$H NMR (CD$_3$OD 400 MHz) δ 9.32(1H, d, J=1.4 Hz), 8.87(1H, s), 8.07(1H, s), 7.69(1H, d, J=1.6 Hz), 7.60–7.45(7H, m), 7.24(2H, d, J=8.6 Hz), 5.75(2H, s) and 5.72(2H, s)ppm.

Example 3

1-{1-(4-Cyanobenzyl)-1H-imidazol-5-yl)methyl}-4-(2-methyl)phenyl imidazole bis hydrochloride salt Step A: 4-(2-Methyl)phenyl imidazole A solution of 1-(2-methyl)phenyl-2-bromoethanone (1.97 g, 9.24 mmol) in formamide (12 mL), was heated at 215° C. for 2 hours. The reaction was cooled to room temperature and 0.2M aq. HCl (120 mL) was added and the resulting solid removed by filtration. The filtrate was treated with sat. aq. NH$_4$OH to pH 10 and extracted with EtOAc . The organic extracts were washed with brine, dried, (MgSO$_4$) and evaporated in vacuo. The residue was purified by chromatography (Silica gel, EtOAc) to afford the title compound.

Step B: 1-{[1-(4-Cyanobenzyl)-1H-imidazol-5-yl]ethyl}-4-(2-methyl)phenyl)imidazole bis hydrochloride salt The title compound was prepared using the protocol described in Example 2, Step F using 4-(2-methyl)phenyl imidazole.

Anal. Calcd. for $C_{22}H_{19}N_5 \cdot 2.15HCl \cdot 1.75H_2O$. C, 57.03 H, 5.36N, 15.12. Found: C, 57.02; H, 5.35; N, 15.29. $^1H$ NMR ($CD_3OD$, 400MHz) δ 9.25(1H, s), 8.89(1H, s), 8.03 (1H, s), 7.68(2H, d, J=8.2 Hz), 7.58(1H, d, J=1.6 Hz), 7.45–7.25(6H, m), 5.76(2H, s), 5.73(2H, s) and 2.35(3H, s) ppm.

Example 4

1-(3-Phenyl-5-isoxazolylmethyl)-5-(4-cyanobenzyl) imidazole hydrochloride salt Step A: 1-Trityl-4-(4-cyanobenzyl)-imidazole To a suspension of activated zinc dust (3.57 g, 54.98 mmol) in THF (50 mL) was added dibromoethane (0.315 mL, 3.60 mmol) and the reaction stirred for 45 minutes under argon at 20° C. The suspension was cooled to 0° C. and a-bromo-p-toluinitrile (9.33 g, 47.6 mmol) in THF (100 mL) was added dropwise over a period of 10 minutes. The reaction was then allowed to stir at 20° C. for 6 hours and bis(triphenylphosphine) Nickel 11 chloride (2.4 g, 3.64 mmol) and 4-iodotritylimidazole (15.95 g, 36.6 mmol) were added in one portion. The resulting mixture was stirred 16 hours at 20° C. and then quenched by addition of saturated $NH_4Cl$ solution (100 mL) and the mixture stirred for 2 hours. Saturated aq. $NaHCO_3$ solution was added to give a pH of 8 and the solution was extracted with EtOAc (2×250 mL), dried, ($MgSO_4$) and the solvent evaporated in vacuo. The residue was chromatographed (Silica gel, 0–20% EtOAc in $CH_2Cl_2$) to afford the title compound as a white solid.

$^1H$ NMR δ $CDCl_3$ (7.54 (2H, d, J=7.9 Hz), 7.38(1H, s), 7.36–7.29 (1H, m), 7.15–7.09(6H, m), 6.58(1H, s), and 3.93(2H, s)ppm.

Step B: 1-(3-Phenyl-5-isoxazolylmethyl)-5-(4-cyanobenzyl) imidazole hydrochloride salt A suspension of 1-(bromomethyl)-3-phenylisoxazole (31.3mg, 0.13 mmol), 1-trityl-4-(4-cyanobenzyl)-imidazole (60 mg, 0.13 mmol) in acetonitrile (0.20 mL) was stirred at 55° C. for 16 hours. The solvent was evaporated in vacuo and the residue dissolved in methanol (5 mL) and stirred at reflux for 1 hour. The solvent was evaporated in vacuo and the residue partitioned between $CH_2Cl_2$, and aq. $NaHCO_3$. The organic extract was dried, ($MgSO_4$) and the solvent evaporated in vacuo. The residue was purified by chromatography (Silica gel, 0–3% MeOH in $CH_2C_2$), and converted to the hydrochloride salt by treatment with hydrochloric acid in EtOAc. Evaporation of the solvent in vacuo afforded the title compound.

Anal. Calcd. for $C_{21}H_{16}N_4O \cdot 1.00$ HCl. C, 66.93 H, 4.55 N, 14.97. Found: C, 66.84; H, 4.39; N, 14.51. $^1H$ NMR ($CD_3OD$, 400MHz) δ 9.21(1H, s), 7.51(2H, m), 7.58(2H, d, J=8.0), 7.54–7.43(4H, m), 7.33(2H, d, J=8.0 Hz), 6.62(1H, s), 5.70(2H, s) and 4.31(2H, s) ppm.

Example 5

1-(3-Phenyl-isoxazol-5-ylacetyl)-5-(4-cyanobenzyl) imidazole hydrochloride salt The title compound was prepared using the protocol described in Example 4, Step B using 5-(bromoacetyl)-3-phenyl isoxazole.

Anal. Calcd. for $C_{22}H_{16}N_4O_2 \cdot 2.55HCl \cdot 0.50H_2O$. C, 60.65 H, 4.50 N, 12.41. Found: C, 60.72; H, 4.51; N, 12.16. $^1H$ NMR ($CD_3OD$, 400 MHz) δ 8.95(1H, d, J=1.5 Hz), 8.00–7.90(2H, m), 7.73(1H, s), 7.64(2H, d, J=8.4 Hz), 7.58–7.50(3H, m), 7.48–7.40(3H, m), 5.85(2H, s), 4.23(2H, s) ppm.

Example 6

1-(4-Cyanobenzyl)-5-(4-Phenyl-thiazol-2-ylmethyl) imidazole hydrochloride salt Step A: 4-[5-(Aminocarbonylmethyl)imidazol-1-ylmethyl] benzonitrile To a 100 mL glass pressure vessel with a stirring bar was added 1-(4-cyanobenzyl)-1H-imidazol-5-yl[acetic acid methyl ester (6.00 g, 23.5 mmol) and absolute ethanol (50 mL). This well stirred solution was cooled to −78° C. and 50 mL of anhydrous ammonia was condensed in. The vessel was sealed and the mixture warmed to ambient temperature. This solution was stirred 24 hours at ambient temperature. The excess ammonia was allowed to evaporate and the ethanol was removed in vacuo. The solid residue was triturated with EtOAc and collected on a frit. This material was dried in vacuo to give the title compound as a white solid.

$^1H$ NMR (DMSO-$d_6$, 400 MHz) δ 3.25(s, 2H), 5.32(s, 2H), 6.88(s, 1H), 6.96(s,1H), 7.24(d, j=8 Hz,2H), 7.42(s, 1H), 7.68(s,1H), 7.83(d, j=8 Hz, 2H).

Step B: 1-(4-Cyanobenzyl)-1H-imidazol-5-yl] aminothiocarbonylmethyl

To a 50 mL round bottomed flask with a stirring bar, reflux condenser and an argon inlet was added 4-[5-(aminocarbonylmethyl)imidazol-1-ylmethyl]benzonitrile (0.36 g, 1.49 mmol), Lawesson's reagent (0.73 g, 1.8 mmol) and 1,4-dioxane (10 mL). This well stirred mixture was heated at 80° C. for 24 hours. The cooled reaction mixture was concentrated in vacuo and the residue was chromatographed (silica gel, 10% 2-propanol in ammonia saturated $CHCl_3$). The title compound was obtained as a yellow, crystalline solid.

$^1H$ NMR (DMSO-$d_6$, 400 MHz) 6 3.66(s, 2H), 5.41(s, 2H), 6.85(s, 1H), 7.24(d, j=8 Hz,2H), 7.70(s,1H), 7.82(d, j=8 Hz, 2H), 9.21(s, 1H), 9.56(s, 1H).

Step C: 1-(4-Cyanobenzyl)-5-(4-phenyl-thiazol-2-ylmethyl) imidazole hydrochloride salt To a 25 mL round bottomed flask with a stirring bar reflux condenser and an argon inlet was added 1-(4-Cyanobenzyl)-1H-imidazol-5-yl1aminothiocarbonylmethyl (0.12 g, 0.468 mmol), dry THF (10 mL), and a-bromoacetophenone (0.098 g, 0.491 mmol). This mixture was heated at 50° C. for 7 hours. The cooled reaction mixture was diluted with EtOAc and washed sucessively with aq. $NaHCO_3$, water, and brine. Drying ($MgSO_4$), filtration and removal of the solvent in vacuo gave a solid. This material was chromatographed (silica gel, 3% 2-propanol in ammonia saturated $CHCl_3$). The purified product was converted into the hydrochloride salt with 4M HCl in 1,4-dioxane. This material was triturated with EtAOc and collected on a frit. The product was dried in vacuo at 50° C.

mp: 245°–247° C. (HCl salt). $^1H$ NMR ($CDCl_3$, 400 MHz, free base) δ 1.70(br s, 1H), 4.23(s, 2H), 5.27(s, 2H), 7.04(d, j=8 Hz, 2H), 7.14(s,1H), 7.29(s, 1H), 7.35 (m,1H), 7.44 (m, 2H), 7.49(d, j=8 Hz, 2H), 7.56(s, 1H) and 7.78 (d, j=8 Hz, 2H) ppm.

Example 7

1-(4-Cyanobenzyl)-5-(4-(2-methylphenyl)-thiazol-2-ylmethyl)imidazole hydrobromide salt Step A: 1-(2-Methyl)phenyl-2-bromoethanone To a 500 mL round bottomed flask with a stirring bar and an argon inlet was added $CHCl_3$ (200 mL), THF (100 mL), 2-methylacetophenone (10 mL, 76.46 mmol), and pyridinium bromide perbromide (26.85 g, 84.11 mmol). This solution was stirred at ambient temperature for 24 hours.

The reaction mixture was washed with 5% aqueous HCl, H₂O, and brine. Drying (MgSO₄), filtration and removal of the solvent in vacuo gave an oil. This material was vacuum distilled at 15 torr to give 1-(2-methyl)phenyl-2-bromoethanone, bp: 143°–148° C. as a green oil.

$^1$H NMR (CDCl₃, 400 MHz) δ 2.51(s, 3H), 4.41 (s, 2H), 7.22 (m, 2H), 7.41 (m, 1H), 7.66 (d, j=7 Hz, 1H).

Step B: 1-(4-Cyanobenzyl)-5-(4-(2-methylphenyl)-thiazol-2-ylmethyl)imidazole hydrobromide salt To a 25 mL round bottomed flask with a stirring bar reflux condenser and an argon inlet was added 1-(4-cyanobenzyl)-1H-imidazol-5-yl]aminothiocarbonylmethyl (0.15 g, 0.585 mmol), dry THF (10 mL), and 1-(2-methyl)phenyl-2-bromoethanone (0.274 g, 1.28 mmol). This mixture was heated at 50° C. for 2.5 h. The cooled reaction mixture was concentrated in vacuo. The material was triturated with EtOAc and collected on a frit. The product was dried in vacuo at 50° C.

mp: 215°–216° C. (HBr salt). $^1$H NMR (DMSO-d₆) δ 2.36(s, 3H), 4.53(s, 2H), 5.63(s, 2H), 7.25(m, 3H), 7.34(d, j=8 Hz, 1H), 7.45(d, j=8 Hz, 1H), 7.62 (s, 1H), 7.70 (br s, 2H), 7.72(d, j=8 Hz, 2H), 9.15(s, 1H).

Example 8

1-(4-Cyanobenzyl)-5-(4-(3-chlorophenyl)-thiazol-2-ylmethyl)imidazole hydrochloride salt Step A: 1-(3-Chloro)phenyl-2-bromoethanone To a 100 mL round bottomed flask with a stirring bar and an argon inlet was added 3-chloroacetophenone (0.60 g, 3.85 mmol), CHCl₃ (20 mL), and benzyltrimethylammonium bromide perbromide (180 g, 4.62 mmol). This suspension stirred at ambient temperature for 48 hours. The reaction mixture was diluted with EtOAc and this solution was washed with H₂O and brine. Drying (MgSO₄), filtration and removal of the solvent gave an oil. This material was chromatographed (Silica gel, 5% EtOAc in hexanes). The title compound was obtained as an oil.

$^1$H NMR (CDCl₃, 400 MHz) δ 4.42(s, 2H), 7.47 (t, j=8 Hz, 1H), 7.58 (d, j=8 Hz, 1H), 7.86 (d, j=8 Hz, 1H) and 7.97 (s, 1H) ppm.

Step B: 1-(4-Cyanobenzyl)-5-(4-(3-chlorophenyl)-thiazol-2-ylmethyl)imidazole hydrochloride salt To a 50 mL round bottomed flask with a stirring bar, reflux condenser and an argon inlet, was added 1-(4-cyanobenzyl)-1H-imidazol-5-yl]aminothiocarbonylmethyl (0.15 g, 0.585 mmol), THF (10 mL), and 1-(3-chloro)phenyl-2-bromoethanone (0.18 g, 0.77 mmol). This mixture was heated at 50° C. for 3 hours. The cooled mixture was concentrated in vacuo and the residue was partitioned between EtOAc and aq. NaHCO₃ solution. The layers were separated and the organic phase was washed with brine, dried, (MgSO₄) filtered and concentrated in vacuo. This material was chromatographed (Silica gel, 2% CH₃OH in EtOAc). The main chromatographic product was repurified by liquid chromatogrphy (0.1% TFA in H₂O:CH₃CN—gradient 95:5 to 5:95) to provide two compounds as TFA salts. The TFA salt material thus obtained was converted into the HCl salts with 4M HCl in 1,4-dioxane. The title compound, isolated as the major component, was triturated with EtOAc and collected on a frit. The product was dried in vacuo at 50° C. mp: 245°–246° C.

$^1$H NMR (DMSO-d₆, free base) δ 4.56(s, 2H), 5.67(s, 2H), 7.32(d, j=8 Hz, 2H), 7.43(m, 2H), 7.65(d, j=8 Hz, 2H), 7.74 (br s,1H), 7.80 (br s, 1H), 8.11(s, 1H), 9.33(s, 1H).

The minor component was isolated: (3-{4-[4-(3-chlorophenyl)-thiazol-2-yl]-3-H-imidazol-4-yl)acetonitrile, hydrochloride.

mp:219°–220° C. $^1$H NMR (DMSO-d₆) δ 4.18(s, 2H), 5.49(s, 2H), 7.43(d, j=8.3 Hz, 2H), 7.48(d, j=7.5 Hz, 2H), 7.63(s, 1H), 7.99(d, j=7.5 Hz, 2H), 8.05(d, j=8.3 Hz, 2H), 8.35(s, 1H), 8.97(br s, 1H).

Example 9

1-(4-Cyanobenzyl)-5-(4-(naphth-2-yl)-thiazol-2-ylmethyl)imidazole hydrochloride salt To a 35 mL round bottomed flask with a stirring bar, condenser and an argon inlet was added 1-(4-cyanobenzyl)-1H-imidazol-5-yl]aminothiocarbonylmethyl (0.15 g, 0.585 mmol), THF (10 mL), and 1-(2-naphthalenyl)-2-bromoethanone (0.175 g, 0.70 mmol). The well stirred mixture was heated at 50° C. for 2 hours. The mixture was cooled to room temperature and allowed to stir over night. The solvent was removed in vacuo and the residue was partitioned between EtOAc and aq. NaHCO₃ solution. The layers were separated and the organic phase was washed with H₂O and brine. Drying (MgSO₄), filtration and removal of the solvent in vacuo gave an oil. This material was chromatographed (Silica gel, 2% 2-propanol in ammonia saturated CHCl₃). The product was converted into the hydrochloride salt with 4M HCl in 1,4-dioxane. The HCl salt was triturated with EtOAc and collected on a frit. The product was dried in vacuo at 50° C. for 24 hours. mp: 245°–246° C.

$^1$H NMR (DMSO-d₆, 400 MHz, free base)δ 4.57(s, 2H), 5.68(s, 2H), 7.36(d, j=8 Hz, 2H), 7.52(m, 2H), 7.68(d, j=8 Hz, 2H), 7.74(br s, 1H), 7.96 (m, 3H), 8.11(s, 1H), 8.35(s, 1H) and 9.22(s, 1H) ppm.

Example 10

1-((4-(2-methylphenyl)-5-methylthiazole-2-ylmethyl)-5-(4-cyanobenzyl) imidazole hydrochloride salt Step A: 1-o-Tolyl-propan-1-one To an oven dried 100 ml 3 neck flask equipped with septa, thermo probe and stirred bar was stirring a solution of o-tolunitrile (1 ml, 8.5 mmol) in 40 ml dry THF at 0° C. To this cold, well stirred solution was added a solution of ethylmagnesium bromide (17 ml, 17 mmol) in THF via syringe while keeping the temperature below 5° C. Removed ice bath and allowed the yellow solution to stir at ambient temperature for 24 h. The reaction was cooled to 0° C. and quenched with a solution of saturated NH₄Cl (50 ml), extracted with 2x EtOAc and washed with H₂O, brine, drying (MgSO₄), filtration and removal of solvent in vacuo to give a crude oil. This material was chromatographed (Silica gel, 3% EtOAc/Hexane) to affort the title product.

$^1$H NMR (CDCl₃, 300 MHz) δ 1.17(t, 3H), 2.31(s, 3H), 2.6(q, 2H), 7.15–7.26(m, 4H)

Step B: 2-Bromo-1-o-tolyl-propan-1-one

To a 50 ml round bottomed flask with stirring bar and an argon inlet was added CH₃Cl (10 ml), THF (5 ml), 1-o-tolyl-propan-1-one (318 mg, 2.14 mmol, and pyridium bromide perbromide (735 mg, 2.36 mmol). This solution was stirred at ambient temperature for 2 h. The reaction mixture was washed with 5% aqueous HCl, H₂O, and brine. Drying (MgSO₄), filtration and removal of sovent in vacuo gave an oil. This material was chromatographed (Silica gel, 5% EtOAc/Hexane) to affort the title product.

$^1$H NMR (CDCl₃, 400 MHz) δ 1.88(d, J=6.7 Hz, 3H), 2.5(s, 3H), 5.20(q, I H), 7.25–7.29(m, 2H), 7.38(m, 1H), 7.61 (d, J=7.14 Hz, 1H).

Step C: 1-((4-(2-methylphenyl)-5-methylthiazole-2-ylmethyl)-5-(4-cyanobenzyl)imidazole hydrochloride salt To a 100 mL round bottomed flask with a stirring bar, refluxed condenser and an argon inlet was added 1-(4-cyanobenzyl)-1H-imidazol-5-yl]aminothiocarbonylmethyl (0.68, 2.65 mmol), THF (30 mL), and 2-Bromo-1-o-tolyl-propan-1-one (1.2 g, 5.3 mmol). The well stirred mixture was heated at 60° C. for 96 hours. The cooled mixture was concentrated in vacuo and the residue was partitioned between EtOAc and aq. NaHCO$_3$ solution. The layers were separated and the organic phase was washed with H$_2$O and brine. Drying (MgSO$_4$), filtration and removal of the solvent in vacuo gave an oil. This material was chromatographed (Silica gel, 2% 2-propanol in ammonia saturated CHCl$_3$). The main chromatographic product was repurified by liquid chromatogrphy (0.1% TFA in H$_2$O:CH$_3$CN—gradient 95:5 to 5:95) to provide two compounds as TFA salts. The TFA salt material thus obtained was converted into the HCl salts with 4M HCl in 1,4-dioxane. The title compound, isolated as the major component, was triturated with ether and collected on a frit. The product was dried in vacuo at 50° C. mp:108°–110° C.

$^1$H NMR (DMSO-d$_6$, 400 MHz) δ 2.07(s, 3H), 2.19(s, 3H), 4.44(s, 2H), 7.11(d, J=7.3 Hz, 1H), 7.23–7.30(m, 3H), 7.38(d,J=8.2 Hz, 2H), 7.70 (s, 1H), 7.78(d, J=8.0 Hz, 2H), 9.28(br s, 1H).

Example 11

1-((4-(2-methylphenyl)thiazole-2-ylethyl)-5-(4-cyanobenzyl) imidazole hydrochloride salt The title compound was prepared using the protocol described in example 1 steps A–C, where step A was a standard reduction of urocanic acid and then Fisher esterification to provide the methyl-ester in step C. The title compound was prepared using the procedures described in example 8 steps A and B.

$^1$H NMR (CDCl$_3$, 400 MHz) δ 2.37(s,1H), 3.18(br s, 2H), 3.46(br s, 2H), 5.71(br s,2H), 7.20(s,1H), 7.27–7.34(m, 4H), 7.38(d, J=6.95 Hz, 2H), 7.49(d, J=7.14, 1H), 7.60(d, J=7.32, 2H) 9.69(br s, 1H). Anal. Calcd. for C$_{23}$H$_{20}$N$_4$S.2.0HCl.1.50H$_2$O. C, 57.03; H, 5.20; N, 11.57. Found: C, 56.86; H, 4.99; N, 11.95.

Example 1012

In vitro inhibition of ras farnesyl transferase
Assays of farnesyl-protein transferase.

Partially purified bovine FPTase and Ras peptides (Ras-CVLS, Ras-CVIM and Ras-CAIL) were prepared as described by Schaber et al., *J. Biol. Chem.* 265:14701–14704 (1990), Pompliano, et al., *Biochemistry* 31:3800 (1992) and Gibbs et al., *PNAS U.S.A.* 86:6630–6634 (1989), respectively. Bovine FPTase was assayed in a volume of 100 μl containing 100 mM N-(2-hydroxy ethyl) piperazine-N'-(2-ethane sulfonic acid) (HEPES), pH 7.4, 5 mM MgCl$_2$, 5 mM dithiothreitol (DTT), 100 mM [$^3$H]-farnesyl diphosphate ([$^3$H]-FPP; 740 CBq/mmol, New England Nuclear), 650 nM Ras-CVLS and 10 μg/ml FPTase at 31° C. for 60 min. Reactions were initiated with FPTase and stopped with 1 ml of 1.0M HCL in ethanol. Precipitates were collected onto filter-mats using a TomTec Mach 11 cell harvester, washed with 100% ethanol, dried and counted in an LKB β-plate counter. The assay was linear with respect to both substrates, FPTase levels and time; less than 10% of the [$^3$H]-FPP was utilized during the reaction period. Purified compounds were dissolved in 100% dimethyl sulfoxide (DMSO) and were diluted 20-fold into the assay. Percentage inhibition is measured by the amount of incorporation of radioactivity in the presence of the test compound when compared to the amount of incorporation in the absence of the test compound.

Human FPTase was prepared as described by Omer et al., *Biochemistry* 32:5167–5176 (1993). Human FPTase activity was assayed as described above with the exception that 0.1% (w/v) polyethylene glycol 20,000, 10 μM ZnCl$_2$ and 100 nM Ras-CVIM were added to the reaction mixture. Reactions were performed for 30 min., stopped with 100 μl of 30% (v/v) trichloroacetic acid (TCA) in ethanol and processed as described above for the bovine enzyme.

The compounds of the instant invention described in the above Examples 1–11 were tested for inhibitory activity against human FPTase by the assay described above and were found to have IC$_{50}$ of 50 μM.

Example 13

In vivo ras farnesylation assay

The cell line used in this assay is a v-ras line derived from either Rat1 or NIH3T3 cells, which expressed viral Ha-ras p21. The assay is performed essentially as described in DeClue, J. E. et al., *Cancer Research* 51:712–717, (1991). Cells in 10 cm dishes at 50–75% confluency are treated with the test compound (final concentration of solvent, methanol or dimethyl sulfoxide, is 0.1%). After 4 hours at 37° C., the cells are labelled in 3 ml methionine-free DMEM supplemeted with 10% regular DMEM, 2% fetal bovine serum and 400 mCi[$^{35}$S]methionine (1000 Ci/mmol). After an additional 20 hours, the cells are lysed in 1 ml lysis buffer (1% NP40/20 mM HEPES, pH 7.5/5 mM MgCl$_2$/1 mM DTT/10 mg/ml aprotinen/2 mg/ml leupeptin/2 mg/ml antipain/0.5 mM PMSF) and the lysates cleared by centrifugation at 100,000×g for 45 min. Aliquots of lysates containing equal numbers of acid-precipitable counts are bought to 1 ml with IP buffer (lysis buffer lacking DTT) and immunoprecipitated with the ras-specific monoclonal antibody Y13–259 (Furth, M. E. et al., *J. Virol.* 43:294–304, (1982)). Following a 2 hour antibody incubation at 4° C., 200 ml of a 25% suspension of protein A-Sepharose coated with rabbit anti rat IgG is added for 45 min. The immunoprecipitates are washed four times with IP buffer (20 nM HEPES, pH 7.5/1 mM EDTA/1% Triton X-100.0.5% deoxycholate/0.1%/SDS/0.1M NaCI) boiled in SDS-PAGE sample buffer and loaded on 13% acrylamide gels. When the dye front reached the bottom, the gel is fixed, soaked in Enlightening, dried and autoradiographed. The intensities of the bands corresponding to farnesylated and nonfarnesylated ras proteins are compared to determine the percent inhibition of farnesyl transfer to protein.

Example 14

In vivo growth inhibition assay

To determine the biological consequences of FPTase inhibition, the effect of the compounds of the instant invention on the anchorage-independent growth of Rat1 cells transformed with either a v-ras, v-raf, or v-mos oncogene is tested. Cells transformed by v-Raf and v-Mos maybe included in the analysis to evaluate the specificity of instant compounds for Ras-induced cell transformation.

Rat 1 cells transformed with either v-ras, v-raf, or v-mos are seeded at a density of 1×10$^4$ cells per plate (35 mm in diameter) in a 0.3% top agarose layer in medium A (Dulbecco's modified Eagle's medium supplemented with 10% fetal bovine serum) over a bottom agarose layer (0.6%). Both layers contain 0.1% methanol or an appropriate concentration of the instant compound (dissolved in methanol at 1000 times the final concentration used in the assay). The cells are fed twice weekly with 0.5 ml of medium A containing 0% methanol or the concentration of the instant compound. Photomicrographs are taken 16 days after the cultures are seeded and comparisons are made.

What is claimed is:

1. A compound which inhibits farnesyl-protein transferase of the formula A:

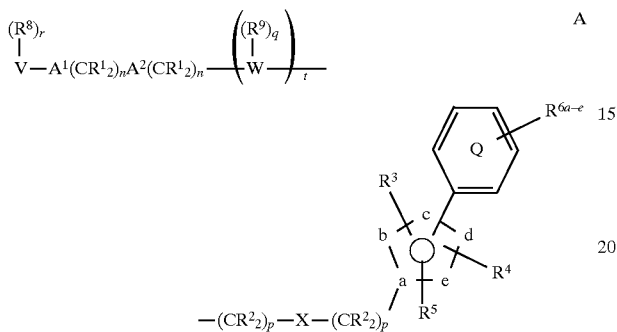

wherein:

a is N or C;

from 0–4 of b, c, d and e are independently N, NH, O and S, and the remaining b, c, d and e atoms are independently CH, provided that if a is C, then at least one of b, c, d or e is independently N, NH, O or S;

$R^1$ and $R^2$ are independently selected from:
a) hydrogen,
b) aryl, heterocycle, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $R^{11}C(O)O$—, $(R^{10})_2NC(O)$—, $R^{10}_2N$—C$(NR^{10})$—, CN, $NO_2$, $R^{10}C(O)$—, $N_3$, —$N(R^{10})_2$, or $R^{11}OC(O)NR^{10}$—,
c) unsubstituted or substituted $C_1$–$C_6$ alkyl wherein the substituent on the substituted $C_1$–$C_6$ alkyl is selected from unsubstituted or substituted aryl, heterocyclic, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2NC(O)$—, $R^{10}_2N$—C$(NR^{10})$—, CN, $R^{10}C(O)$—, $N_3$, —$N(R^{10})_2$, and $R^{11}OC(O)$—$NR^{10}$—;

$R^3$, $R^4$ and $R^5$ are independently selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}C(O)O$—, $R^{11}S(O)_m$—, $R^{10}C(O)NR^{10}$—, $(R^{10})_2NC(O)$—, $R^{10}_2N$—C$(NR^{10})$—, CN, $NO_2$, $R^{10}C(O)$—, $N_3$, —$N(R^{10})_2$, or $R^{11}OC(O)NR^{10}$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{10}_2N$—C$(NR^{10})$—, CN, $R^{10}C(O)$—, $N_3$, —$N(R^{10})_2$, and $R^{11}OC(O)$—$NR^{10}$—;

$R^{6a}$, $R^{6b}$, $R^{6c}$, $R^{6d}$ and $R^{6e}$ are independently selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $R^{11}C(O)O$—, $R^{10}_2N$—C$(NR^{10})$—, CN, $NO_2$, $R^{10}C(O)$—, $N_3$, —$N(R^{10})_2$, or $R^{11}OC(O)NR^{10}$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{10}_2N$—C$(NR^{10})$—, CN, $R^{10}C(O)$—, $N_3$, —$N(R^{10})_2$, and $R^{11}OC(O)$—$NR^{10}$—; or any two of $R^{6a}$, $R^{6b}$, $R^{6c}$, $R^{6d}$ and $R^{6e}$ on adjacent carbon atoms are combined to form a diradical selected from —CH=CH—CH=CH—, —CH=CH—$CH_2$—, —$(CH_2)_4$— and —$(CH_2)_3$—;

provided that when $R^{6a}$, $R^{6b}$, $R^{6c}$, $R^{6d}$ or $R^{6e}$ is unsubstituted or substituted heterocycle, attachment of $R^{6a}$, $R^{6b}$, $R^{6c}$, $R^{6d}$ or $R^{6e}$ to Q is through a ring carbon;

$R^7$ is selected from: H; $C_{1-4}$ alkyl, $C_{3-6}$ cycloalkyl, heterocycle, aryl, aroyl, heteroaroyl, arylsulfonyl, heteroarylsulfonyl, unsubstituted or substituted with:
a) $C_{1-4}$ alkoxy,
b) aryl or heterocycle,
c) halogen,
d) HO,
e)

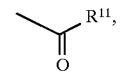

f) —$SO_2R^{11}$
g) $N(R^{10})_2$ or
h) $C_{1-4}$ perfluoroalkyl;

$R^8$ is independently selected from:
a) hydrogen,
b) aryl, substituted aryl, heterocycle, $C_3$–$C_{10}$ cycloalkyl, $C_2$–$C_6$ alkenyl, $C_2$–$C_6$ alkynyl, perfluoroalkyl, F, Cl, Br, $R^{10}O$—, $R^{11}S(O)_m$—, $R^{10}C(O)NR^{10}$—, $(R^{10})_2NC(O)$—, $R^{10}_2N$—C$(NR^{10})$—, CN, $NO_2$, $R^{10}C(O)$—, $N_3$, —$N(R^{10})_2$, or $R^{11}OC(O)NR^{10}$—, and
c) $C_1$–$C_6$ alkyl unsubstituted or substituted by aryl, cyanophenyl, heterocycle, $C_3$–$C_{10}$ cycloalkyl, $C_2$–$C_6$ alkenyl, $C_2$–$C_6$ alkynyl, perfluoroalkyl, F, Cl, Br, $R^{10}O$—, $R^{11}S(O)_m$—, $R^{10}C(O)NH$—, $(R^{10})_2NC(O)$—, $R^{10}_2N$—C$(NR^{10})$—, CN, $R^{10}C(O)$—, $N_3$, —$N(R^{10})_2$, or $R^{10}OC(O)NH$—;

provided that when $R^8$ is heterocycle, attachment of $R^8$ to V is through a ring carbon;

$R^9$ is independently selected from:
a) hydrogen,
b) $C_2$–$C_6$ alkenyl, $C_2$–$C_6$ alkynyl, $C_1$–$C_6$ perfluoroalkyl, F, Cl, Br, $R^{11}O$—, $R^{11}S(O)_m$—, $R^{10}C(O)NR^{10}$—, $(R^{10})_2NC(O)$—, $R^{10}_2N$—C$(NR^{10})$—, CN, $NO_2$, $R^{10}C(O)$—, $N_3$, —$N(R^{10})_2$, or $R^{11}OC(O)NR^{10}$—, and
c) $C_1$–$C_6$ alkyl unsubstituted or substituted by $C_1$–$C_6$ perfluoroalkyl, F, Cl, Br, $R^{10}O$—, $R^{11}S(O)_m$—, $R^{10}C(O)NR^{10}$—, $(R^{10})_2NC(O)$—, $R^{10}_2N$—C$(NR^{10})$—, CN, $R^{10}C(O)$—, $N_3$, —$N(R^{10})_2$, or $R^{11}OC(O)NR^{10}$—;

$R^{10}$ is independently selected from hydrogen, $C_1$–$C_6$ alkyl, benzyl, 2,2,2-trifluoroethyl and aryl;

$R^{11}$ is independently selected from $C_1$–$C_6$ alkyl and aryl;

$R^{12}$ is independently selected from hydrogen, $C_1$–$C_6$ alkyl, $C_1$–$C_6$ aralkyl, $C_1$–$C_6$ substituted aralkyl, $C_1$–$C_6$ heteroaralkyl, $C_1$–$C_6$ substituted heteroaralkyl, aryl, substituted aryl, heteroaryl, substituted heteroaryl, $C_1$–$C_6$ perfluoroalkyl, 2-aminoethyl and 2,2,2-trifluoroethyl;

$A^1$ and $A^2$ are independently selected from: a bond, —CH=CH—, —C≡C—, —C(O)—, —C(O)NR$^{10}$—, —NR$^{10}$C(O)—, O, —N(R$^{10}$)—, —S(O)$_2$N(R$^{10}$)—, —N(R$^{10}$)S(O)$_2$—, or S(O)$_m$;

V is selected from:
  a) hydrogen,
  b) heterocycle,
  c) aryl,
  d) $C_1$–$C_{20}$ alkyl wherein from 0 to 4 carbon atoms are replaced with a heteroatom selected from O, S, and N, and
  e) $C_2$–$C_{20}$ alkenyl,
provided that V is not hydrogen if $A^1$ is S(O)$_m$ and V is not hydrogen if $A^1$ is a bond, n is 0 and $A^2$ is S(O)$_m$; provided that when V is heterocycle, attachment of V to $R^8$ and to $A^1$ is through a ring carbon;

W is a heterocycle;

X is a bond, —CH=CH—, O, —C(=O)—, —C(O)NR$^7$—, —NR$^7$C(O)—, —C(O)O—, —OC(O)—, —C(O)NR$^7$C(O)—, —NR$^7$—, —S(O)$_2$N(R$^{10}$)—, —N(R$^{10}$)S(O)$_2$— or —S(=O)$_m$—, provided that if a is N, then X is not O, —C(O)NR$^7$—, —C(O)O—, —C(O)NR$^7$C(O)—, —S(O)$_2$N(R$^{10}$)— or —NR$^7$—;

m is 0, 1 or 2;

n is independently 0, 1, 2, 3 or 4;

p is independently 0, 1, 2, 3 or 4;

q is 0, 1, 2 or 3;

r is 0 to 5, provided that r is 0 when V is hydrogen; and t is 0 or 1;

or a pharmaceutically acceptable salt thereof.

2. The compound according to claim 1 of the formula A:

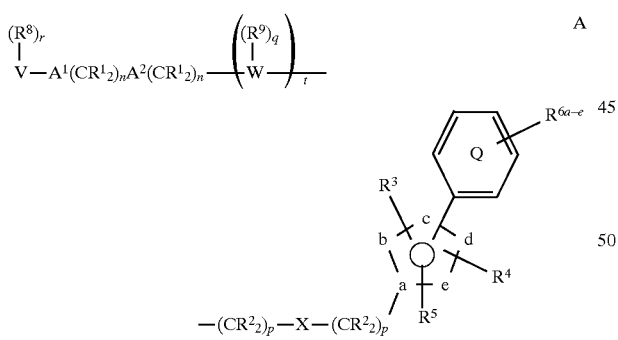

wherein:
  a is N or C;
  from 0–4 of b, c, d and e are independently N, NH, O and S, and the remaining b, c, d and e atoms are independently CH, provided that if a is C, then at least one of b, c, d or e is independently N, NH, O or S;

$R^1$ is independently selected from: hydrogen, $C_3$–$C_{10}$ cycloalkyl, $R^{10}$O—, —N(R$^{10}$)$_2$, F or $C_1$–$C_6$ alkyl;

$R^2$ is independently selected from:
  a) hydrogen,
  b) aryl, heterocycle, $C_3$–$C_{10}$ cycloalkyl, $R^{10}$O—, —N(R$^{10}$)$_2$, F or $C_2$–$C_6$ alkenyl,
  c) unsubstituted or substituted $C_1$–$C_6$ alkyl wherein the substituent on the substituted $C_1$–$C_6$ alkyl is selected from unsubstituted or substituted aryl, heterocycle, $C_3$–$C_{10}$ cycloalkyl, $C_2$–$C_6$ alkenyl, $R^{10}$O— and —N(R$^{10}$)$_2$;

$R^3$, $R^4$ and $R^5$ are independently selected from:
  a) hydrogen,
  b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}$O—, $R^{11}$S(O)$_m$—, $R^{10}$C(O)NR$^{10}$—, (R$^{10}$)$_2$NC(O)—, $R^{10}$$_2$N—C(NR$^{10}$)—, CN, NO$_2$, $R^{10}$C(O)—, N$_3$, —N(R$^{10}$)$_2$, or $R^{11}$OC(O)NR$^{10}$—,
  c) unsubstituted $C_1$–$C_6$ alkyl;
  d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}$O—, $R^{11}$S(O)$_m$—, $R^{10}$C(O)NR$^{10}$—, (R$^{10}$)$_2$NC(O)—, $R^{10}$$_2$N—C(NR$^{10}$)—, CN, $R^{10}$C(O)—, N$_3$, —N(R$^{10}$)$_2$, and $R^{11}$OC(O)—NR$^{10}$—;

$R^{6a}$, $R^{6b}$, $R^{6c}$, $R^{6d}$ and $R^{6e}$ are independently selected from:
  a) hydrogen,
  b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}$O—, $R^{11}$S(O)$_m$—, $R^{10}$C(O)NR$^{10}$—, (R$^{10}$)$_2$NC(O)—, $R^{10}$$_2$N—C(NR$^{10}$)—, CN, NO$_2$, $R^{10}$C(O)—, N$_3$, —N(R$^{10}$)$_2$, or $R^{11}$OC(O)NR$^{10}$—,
  c) unsubstituted $C_1$–$C_6$ alkyl;
  d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}$O—, $R^{11}$S(O)$_m$—, $R^{10}$C(O)NR$^{10}$—, (R$^{10}$)$_2$NC(O)—, $R^{10}$$_2$N—C(NR$^{10}$)—, CN, $R^{10}$C(O)—, N$_3$, —N(R$^{10}$)$_2$, and $R^{11}$OC(O)—NR$^{10}$—; or any two of $R^{6a}$, $R^{6b}$, $R^{6c}$, $R^{6d}$ and $R^{6e}$ on adjacent carbon atoms are combined to form a diradical selected from —CH=CH—CH=CH—, —CH=CH—CH$_2$—, —(CH$_2$)$_4$— and —(CH$_2$)$_3$—;
provided that when $R^{6a}$, $R^{6b}$, $R^{6c}$, $R^{6d}$ or $R^{6e}$ is unsubstituted or substituted heterocycle, attachment of $R^{6a}$, $R^{6b}$, $R^{6c}$, $R^{6d}$ or $R^{6e}$ to Q is through a ring carbon;

$R^7$ is selected from: H; $C_{1-4}$ alkyl, $C_{3-6}$ cycloalkyl, heterocycle, aryl, aroyl, heteroaroyl, arylsulfonyl, heteroarylsulfonyl, unsubstituted or substituted with:
  a) $C_{1-4}$ alkoxy,
  b) aryl or heterocycle,
  c) halogen,
  d) HO,
  e) 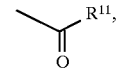
  f) —SO$_2$R$^{11}$
  g) N(R$^{10}$)$_2$ or
  h) $C_{1-4}$ perfluoroalkyl;

$R^8$ is independently selected from:
  a) hydrogen, b) aryl, substituted aryl, heterocycle, $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, —$N(R^{10})_2$, or $R^{11}OC(O)NR^{10}$—, and c) $C_1$–$C_6$ alkyl substituted by $C_1$–$C_6$ perfluoroalkyl, $R^{10}O$—, $R^{10}C(O)NR^{10}$—, $(R^{10})_2N$—$C(NR^{10})$—, $R^{10}C(O)$—, —$N(R^{10})_2$, or $R^{11}OC(O)NR^{10}$—;

provided that when $R^8$ is heterocycle, attachment of $R^8$ to V is through a carbon;

$R^9$ is selected from:
a) hydrogen,
b) $C_2$–$C_6$ alkenyl, $C_2$–$C_6$ alkynyl, $C_1$–$C_6$ perfluoroalkyl, F, Cl, $R^{11}O$—, $R^{11}S(O)_m$—, $R^{10}C(O)NR^{10}$—, $(R^{10})_2NC(O)$—, CN, $NO_2$, $(R^{10})_2N$—$C(NR^{10})$—, $R^{10}C(O)$—, —$N(R^{10})_2$, or $R^{11}OC(O)NR^{10}$—, and
c) $C_1$–$C_6$ alkyl unsubstituted or substituted by $C_1$–$C_6$ perfluoroalkyl, F, Cl, $R^{10}O$—, $R^{11}S(O)_m$—, $R^{10}C(O)NR^{10}$—, $(R^{10})_2NC(O)$—, CN, $(R^{10})_2N$—$C(NR^{10})$—, $R^{10}C(O)$—, —$N(R^{10})_2$, or $R^{11}OC(O)NR^{10}$—;

$R^{10}$ is independently selected from hydrogen, $C_1$–$C_6$ alkyl, benzyl, 2,2,2-trifluoroethyl and aryl;

$R^{11}$ is independently selected from $C_1$–$C_6$ alkyl and aryl;

$R^{12}$ is independently selected from hydrogen, $C_1$–$C_6$ alkyl, $C_1$–$C_6$ aralkyl, $C_1$–$C_6$ substituted aralkyl, $C_1$–$C_6$ heteroaralkyl, $C_1$–$C_6$ substituted heteroaralkyl, aryl, substituted aryl, heteroaryl, substituted heteroaryl, $C_1$–$C_6$ perfluoroalkyl, 2-aminoethyl and 2,2,2-trifluoroethyl;

$A^1$ and $A^2$ are independently selected from: a bond, —CH=CH—, —C≡C—, —C(O)—, —C(O)NR$^{10}$—, O, —N(R$^{10}$)—, or S(O)$_m$;

V is selected from:
a) hydrogen,
b) heterocycle selected from pyrrolidinyl, imidazolyl, imidazolinyl, pyridinyl, thiazolyl, oxazolyl, indolyl, quinolinyl, isoquinolinyl, triazolyl and thienyl,
c) aryl,
d) $C_1$–$C_{20}$ alkyl wherein from 0 to 4 carbon atoms are replaced with a heteroatom selected from O, S, and N, and
e) $C_2$–$C_{20}$ alkenyl, and
provided that V is not hydrogen if $A^1$ is S(O)$_m$ and V is not hydrogen if $A^1$ is a bond, n is 0 and $A^2$ is S(O)$_m$;
provided that when V is heterocycle, attachment of V to $R^8$ and to $A^1$ is through a ring carbon;

W is a heterocycle selected from pyrrolidinyl, imidazolyl, imidazolinyl, pyridinyl, thiazolyl, oxazolyl, indolyl, quinolinyl, triazolyl or isoquinolinyl;

X is a bond, O, —C(=O)—, —CH=CH—, —C(O)NR$^7$—, —NR$^7$C(O)—, —NR$^7$—, —S(O)$_2$N(R$^{10}$)—, —N(R$^{10}$)S(O)$_2$— or —S(=O)$_m$—; provided that if a is N, then X is not O, —C(O)NR$^7$—,—S(O)$_2$N(R$^{10}$)—or —NR$^7$—;

m is 0, 1 or 2;
n is independently 0, 1, 2, 3 or 4;
p is independently 0, 1, 2, 3 or 4;
q is 0, 1, 2 or 3;
r is 0 to 5, provided that r is 0 when V is hydrogen; and
t is 0 or 1;
or a pharmaceutically acceptable salt thereof.

3. The compound according to claim 1 of the formula B:

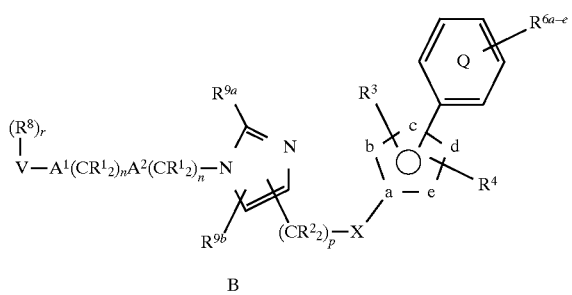

B wherein:
a is N or C;
from 0–4 of b, c, d and e are independently N, NH, O and S, and the remaining b, c, d and e atoms are independently CH, provided that if a is C, then at least one of b, c, d or e is independently N, NH, O or S;

$R^1$ is independently selected from: hydrogen, $C_3$–$C_{10}$ cycloalkyl, $R^{10}O$—, —$N(R^{10})_2$, F or $C_1$–$C_6$ alkyl;

$R^2$ is independently selected from:
a) hydrogen,
b) aryl, heterocycle, $C_3$–$C_{10}$ cycloalkyl, $R^{10}O$—, —$N(R^{10})_2$, F or $C_2$–$C_6$ alkenyl,
c) unsubstituted or substituted $C_1$–$C_6$ alkyl wherein the substituent on the substituted $C_1$–$C_6$ alkyl is selected from unsubstituted or substituted aryl, heterocycle, $C_3$–$C_{10}$ cycloalkyl, $C_2$–$C_6$ alkenyl, $R^{10}O$— and —$N(R^{10})_2$;

$R^3$ and $R^4$ are independently selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $R^{10}_2N$—$C(NR^{10})$—, CN, $NO_2$, $R^{10}C(O)$—, $N_3$, —$N(R^{10})_2$, or $R^{11}OC(O)NR^{10}$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{10}_2N$—$C(NR^{10})$—, CN, $R^{10}C(O)$—, $N_3$, —$N(R^{10})_2$, and $R^{11}OC(O)NR^{10}$—;

$R^{6a}$, $R^{6b}$, $R^{6c}$, $R^{6d}$ and $R^{6e}$ are independently selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $R^{10}_2N$—$C(NR^{10})$—, CN, $NO_2$, $R^{10}C(O)$—, $N_3$, —$N(R^{10})_2$, or $R^{11}OC(O)NR^{10}$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{10}_2N$—$C(NR^{10})$—, CN, $R^{10}C(O)$—, $N_3$, —$N(R^{10})_2$, and $R^{11}OC(O)NR^{10}$—; or any two of $R^{6a}$, $R^{6b}$, $R^{6c}$, $R^{6d}$ and $R^{6e}$ on adjacent carbon atoms are combined to form a diradical selected from —CH=CH—CH=CH—, —CH=CH—CH$_2$—, —(CH$_2$)$_4$— and —(CH$_2$)$_3$—;

provided that when $R^{6a}$, $R^{6b}$, $R^{6c}$, $R^{6d}$ or $R^{6e}$ is unsubstituted or substituted heterocycle, attachment of $R^{6a}$, $R^{6b}$, $R^{6c}$, $R^{6d}$ or $R^{6e}$ to Q is through a ring carbon;

$R^8$ is independently selected from:
  a) hydrogen,
  b) aryl, substituted aryl, heterocycle, $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, NO$_2$, $(R^{10})_2$N—C(NR$^{10}$)—, $R^{10}C(O)$—, —N$(R^{10})_2$, or $R^{11}OC(O)NR^{10}$—, and
  c) $C_1$–$C_6$ alkyl substituted by $C_1$–$C_6$ perfluoroalkyl, $R^{10}O$—, $R^{10}C(O)NR^{10}$—, $(R^{10})_2$N—C(NR$^{10}$)—, $R^{10}C(O)$—, —N$(R^{10})_2$, or $R^{11}OC(O)NR^{10}$—;

provided that when $R^8$ is heterocycle, attachment of $R^8$ to V is through a ring carbon;

$R^{9a}$ and $R^{9b}$ are independently hydrogen, $C_1$–$C_6$ alkyl, trifluoromethyl and halogen;

$R^{10}$ is independently selected from hydrogen, $C_1$–$C_6$ alkyl, benzyl, 2,2,2-trifluoroethyl and aryl;

$R^{11}$ is independently selected from $C_1$–$C_6$ alkyl and aryl;

$R^{12}$ is independently selected from hydrogen, $C_1$–$C_6$ alkyl, $C_1$–$C_6$ aralkyl, $C_1$–$C_6$ substituted aralkyl, $C_1$–$C_6$ heteroaralkyl, $C_1$–$C_6$ substituted heteroaralkyl, aryl, substituted aryl, heteroaryl, substituted heteroaryl, $C_1$–$C_6$ perfluoroalkyl, 2-aminoethyl and 2,2,2-trifluoroethyl;

$A^1$ and $A^2$ are independently selected from: a bond, —CH=CH—, —C≡C—, —C(O)—, —C(O)NR$^{10}$—, O, —N$(R^{10})$—, or S(O)$_m$;

V is selected from:
  a) hydrogen,
  b) heterocycle selected from pyrrolidinyl, imidazolyl, imidazolinyl, pyridinyl, thiazolyl, oxazolyl, indolyl, quinolinyl, isoquinolinyl, triazolyl and thienyl,
  c) aryl,
  d) $C_1$–$C_{20}$ alkyl wherein from 0 to 4 carbon atoms are replaced with a heteroatom selected from O, S, and N, and
  e) $C_2$–$C_{20}$ alkenyl, and provided that V is not hydrogen if $A^1$ is S(O)$_m$ and V is not hydrogen if $A^1$ is a bond, n is 0 and $A^2$ is S(O)$_m$;

provided that when V is heterocycle, attachment of V to $R^8$ and to $A^1$ is through a ring carbon;

X is a bond, —CH=CH—, —C(O)NR$^{10}$—, —NR$^{10}$C(O)—, —NR$^{10}$—, O or —C(=O)—;

provided that if a is N, then X is not —C(O)NR$^{10}$—, —NR$^{10}$— or O ;

m is 0, 1 or 2;

n is independently 0, 1, 2, 3 or 4;

p is 0, 1, 2, 3 or 4; and r is 0 to 5, provided that r is 0 when V is hydrogen;

or a pharmaceutically acceptable salt thereof.

4. The compound according to claim 1 of the formula C:

wherein:
a is N or C;
from 0–4 of b, c, d and e are independently N, NH, O and S, and the remaining b, c, d and e atoms are independently CH, provided that if a is C, then at least one of b, c, d or e is independently N, NH, O or S;

$R^1$ is independently selected from: hydrogen, $C_3$–$C_{10}$ cycloalkyl, $R^{10}O$—, —N$(R^{10})_2$, F or $C_1$–$C_6$ alkyl;

$R^2$ is independently selected from:
  a) hydrogen,
  b) aryl, heterocycle, $C_3$–$C_{10}$ cycloalkyl, $R^{10}O$—, —N$(R^{10})_2$, F or $C_2$–$C_6$ alkenyl,
  c) unsubstituted or substituted $C_1$–$C_6$ alkyl wherein the substituent on the substituted $C_1$–$C_6$ alkyl is selected from unsubstituted or substituted aryl, heterocycle, $C_3$–$C_{10}$ cycloalkyl, $C_2$–$C_6$ alkenyl, $R^{10}O$— and —N$(R^{10})_2$;

$R^3$ and $R^4$ are independently selected from:
  a) hydrogen,
  b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, CN(R$^{10}$)$_2$NC(O)—, $R^{10}_2$N—C(NR$^{10}$)—, CN, NO$_2$, $R^{10}C(O)$—, N$_3$, —N$(R^{10})_2$, or $R^{11}OC(O)NR^{10}$—,
  c) unsubstituted $C_1$–$C_6$ alkyl,
  d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2$NC(O)—, $R^{10}_2$N—C(NR$^{10}$)—, CN, $R^{10}C(O)$—, N$_3$, —N$(R^{10})_2$, and $R^{11}OC(O)NR^{10}$—;

$R^{6a}$, $R^{6b}$, $R^{6c}$, $R^{6d}$ and $R^{6e}$ are independently selected from:
  a) hydrogen,
  b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, CN(R$^{10}$)$_2$NC(O)—, $R^{10}_2$N—C(NR$^{10}$)—, CN, NO$_2$, $R^{10}C(O)$—, N$_3$, —N$(R^{10})_2$, or $R^{11}OC(O)NR^{10}$—,
  c) unsubstituted $C_1$–$C_6$ alkyl,
  d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2$NC(O)—, $R^{10}_2$N—C(NR$^{10}$)—, CN, $R^{10}C(O)$—, N$_3$, —N$(R^{10})_2$, and $R^{11}OC(O)NR^{10}$—;

provided that when $R^{6a}$, $R^{6b}$, $R^{6c}$, $R^{6d}$ or $R^{6e}$ is unsubstituted or substituted heterocycle, attachment of $R^{6a}$, $R^{6b}$, $R^{6c}$, $R^{6d}$ or $R^{6e}$ to Q is through a ring carbon;

$R^8$ is independently selected from:
a) hydrogen,
b) aryl, substituted aryl, heterocycle, $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, —$N(R^{10})_2$, or $R^{11}OC(O)NR^{10}$—, and
c) $C_1$–$C_6$ alkyl substituted by $C_1$–$C_6$ perfluoroalkyl, $R^{10}O$—, $R^{10}C(O)NR^{10}$—, $(R^{10})_2N$—$C(NR^{10})$—, $R^{10}C(O)$—, —$N(R^{10})_2$, or $R^{11}OC(O)NR^{10}$—;

provided that when $R^8$ is heterocycle, attachment of $R^8$ to V is through a ring carbon;

$R^{9a}$ and $R^{9b}$ are independently hydrogen, $C_1$–$C_6$ alkyl, trifluoromethyl and halogen;

$R^{10}$ is independently selected from hydrogen, $C_1$–$C_6$ alkyl, benzyl, 2,2,2-trifluoroethyl and aryl;

$R^{11}$ is independently selected from $C_1$–$C_6$ alkyl and aryl;

$R^{12}$ is independently selected from hydrogen, $C_1$–$C_6$ alkyl, $C_1$–$C_6$ aralkyl, $C_1$–$C_6$ substituted aralkyl, $C_1$–$C_6$ heteroaralkyl, $C_1$–$C_6$ substituted heteroaralkyl, aryl, substituted aryl, heteroaryl, substituted heteroaryl, $C_1$–$C_6$ perfluoroalkyl, 2-aminoethyl and 2,2,2-trifluoroethyl;

$A^1$ and $A^2$ are independently selected from: a bond, —CH=CH—, —C≡C—, —C(O)—, —C(O)NR$^{10}$—, O, —N(R$^{10}$)—, or S(O)$_m$;

V is selected from:
a) hydrogen,
b) heterocycle selected from pyrrolidinyl, imidazolyl, imidazolinyl, pyridinyl, thiazolyl, oxazolyl, indolyl, quinolinyl, isoquinolinyl, triazolyl and thienyl,
c) aryl,
d) $C_1$–$C_{20}$ alkyl wherein from 0 to 4 carbon atoms are replaced with a heteroatom selected from O, S, and N, and
e) $C_2$–$C_{20}$ alkenyl, and provided that V is not hydrogen if $A^1$ is $S(O)_m$ and V is not hydrogen if $A^1$ is a bond, n is 0 and $A^2$ is $S(O)_m$;

provided that when V is heterocycle, attachment of V to $R^8$ and to $A^1$ is through a ring carbon;

X is a bond, —CH=CH—, —C(O)NR$^{10}$—, —NR$^{10}$C(O)—, —NR$^{10}$—, O or —C(=O)—;

provided that if a is N, then X is not —C(O)NR$^{10}$—, —NR$^{10}$— or O ;

m is 0, 1 or 2;

n is independently 0, 1, 2, 3 or 4;

p is 0, 1, 2, 3 or 4, provided that p is not 0 if X is a bond, —NR$^{10}$— or O; and r is 0 to 5, provided that r is 0 when V is hydrogen;

or a pharmaceutically acceptable salt thereof.

5. The compound according to claim 3 of the formula D:

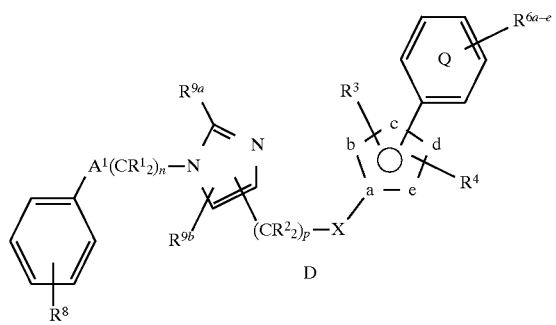

D wherein:
a is N or C;
from 0–4 of b, c, d and e are independently N, NH, O and S, and the remaining b, c, d and e atoms are independently CH, provided that if a is C, then at least one of b, c, d or e is independently N, NH, O or S;
$R^1$ is independently selected from: hydrogen, $C_3$–$C_{10}$ cycloalkyl or $C_1$–$C_6$ alkyl;
$R^2$ is independently selected from:
a) hydrogen,
b) aryl, heterocycle, $C_3$–$C_{10}$ cycloalkyl, $R^{10}O$—, —$N(R^{10})_2$, F or $C_2$–$C_6$ alkenyl,
c) $C_1$–$C_6$ alkyl unsubstituted or substituted by aryl, heterocycle, $C_3$–$C_{10}$ cycloalkyl, $C_2$–$C_6$ alkenyl, $R^{10}O$—, or —$N(R^{10})_2$;
$R^3$ is selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $R^{10}_2N$—$C(NR^{10})$—, CN, $NO_2$, $R^{10}C(O)$—, $N_3$, —$N(R^{10})_2$, or $R^{11}OC(O)NR^{10}$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{10}_2N$—$C(NR^{10})$—, CN, $R^{10}C(O)$—, $N_3$, —$N(R^{10})_2$, and $R^{11}OC(O)NR^{10}$—;

$R^4$ is selected from H, halogen, $C_1$–$C_6$ alkyl and $CF_3$;
$R^{6a}$, $R^{6b}$, $R^{6c}$, $R^{6d}$ and $R^{6e}$ are independently selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $R^{10}_2N$—$C(NR^{10})$—, CN, $NO_2$, $R^{10}C(O)$—, $N_3$, —$N(R^{10})_2$, or $R^{11}OC(O)NR^{10}$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{10}_2N$—$C(NR^{10})$—, CN, $R^{10}C(O)$—, $N_3$, —$N(R^{10})_2$, and $R^{11}OC(O)NR^{10}$—; or any two of $R^{6a}$, $R^{6b}$, $R^{6c}$, $R^{6d}$ and $R^{6e}$ on adjacent carbon atoms are combined to form a diradical selected from —CH═CH—CH═CH—, —CH═CH—CH$_2$—, —(CH$_2$)$_4$— and —(CH$_2$)$_3$—; provided that when $R^{6a}$, $R^{6b}$, $R^{6c}$, $R^{6d}$ or $R^{6e}$ is unsubstituted or substituted heterocycle, attachment of $R^{6a}$, $R^{6b}$, $R^{6c}$, $R^{6d}$ or $R^{6e}$ to Q is through a ring carbon;

$R^8$ is independently selected from:
  a) hydrogen,
  b) aryl, substituted aryl, heterocycle, C$_1$–C$_6$ alkyl, C$_2$–C$_6$ alkenyl, C$_2$–C$_6$ alkynyl, C$_1$–C$_6$ perfluoroalkyl, F, Cl, R$^{10}$O—, R$^{10}$C(O)NR$^{10}$—, CN, NO$_2$, (R$^{10}$)$_2$N—C(NR$^{10}$)—, R$^{10}$C(O)—, —N(R$^{10}$)$_2$, or R$^{11}$OC(O)NR$^{10}$—, and
  c) C$_1$–C$_6$ alkyl substituted by C$_1$–C$_6$ perfluoroalkyl, R$^{10}$O—, R$^{10}$C(O)NR$^{10}$—, (R$^{10}$)$_2$N—C(NR$^{10}$)—, R$^{10}$C(O)—, —N(R$^{10}$)$_2$, or R$^{11}$OC(O)NR$^{10}$—;

provided that when $R^8$ is heterocycle, attachment of $R^8$ to V is through a ring carbon;

$R^{9a}$ and $R^{9b}$ are independently hydrogen, halogen, CF$_3$ or methyl;

$R^{10}$ is independently selected from hydrogen, C$_1$–C$_6$ alkyl, benzyl, 2,2,2-trifluoroethyl and aryl;

$R^{11}$ is independently selected from C$_1$–C$_6$ alkyl and aryl;

$R^{12}$ is independently selected from hydrogen, C$_1$–C$_6$ alkyl, C$_1$–C$_6$ aralkyl, C$_1$–C$_6$ substituted aralkyl, C$_1$–C$_6$ heteroaralkyl, C$_1$–C$_6$ substituted heteroaralkyl, aryl, substituted aryl, heteroaryl, substituted heteroaryl, C$_1$–C$_6$ perfluoroalkyl, 2-aminoethyl and 2,2,2-trifluoroethyl;

$A^1$ is selected from: a bond, —C(O)—, O, —N(R$^{10}$)—, or S(O)$_m$;

X is a bond, —CH═CH—, —C(O)NR$^{10}$—, —NR$^{10}$C(O)—, —NR$^{10}$—, O or —C(═O)—, provided that if a is N, then X is not —C(O)NR$^{10}$—, —NR$^{10}$— or O;

n is 0 or 1; provided n is not 0 if $A^1$ is a bond, O, —N(R$^{10}$)—, or S(O)$_m$;

m is 0, 1 or 2; and p is 0, 1, 2, 3 or 4;

or a pharmaceutically acceptable salt thereof.

6. The compound according to claim 4 of the formula E:

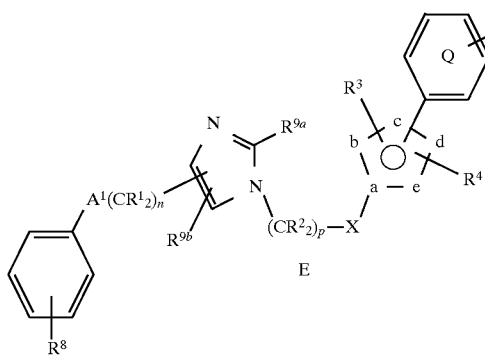

wherein:
  a is N or C;
  from 0–4 of b, c, d and e are independently N, NH, O and S, and the remaining b, c, d and e atoms are independently CH, provided that if a is C, then at least one of b, c, d or e is independently N, NH, O or S;
  $R^1$ is independently selected from: hydrogen, R$^{10}$O—, —N(R$^{10}$)$_2$, F, C$_3$–C$_{10}$ cycloalkyl or C$_1$–C$_6$ alkyl;

$R^2$ is independently selected from:
  a) hydrogen,
  b) aryl, heterocycle, C$_3$–C$_{10}$ cycloalkyl, R$^{10}$O—, —N(R$^{10}$)$_2$, F or C$_2$–C$_6$ alkenyl,
  c) C$_1$–C$_6$ alkyl unsubstituted or substituted by aryl, heterocycle, C$_3$–C$_{10}$ cycloalkyl, C$_2$–C$_6$ alkenyl, R$^{10}$O—, or —N(R$^{10}$)$_2$;

$R^3$ is selected from:
  a) hydrogen,
  b) unsubstituted or substituted aryl, unsubstituted or substituted heterocycle, C$_3$–C$_{10}$ cycloalkyl, C$_2$–C$_6$ alkenyl, C$_2$–C$_6$ alkynyl, halogen, C$_1$–C$_6$ perfluoroalkyl, R$^{12}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, NO$_2$, R$^{10}$C(O)—, N$_3$, —N(R$^{10}$)$_2$, or R$^{11}$OC(O)NR$^{10}$—,
  c) unsubstituted C$_1$–C$_6$ alkyl,
  d) substituted C$_1$–C$_6$ alkyl wherein the substituent on the substituted C$_1$–C$_6$ alkyl is selected from unsubstituted or substituted aryl, unsubstituted or substituted heterocyclic, C$_3$–C$_{10}$ cycloalkyl, C$_2$–C$_6$ alkenyl, C$_2$–C$_6$ alkynyl, R$^{12}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, R$^{10}$C(O)—, N$_3$, —N(R$^{10}$)$_2$, and R$^{11}$C(O)—NR$^{10}$—;

$R^4$ is selected from H, halogen, C$_1$–C$_6$ alkyl and CF$_3$;

$R^{6a}$, $R^{6b}$, $R^{6c}$, $R^{6d}$ and $R^{6e}$ are independently selected from:
  a) hydrogen,
  b) unsubstituted or substituted aryl, unsubstituted or substituted heterocycle, C$_3$–C$_{10}$ cycloalkyl, C$_2$–C$_6$ alkenyl, C$_2$–C$_6$ alkynyl, halogen, C$_1$–C$_6$ perfluoroalkyl, R$^{12}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, NO$_2$, R$^{10}$C(O)—, N$_3$, —N(R$^{10}$)$_2$, or R$^{11}$OC(O)NR$^{10}$—,
  c) unsubstituted C$_1$–C$_6$ alkyl,
  d) substituted C$_1$–C$_6$ alkyl wherein the substituent on the substituted C$_1$–C$_6$ alkyl is selected from unsubstituted or substituted aryl, unsubstituted or substituted heterocyclic, C$_3$–C$_{10}$ cycloalkyl, C$_2$–C$_6$ alkenyl, C$_2$–C$_6$ alkynyl, R$^{12}$O—, R$^{11}$S(O)$_m$—, R$^{10}$C(O)NR$^{10}$—, (R$^{10}$)$_2$NC(O)—, R$^{10}$$_2$N—C(NR$^{10}$)—, CN, R$^{10}$C(O)—, N$_3$, —N(R$^{10}$)$_2$, and R$^{11}$OC(O)—NR$^{10}$—;

provided that when $R^{6a}$, $R^{6b}$, $R^{6c}$, $R^{6d}$ or $R^{6e}$ is unsubstituted or substituted heterocycle, attachment of $R^{6a}$, $R^{6b}$, $R^{6c}$, $R^{6d}$ or $R^{6e}$ to Q is through a ring carbon;

$R^8$ is independently selected from:
  a) hydrogen,
  b) aryl, substituted aryl, heterocycle, C$_1$–C$_6$ alkyl, C$_2$–C$_6$ alkenyl, C$_2$–C$_6$ alkynyl, C$_1$–C$_6$ perfluoroalkyl, F, Cl, R$^{10}$O—, R$^{10}$C(O)NR$^{10}$—, CN, NO$_2$, (R$^{10}$)$_2$N—C(NR$^{10}$)—, R$^{10}$C(O)—, —N(R$^{10}$)$_2$, or R$^{11}$OC(O)NR$^{10}$—, and
  c) C$_1$–C$_6$ alkyl substituted by C$_1$–C$_6$ perfluoroalkyl, R$^{10}$O—, R$^{10}$C(O)NR$^{10}$—, (R$^{10}$)$_2$N—C(NR$^{10}$)—, R$^{10}$C(O)—, —N(R$^{10}$)$_2$, or R$^{11}$OC(O)NR$^{10}$—;

provided that when $R^8$ is heterocycle, attachment of $R^8$ to V is through a ring carbon;

$R^{9a}$ and $R^{9b}$ are independently hydrogen, halogen, CF$_3$ or methyl;

$R^{10}$ is independently selected from hydrogen, C$_1$–C$_6$ alkyl, benzyl, 2,2,2-trifluoroethyl and aryl;

$R^{11}$ is independently selected from C$_1$–C$_6$ alkyl and aryl;

$R^{12}$ is independently selected from hydrogen, C$_1$–C$_6$ alkyl, C$_1$–C$_6$ aralkyl, C$_1$–C$_6$ substituted aralkyl, C$_1$–C$_6$ heteroaralkyl, $C_1$–$C_6$ substituted heteroaralkyl, aryl, substituted aryl, heteroaryl, substituted heteroaryl, $C_1$–$C_6$ perfluoroalkyl, 2-aminoethyl and 2,2,2-trifluoroethyl;

X is a bond, —CH=CH—, —C(O)NR$^{10}$—, —NR$^{10}$C(O)—, —NR$^{10}$—, O or —C(=O)—;

provided that if a is N, then X is not —C(O)NR$^{10}$—, —NR$^{10}$— or O;

n is 0 or 1;

m is 0, 1 or 2; and p is 0, 1, 2, 3 or 4, provided that p is not 0 if X is a bond, —NR$^{10}$C(O)—, —NR$^{10}$— or O;

or a pharmaceutically acceptable salt thereof.

7. The compound according to claim 5 of the formula F:

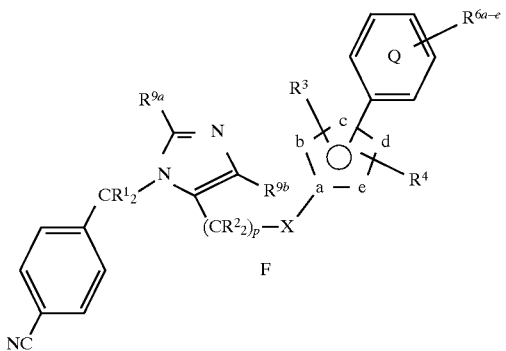

F wherein:

a is N or C;

from 0–4 of b, c, d and e are independently N, NH, O and S, and the remaining b, c, d and e atoms are independently CH, provided that if a is C, then at least one of b, c, d or e is independently N, NH, O or S;

$R^1$ is independently selected from: hydrogen, $C_3$–$C_{10}$ cycloalkyl or $C_1$–$C_6$ alkyl;

$R^2$ is independently selected from:
a) hydrogen,
b) aryl, heterocycle, $C_3$–$C_{10}$ cycloalkyl, $R^{10}$O—, —N($R^{10}$)$_2$ or F,
c) $C_1$–$C_6$ alkyl unsubstituted or substituted by aryl, heterocycle, $C_3$–$C_{10}$ cycloalkyl, $R^{10}$O—, or —N($R^{10}$)$_2$;

$R^3$ is selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}$O—, $R^{11}$S(O)$_m$—, $R^{10}$C(O)R$^{10}$—, ($R^{10}$)$_2$NC(O)—, $R^{10}{}_2$N—C(NR$^{10}$)—, CN, NO$_2$, $R^{10}$C(O)—, N$_3$, —N($R^{10}$)$_2$, or $R^{11}$OC(O)NR$^{10}$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}$O—, $R^{11}$S(O)$_m$—, $R^{10}$C(O)NR$^{10}$—, ($R^{10}$)$_2$NC(O)—, $R^{10}{}_2$N—C(NR$^{10}$)—, CN, $R^{10}$C(O)—, N$_3$, —N($R^{10}$)$_2$, and $R^{11}$OC(O)—NR$^{10}$—;

$R^4$ is selected from H, halogen, CH$_3$ and CF$_3$;

$R^{6a}$, $R^{6b}$, $R^{6c}$, $R^{6d}$ and $R^{6e}$ are independently selected from:

a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}$O—, $R^{11}$S(O)$_m$—, $R^{10}$C(O)NR$^{10}$—, ($R^{10}$)$_2$NC(O)—, $R^{10}{}_2$N—C(NR$^{10}$)—, CN, NO$_2$, $R^{10}$C(O)—, N$_3$, —N($R^{10}$)$_2$, or $R^{11}$OC(O)NR$^{10}$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}$O—, $R^{11}$S(O)$_m$—, $R^{10}$C(O)NR$^{10}$—, ($R^{10}$)$_2$NC(O)—, $R^{10}{}_2$N—C(NR$^{10}$)—, CN, $R^{10}$C(O)—, N$_3$, —N($R^{10}$)$_2$, and $R^{11}$OC(O)—NR$^{10}$—; or any two of $R^{6a}$, $R^{6b}$, $R^{6c}$, $R^{6d}$ and $R^{6e}$ on adjacent carbon atoms are combined to form a diradical selected from —CH=CH—CH=CH—, —CH=CH—CH$_2$—, —(CH$_2$)$_4$— and —(CH$_2$)$_3$—;

provided that when $R^{6a}$, $R^{6b}$, $R^{6c}$, $R^{6d}$ or $R^{6e}$ is unsubstituted or substituted heterocycle, attachment of $R^{6a}$, $R^{6b}$, $R^{6c}$, $R^{6d}$ or $R^{6e}$ to Q is through a ring carbon;

$R^{9a}$ and $R^{9b}$ are independently hydrogen, halogen, CF$_3$ or methyl;

$R^{10}$ is independently selected from hydrogen, $C_1$–$C_6$ alkyl, benzyl, 2,2,2-trifluoroethyl and aryl;

$R^{11}$ is independently selected from $C_1$–$C_6$ alkyl and aryl;

$R^{12}$ is independently selected from hydrogen, $C_1$–$C_6$ alkyl, $C_1$–$C_6$ aralkyl, $C_1$–$C_6$ substituted aralkyl, $C_1$–$C_6$ heteroaralkyl, $C_1$–$C_6$ substituted heteroaralkyl, aryl, substituted aryl, heteroaryl, substituted heteroaryl, $C_1$–$C_6$ perfluoroalkyl, 2-aminoethyl and 2,2,2-trifluoroethyl;

X is a bond, —CH=CH—, —C(O)NR$^{10}$—, —NR$^{10}$C(O)—, O or —C(=O)—;

provided that if a is N, then X is not —C(O)NR$^{10}$— or O;

m is 0, 1 or 2; and p is 0, 1, 2, 3 or 4;

or a pharmaceutically acceptable salt thereof.

8. The compound according to claim 6 of the formula G:

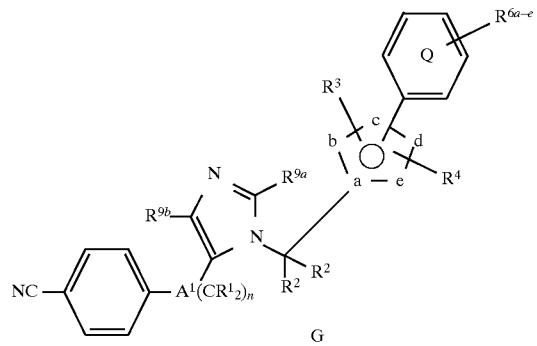

G wherein:

a is C;

from 0–4 of b, c, d and e are independently N, NH, O and S, and the remaining b, c, d and e atoms are independently CH, provided that at least one of b, c, d or e is independently N, NH, O or S;

$R^1$ is independently selected from: hydrogen, $R^{10}$O—, —N($R^{10}$)$_2$, F, $C_3$–$C_{10}$ cycloalkyl or $C_1$–$C_6$ alkyl;

R² is independently selected from:
a) hydrogen,
b) aryl, heterocycle or $C_3$–$C_{10}$ cycloalkyl,
c) $C_1$–$C_6$ alkyl unsubstituted or substituted by aryl, heterocycle, $C_3$–$C_{10}$ cycloalkyl, $C_2$–$C_6$ alkenyl, $R^{10}O$—, or —$N(R^{10})_2$;

R³ is selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $R^{10}_2N$—$C(NR^{10})$—, CN, $NO_2$, $R^{10}C(O)$—, $N_3$, —$N(R^{10})_2$, or $R^{11}OC(O)NR^{10}$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{10}_2N$—$C(NR^{10})$—, CN, $R^{10}C(O)$—, $N_3$, —$N(R^{10})_2$, and $R^{11}OC(O)NR^{10}$—;

R⁴ is selected from H, halogen, $CH_3$ and $CF_3$;

$R^{6a}$, $R^{6b}$, $R^{6c}$, $R^{6d}$ and $R^{6e}$ are independently selected from:
a) hydrogen,
b) unsubstituted or substituted aryl, unsubstituted or substituted heterocycle, $C_3$–$C_{10}$ cycloalkyl, $C_2$–$C_6$ alkenyl, $C_2$–$C_6$ alkynyl, halogen, $C_1$–$C_6$ perfluoroalkyl, $R^{12}O$—, $R^{11}S(O)_m$—, $R^{10}C(O)NR^{10}$—, $(R^{10})_2NC(O)$—, $R^{10}_2N$—$C(NR^{10})$—, CN, $NO_2$, $R^{10}C(O)$—, $N_3$, —$N(R^{10})_2$, or $R^{11}OC(O)NR^{10}$—,
c) unsubstituted $C_1$–$C_6$ alkyl,
d) substituted $C_1$–$C_6$ alkyl wherein the substituent on the substituted $C_1$–$C_6$ alkyl is selected from unsubstituted or substituted aryl, unsubstituted or substituted heterocyclic, $C_3$–$C_{10}$ cycloalkyl, $C_2$–$C_6$ alkenyl, $C_2$–$C_6$ alkynyl, $R^{12}O$—, $R^{11}S(O)_m$—, $R^{10}C(O)NR^{10}$—, $(R^{10})_2NC(O)$—, $R^{10}_2N$—$C(NR^{10})$—, CN, $R^{10}C(O)$—, $N_3$, —$N(R^{10})_2$, and $R^{11}OC(O)NR^{10}$—; or any two of $R^{6a}$, $R^{6b}$, $R^{6c}$, $R^{6d}$ and $R^{6e}$ on adjacent carbon atoms are combined to form a diradical selected from —CH=CH—CH=CH—, —CH=CH—$CH_2$—, —$(CH_2)_4$— and —$(CH_2)_3$—;

provided that when $R^{6a}$, $R^{6b}$, $R^{6c}$, $R^{6d}$ or $R^{6e}$ is unsubstituted or substituted heterocycle, attachment of $R^{6a}$, $R^{6b}$, $R^{6c}$, $R^{6d}$ or $R^{6e}$ to Q is through a ring carbon;

$R^{9a}$ and $R^{9b}$ are independently hydrogen, halogen, $CF_3$ or methyl;

$R^{10}$ is independently selected from hydrogen, $C_1$–$C_6$ alkyl, benzyl, 2,2,2-trifluoroethyl and aryl;

$R^{11}$ is independently selected from $C_1$–$C_6$ alkyl and aryl;

$R^{12}$ is independently selected from hydrogen, $C_1$–$C_6$ alkyl, $C_1$–$C_6$ aralkyl, $C_1$–$C_6$ substituted aralkyl, $C_1$–$C_6$ heteroaralkyl, $C_1$–$C_6$ substituted heteroaralkyl, aryl, substituted aryl, heteroaryl, substituted heteroaryl, $C_1$–$C_6$ perfluoroalkyl, 2-aminoethyl and 2,2,2-trifluoroethyl; p1 $A^1$ is selected from: a bond, —C(O)—, O, —$N(R^{10})$—, or $S(O)_m$;

m is 0, 1 or 2; and
n is 0 or 1;

or the pharmaceutically acceptable salts thereof.

9. A compound which inhibits farnesyl-protein transferase which is:
1-{[1-(4-Cyanobenzyl)-1H-imidazol-5-yl]ethyl}-4-phenyl-imidazole
1-{1-(4-Cyanobenzyl)-1H-imidazol-5-yl)methyl}-4-(2-methyl)phenyl imidazole
1-(3-Phenyl-5-isoxazolylmethyl)-5-(4-cyanobenzyl) imidazole
1-(3-Phenyl-isoxazol-5-ylacetyl)-5-(4-cyanobenzyl) imidazole
1-(4-Cyanobenzyl)-5-(4-Phenyl-thiazol-2-ylmethyl) imidazole
1-(4-Cyanobenzyl)-5-(4-(2-methylphenyl)-thiazol-2-ylmethyl)imidazole
1-(4-Cyanobenzyl)-5-(4-(3-chlorophenyl)-thiazol-2-ylmethyl)imidazole or
1-(4-Cyanobenzyl)-5-(4-(naphth-2-yl)-thiazol-2-ylmethyl)imidazole
1-((4-(2-methylphenyl)-5-methylthiazole-2-ylmethyl)-5-(4-cyanobenzyl) imidazole or
1-((4-(2-methylphenyl)thiazole-2-ylethyl)-5-(4-cyanobenzyl) imidazole or a pharmaceutically acceptable salt thereof.

10. The compound according to claim 9 which is:

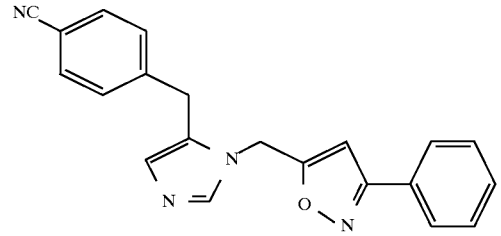

or a pharmaceutically acceptable salt thereof.

11. The compound according to claim 9 which is:

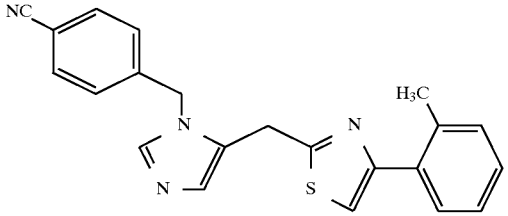

or a pharmaceutically acceptable salt thereof.

12. The compound according to claim 9 which is:

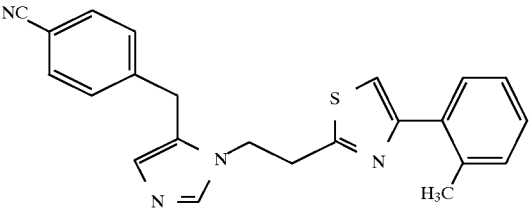

or a pharmaceutically acceptable salt or optical isomer thereof.

13. A pharmaceutical composition comprising a pharmaceutical carrier, and dispersed therein, a therapeutically effective amount of a compound of claim 1.

14. A pharmaceutical composition comprising a pharmaceutical carrier, and dispersed therein, a therapeutically effective amount of a compound of claim 3.

15. A pharmaceutical composition comprising a pharmaceutical carrier, and dispersed therein, a therapeutically effective amount of a compound of claim 4.

16. A pharmaceutical composition comprising a pharmaceutical carrier, and dispersed therein, a therapeutically effective amount of a compound of claim 9.

17. A method for inhibiting farnesyl-protein transferase which comprises administering to a mammal in need thereof a therapeutically effective amount of a composition of claim 13.

18. A method for inhibiting farnesyl-protein transferase which comprises administering to a mammal in need thereof a therapeutically effective amount of a composition of claim 14.

19. A method for inhibiting farnesyl-protein transferase which comprises administering to a mammal in need thereof a therapeutically effective amount of a composition of claim 15.

20. A method for inhibiting farnesyl-protein transferase which comprises administering to a mammal in need thereof a therapeutically effective amount of a composition of claim 16.

21. A method for treating cancer which comprises administering to a mammal in need thereof a therapeutically effective amount of a composition of claim 13.

22. A method for treating cancer which comprises administering to a mammal in need thereof a therapeutically effective amount of a composition of claim 14.

23. A method for treating cancer which comprises administering to a mammal in need thereof a therapeutically effective amount of a composition of claim 15.

24. A method for treating cancer which comprises administering to a mammal in need thereof a therapeutically effective amount of a composition of claim 16.

25. A method for treating neurofibromin benign proliferative disorder which comprises administering to a mammal in need thereof a therapeutically effective amount of a composition of claim 13.

26. A method for treating blindness related to retinal vascularization which comprises administering to a mammal in need thereof a therapeutically effective amount of a composition of claim 13.

27. A method for treating infections from hepatitis delta and related viruses which comprises administering to a mammal in need thereof a therapeutically effective amount of a composition of claim 13.

28. A method for preventing restenosis which comprises administering to a mammal in need thereof a therapeutically effective amount of a composition of claim 13.

29. A method for treating polycystic kidney disease which comprises administering to a mammal in need thereof a therapeutically effective amount of a composition of claim 14.

30. A pharmaceutical composition made by combining the compound of claim 1 and a pharmaceutically acceptable carrier.

31. A process for making a pharmaceutical composition comprising combining a compound of claim 1 and a pharmaceutically acceptable carrier.

* * * * *

UNITED STATES PATENT AND TRADEMARK OFFICE
CERTIFICATE OF CORRECTION

PATENT NO. : 5,859,035

DATED : January 12, 1999

INVENTOR(S) : Neville J. Anthony, Robert P. Gomez and Steven D. Young

It is certified that error appears in the above-identified patent and that said Letters Patent is hereby corrected as shown below:

On the title page item [57] Abstract should read:

-- The present invention is directed to compounds which inhibit farnesyl-protein transferase (FTase) and the farnesylation of the oncogene protein Ras. The invention is further directed to chemotherapeutic compositions containing the compounds of this invention and methods for inhibiting farnesyl-protein transferase and the farnesylation of the oncogene protein Ras. --.

Signed and Sealed this

Twenty-seventh Day of July, 1999

Attest:

Q. TODD DICKINSON

*Attesting Officer*     Acting Commissioner of Patents and Trademarks